(12) United States Patent
Bhat et al.

(10) Patent No.: US 8,813,753 B2
(45) Date of Patent: Aug. 26, 2014

(54) IMPLANTABLE OBSTRUCTIVE SLEEP APNEA SENSOR

(75) Inventors: Nikhil D. Bhat, Fremont, CA (US);
Charisse M. Yung, Mountain View, CA (US); Anant V. Hegde, Hayward, CA (US); George Y. Choi, Redwood City, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 1532 days.

(21) Appl. No.: 12/235,536

(22) Filed: Sep. 22, 2008

(65) Prior Publication Data

US 2009/0078274 A1   Mar. 26, 2009

Related U.S. Application Data

(63) Continuation-in-part of application No. 11/613,027, filed on Dec. 19, 2006, now abandoned, which is a continuation-in-part of application No. 10/946,435, filed on Sep. 21, 2004, now Pat. No. 7,836,888, and a continuation-in-part of application No. 11/233,493, filed on Sep. 21, 2005, now abandoned, and a continuation-in-part of application No. 11/355,927, filed on Feb. 15, 2006, now Pat. No. 7,882,842.

(60) Provisional application No. 61/055,405, filed on May 22, 2008.

(51) Int. Cl.
| | | |
|---|---|---|
| *A61B 17/56* | (2006.01) |
| *A61B 17/58* | (2006.01) |
| *A61B 17/70* | (2006.01) |
| *A61B 19/00* | (2006.01) |
| *A61F 2/02* | (2006.01) |
| *A61F 2/08* | (2006.01) |
| *A61F 2/20* | (2006.01) |
| *A61F 2/30* | (2006.01) |
| *A61F 5/04* | (2006.01) |
| *A61F 5/14* | (2006.01) |
| *A61F 5/37* | (2006.01) |
| *A61C 5/14* | (2006.01) |

(52) U.S. Cl.
USPC ........... 128/848; 128/846; 128/898; 424/422; 424/423; 523/113; 602/902; 606/53; 606/60; 606/251; 606/263; 623/4.1; 623/5.16; 623/9; 623/11.11; 623/14.13; 623/17.17

(58) Field of Classification Search
CPC ............... A61F 2/00; A61F 2/02; A61F 2/08; A61F 2/0805; A61F 2/0811; A61F 5/56; A61F 5/566; A61B 17/1671; A61B 17/663; A61B 17/7032; A61B 17/7052; A61L 27/16; A61L 27/18
USPC ............. 128/846, 848, 898; 623/4.1, 5.16, 9, 623/11.11, 14.13, 17.17; 606/60, 53, 251, 606/263; 424/422, 423; 523/113; 602/902
See application file for complete search history.

(56) References Cited

U.S. PATENT DOCUMENTS 5,176,618 A   1/1993   Freedman
5,979,456 A   11/1999  Magovern
(Continued)

OTHER PUBLICATIONS

U.S. Appl. No. 12/072,680, filed Feb. 27, 2008, Doelling et al.

*Primary Examiner* — Patricia Bianco
*Assistant Examiner* — Brandon L Jackson
(74) *Attorney, Agent, or Firm* — Dicke, Billig & Czaja, PLLC

(57) ABSTRACT

Systems and methods for detecting an obstructive sleep apnea event are disclosed herein. The systems and methods may use an electrical output generating ionic polymer metal composite sensor attached to a region in an airway passage in an oral cavity. The electrical output may be wirelessly transmitted as a signal for indication of an obstructive sleep apnea event. The signal may be further analyzed for treatment of the obstructive sleep apnea event.

19 Claims, 51 Drawing Sheets

(56) References Cited

U.S. PATENT DOCUMENTS

| | | | |
|---|---|---|---|
| 6,475,639 B2* | 11/2002 | Shahinpoor et al. | 428/614 |
| 6,749,556 B2* | 6/2004 | Banik | 600/30 |
| 6,955,172 B2 | 10/2005 | Nelson et al. | |
| 7,073,505 B2 | 7/2006 | Nelson et al. | |
| 7,188,627 B2 | 3/2007 | Nelson et al. | |
| 7,216,648 B2 | 5/2007 | Nelson et al. | |
| 7,277,749 B2* | 10/2007 | Gordon et al. | 607/2 |
| 7,360,542 B2 | 4/2008 | Nelson et al. | |
| 7,367,340 B2 | 5/2008 | Nelson et al. | |
| 7,836,888 B2* | 11/2010 | Hegde et al. | 128/848 |
| 7,882,842 B2* | 2/2011 | Bhat et al. | 128/899 |
| 8,175,717 B2* | 5/2012 | Haller et al. | 607/61 |
| 2002/0045921 A1* | 4/2002 | Wolinsky et al. | 607/61 |
| 2004/0073272 A1* | 4/2004 | Knudson et al. | 607/48 |
| 2004/0149290 A1* | 8/2004 | Nelson et al. | 128/848 |
| 2004/0172054 A1* | 9/2004 | Metzger et al. | 606/196 |
| 2005/0115572 A1* | 6/2005 | Brooks et al. | 128/863 |
| 2005/0121039 A1* | 6/2005 | Brooks et al. | 128/863 |
| 2005/0159637 A9 | 7/2005 | Nelson et al. | |
| 2006/0009856 A1* | 1/2006 | Sherman et al. | 623/20.32 |
| 2007/0186936 A1 | 8/2007 | Nelson et al. | |
| 2008/0066764 A1 | 3/2008 | Paraschac et al. | |
| 2008/0066765 A1 | 3/2008 | Paraschac et al. | |
| 2008/0066766 A1 | 3/2008 | Paraschac et al. | |
| 2008/0066767 A1 | 3/2008 | Paraschac et al. | |
| 2008/0306396 A1* | 12/2008 | Ariav et al. | 600/527 |

* cited by examiner $g_{ref.}$ = reference gap to be maintained
$g_{act.}$ = actual gap measured by the sensor

IMPLANTABLE OBSTRUCTIVE SLEEP APNEA SENSOR

CROSS-REFERENCES TO RELATED APPLICATIONS

This application is a continuation-in-part of U.S. patent application Ser. No. 11/613,027, filed on Dec. 19, 2006, now abandoned which is a continuation-in-part of U.S. patent application Ser. No. 10/946,435, filed on Sep. 21, 2004, now U.S. Pat. No. 7,836,888, and Ser. No. 11/233,493 filed on Sep. 21, 2005, now abandoned and Ser. No. 11/355,927 filed on Feb. 15, 2006, now U.S. Pat. No. 7,882,842 this application is also a continuation-in-part of U.S. Provisional Application 61/055,405, filed on May 22, 2008; all of which are incorporated by reference herein in their entireties.

BACKGROUND OF THE INVENTION

Snoring is very common among mammals including humans. Snoring is a noise produced while breathing during sleep due to the vibration of the soft palate and uvula. Not all snoring is bad, except it bothers the bed partner or others near the person who is snoring. If the snoring gets worst overtime and goes untreated, it could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway becomes blocked, making breathing labored and noisy and even stopping it altogether. Sleep apnea also can occur in obese people when an excess amount of tissue in the airway causes it to be narrowed.

In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by primary care physicians, pulmonologists, neurologists, or other physicians with specialty training in sleep disorders. Diagnosis of sleep apnea is not simple because there can be many different reasons for disturbed sleep.

The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure. It is not used to treat obstructive sleep apnea.

Nasal continuous positive airway pressure (CPAP) is the most common treatment for sleep apnea. In this procedure, the patient wears a mask over the nose during sleep, and pressure from an air blower forces air through the nasal passages. The air pressure is adjusted so that it is just enough to prevent the throat from collapsing during sleep. The pressure is constant and continuous. Nasal CPAP prevents airway closure while in use, but apnea episodes return when CPAP is stopped or it is used improperly. Many variations of CPAP devices are available and all have the same side effects such as nasal irritation and drying, facial skin irritation, abdominal bloating, mask leaks, sore eyes, and headaches. Some versions of CPAP vary the pressure to coincide with the person's breathing pattern, and other CPAPs start with low pressure, slowly increasing it to allow the person to fall asleep before the full prescribed pressure is applied.

Dental appliances that reposition the lower jaw and the tongue have been helpful to some patients with mild to moderate sleep apnea or who snore but do not have apnea. A dentist or orthodontist is often the one to fit the patient with such a device.

Some patients with sleep apnea may need surgery. Although several surgical procedures are used to increase the size of the airway, none of them is completely successful or without risks. More than one procedure may need to be tried before the patient realizes any benefits. Some of the more common procedures include removal of adenoids and tonsils (especially in children), nasal polyps or other growths, or other tissue in the airway and correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea itself. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses RF to reduce the size of some airway structures such as the uvula and the back of the tongue. This technique helps in reducing snoring and is being investigated as a treatment for apnea.

Tracheostomy is used in persons with severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients in whom sleep apnea is due to deformities of the lower jaw may benefit from surgical reconstruction. Surgical procedures to treat obesity are sometimes recommended for sleep apnea patients who are morbidly obese. Behavioral changes are an important part of the treatment program, and in mild cases behavioral therapy may be all that is needed. Overweight persons can benefit from losing weight. Even a 10 percent weight loss can reduce the number of apneic events for most patients. Individuals with apnea should avoid the use of alcohol and sleeping pills, which make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, Restore Medical, Inc., Saint Paul, Minn. has developed a new treatment for snoring and apnea, called the Pillar technique. Pillar System is a procedure where 2 or 3 small polyester rod devices are placed in the patient's soft palate. The Pillar System stiffens the palate, reduces vibration of the tissue, and prevents the possible airway collapse. Stiff implants in the soft palate, however, could hinder patient's normal functions like speech, ability to swallow, coughing and sneezing. Protrusion of the modified tissue into the airway is another long-term concern.

As the current treatments for snoring and/or apnea are not effective and have side-effects, there is a need for additional treatment options.

BRIEF SUMMARY OF THE INVENTION

Methods and devices for the treatment of airway disorders, such as snoring and/or apnea are disclosed herein. The device described herein comprises an actuator element. The actuator element is partially or completely implanted in an airway passageway wall or adjacent to an air passageway wall to treat the improper opening and closing of the passageway. In preferred embodiments, the actuator element is an electroactive polymer (EAP) element. The actuator element is typically inserted into the soft palate and/or sidewalls of the patient's airway. In one embodiment, the EAP element has a low stiffness under normal conditions. The EAP element is energized when the opening of the air passageway has to be maintained open, such as during sleep. When the EAP element is energized, the polymer stiffens and tends to deform and thus has the ability to support the weight of the soft palate and sidewalls of the air ways and open the air passageways. When the charge is removed, the EAP element becomes soft and tends not to interfere with the patient's normal activities like swallowing and speech. The airway implant devices described herein may completely or partially open the relevant air passageways.

One or more implants are placed in the soft palate, sidewalls of the airway, around the trachea, in the tongue, in the uvula, or in combinations thereof. The implant has lead wires (e.g., anode and cathode) attached to the EAP element. In some embodiments, the lead wires are connected to an induction coil. The induction coil is typically implanted in the roof of the mouth. Preferably, the patient wears a retainer type of device before going to bed. The retainer has an induction coil, a circuit and a battery. When the patient wears the retainer, the induction coil in the retainer is proximal to the induction coil that is implanted in the roof of the mouth. The energy is then transmitted through the tissue and to the coil that is in the roof of the mouth. When the EAP element is energized it deforms and/or stiffens to provide support to so as to completely or partially open the airways. In the morning when the patient wakes up, the patient removes the retainer and places the retainer on a charging unit to recharge the battery.

A first aspect of the invention is an airway implant device comprising an electroactive polymer element which is adapted and configured to modulate the opening of an air passageway. In some embodiments the device includes an anode and a cathode connected to the electroactive polymer element, an inductor, and a controller. The controller can be a microprocessor which is adapted and configured to sense the opening of the air passageway and control the energizing of the electroactive polymer element. Other embodiments of the device include a non-implanted portion, such as a mouth guard. Preferably, the non-implanted portion is adapted and configured to control the electroactive polymer element. The non-implanted portion also typically includes a power source and an inductor. The inductor in the implanted portion is adapted and configured to interact with the inductor in the implanted portion of the device. The device is preferably adapted and configured for implantation into a soft palate and/or a lateral pharyngeal wall. In preferred embodiments, the electroactive polymer element comprises an ion-exchange polymer metal composite. The functioning of the device is preferably by energizing the electroactive polymer element which then causes a complete or partial opening of the air passageway. Preferably, the device comprises an inductive coupling mechanism adapted to connect the electroactive polymer element to a power source Other aspects of the invention are methods of using the devices disclosed herein. One embodiment is a method of controlling an opening of an air passageway by implanting an airway implant device comprising an electroactive polymer element proximal to an air passageway and/or in a wall of an air passageway and controlling the opening of the air passageway by energizing the electroactive polymer element to completely or partially open said air passageway. Preferably the control of the opening of the air passageway is in response to feedback from the air passageway regarding the opening of the air passageway. The airway implant device can be implanted in a soft palate and/or a lateral pharyngeal wall. Preferably, the airway implant device is controlled by an inductive coupling mechanism. This method is preferably used to treat airway disorders such as obstructive sleep apnea or snoring.

Another embodiment is a method of treating a disease using an airway implant device comprising implanting an airway implant device with an actuator element in the soft palate of a patient and controlling the opening of the air passageway by energizing the actuator element. The energizing of the actuator element moves the soft palate to support a collapsed tongue or a tongue that has the tendency to collapse and completely or partially opens the air passageway. The actuator element is preferably a non-magnetic material and even more preferably an electroactive polymer.

Yet another embodiment is a method of treating a disease using an airway implant device comprising implanting an airway implant device with an actuator element in a lateral pharyngeal wall and controlling the opening of the air passageway by energizing the actuator element, wherein the energizing of the actuator element supports the lateral pharyngeal wall and completely or partially opens the air passageway. The actuator element is preferably a non-magnetic material and even more preferably an electroactive polymer.

In one aspect of the invention the airway implant device further comprises a sensor element. The sensor element monitors the condition of the airway. Preferably, this monitoring of the airway is used to predict the occurrence of an apneic event or a snoring event. The sensor element can be in the same unit as the airway implant or can be in a separate unit. The sensor element can be implanted proximal to or in an airway wall. The sensor element, in some embodiments, provides feedback based on the monitoring directly or indirectly to the actuator element. The actuation of the actuator element in these embodiments is typically related to the feedback from the sensor element. In some embodiments, the actuator element functions as the sensor element. One embodiment of the invention is an airway implant device comprising an actuator element and a sensor element, wherein the actuator element is adapted and configured to modulate an opening of an air passageway and the sensor element is adapted and configured to monitor a condition of an airway to determine the likelihood of an apneic event. The condition being monitored can include an air passageway gap, air flow pressure, and/or wall tension. The actuator element and the sensor element can be in two separate units. Preferably, the sensor element provides feedback to modulate the opening of the air passageway by the actuator element. The device can further include a microprocessor adapted and configured to communicate with the sensor regarding the opening of the air passageway and controlling an energizing of the actuator element based on this communication with the sensor element.

The device can also include a non-implanted portion. In some embodiments, the non-implanted portion comprises a power source and in other embodiments it comprises a microprocessor adapted and configured to communicate with the sensor regarding the opening of the air passageway and controlling an energizing of the actuator element based on this communication with the sensor element. The sensor element can be located proximal to or in the nose, nostril, soft palate, tongue, laryngeal wall, and/or a pharyngeal wall. The sensor element can be a non-contact distance sensor, pressure sensor, flow sensor, and/or a wall tension sensor.

Another aspect of the invention is methods of use of the airway implant device which include a sensor. One embodiment is a method of treating a disease using an airway implant device comprising implanting an actuator element proximal to and/or in a wall of an air passageway, wherein the actuator element is adapted and configured to monitor a condition of the air passageway to determine likelihood of an apneic event and to modulate an opening of the air passageway based on the monitoring. Another embodiment is a method of treating a disease using an airway implant device comprising implanting an actuator element and a sensor element proximal to and/or in a wall of an air passageway, wherein the actuator element is adapted and configured to modulate an opening of an air passageway and the sensor is adapted and configured to monitor a condition of the air passageway to determine likelihood of an apneic event. The sensor element can be further adapted and configured to provide a feedback to the actuator element regarding the condition being monitored and the modulation by the actuator element is related to the feedback. The sensor element can also activate the actuator element, the activation being related to the monitoring by the sensor element. Diseases suitable for treatment with the devices include obstructive sleep apnea and/or snoring. Yet another embodiment is a method of treating a disease using an airway implant device comprising implanting an actuator element and a sensor element proximal to and/or in a wall of an air passageway; the actuator element being adapted and configured to control an opening of an air passageway by energizing the actuator element, wherein the energizing of the actuator element moves the soft palate to support a collapsed tongue and completely or partially opens the air passageway or supports the lateral pharyngeal wall and completely or partially opens up the air passageway and the energizing is in response to feedback from the sensor element regarding an opening of the air passageway.

In yet another aspect of the invention the airway implant device comprises an actuator element, a first inductor, and a housing which houses the first inductor, wherein the actuator element is adapted and configured to modulate an opening of an air passageway. The housing can be made wholly or in part of acrylic, polytetrafluoroethylene (PTFE), polymethylmethacrylate (PMMA), Acrylonitrile Butadiene Styrene (ABS), polyurethane, polycarbonate, cellulose acetate, nylon, and/or a thermoplastic or thermosetting material. The housing can be configured using an appropriate shape to reduce or eliminate rocking of the implant across the hard palate ridge. For example, the housing can be cast to comport to the shape of a patient palate, or cast from an impression of a patient palate. In another example, the housing can be cast from the palate of the patient for whom the implant is intended. Other examples are where the housing is formed to be substantially smooth rounded, concave, convex, or have bumps on its superior side. If there are bumps on the housing superior side, these bumps can be configured such that when implanted in the palate, there is at least one bump on one lateral side of the hard palate ridge, and at least one bump on the other lateral side of the hard palate ridge. The housing can be substantially smooth and rounded on its inferior side surface. In some embodiments the implant is secured to tissue using at least one of an anchor, suture, or an adhesive. In some embodiments the implant device further comprises an attachment element wherein the attachment element is capable of attaching to sutures and capable of securing the implant device to tissue. In some embodiments, the attachment element is at least one of a T-shape, triangular shape, circular shape, L-shape, and a Z-shape. In other embodiments, the attachment element is of a geometry allowing attachment of the implant device to tissue, wherein the attachment is at the anterior end of the implant and secures the position of the implant within the implant cavity. In some embodiments, the implant comprises an attachment element that is bioabsorbable. In some embodiments, the implant attachment element has at least one hole whereby a suture, screw, or tack can pass through the hole and through tissue to fix the implant device position and secure the attachment element to tissue. In some embodiments, the implant device comprises an anchor that is curved and/or configured to allow delivery and removal with minimal tissue damage. In some embodiments the housing has a roughened surface to increase friction, and in some embodiments the roughened surface induces fibrosis. The roughened surface can be created during casting of the housing, or after the housing is created. In some embodiments, the implant device is implanted in a palate. In some embodiments the implant housing is implanted inferior to the hard palate, and the actuator element is implanted in the soft palate. In some embodiments the implanted portion comprises connecting elements comprising a positive contact and a negative contact wherein the contacts connect the actuator element and the inductor and when charged by the inductor, the actuator element is energized. In some embodiments, the actuator element comprises an electroactive polymer. In some embodiments, the housing houses the contacts. When the actuator element is energized, it can stiffen in one direction, or it can deflect, thereby opening the airway in which the device is implanted. In some embodiments, the implant device comprises a non-implanted portion. The non-implanted portion, in some embodiments, comprises a retainer comprising a dental retainer material. In a preferred embodiment, the non-implanted portion comprises a non-implantable wearable element. In some embodiments, the non-implanted portion comprises a power source and a second inductor connected to the power source. The power source can be charged in many ways. It can be replaceable, rechargeable within the non-implanted portion, removable and rechargeable outside the non-implanted portion, or a combination of the above. In some embodiments, the non-implanted portion power source is rechargeable, wherein the non-implanted portion comprises ball clamps having two exposed ball portions, said ball clamps connected to the rechargeable power source, whereby the ball portions can recharge the power source. In some embodiments, the power source is a rechargeable battery. In some embodiments, the power source is a non-rechargeable battery that can be replaced as needed. In some embodiments, the power source is sealed within the non-implanted portion, wherein the sealing is fluid proof.

In yet another embodiment the invention may include a system to sense obstructive sleep apnea, including an ionic polymer metal composite (IPMC) sensor attached to a region in an airway passage in an oral cavity which generates an electrical output when a change in shape of the airway passage in the oral cavity occurs, and a transmitter device electrically coupled to the IPMC sensor and configured to transmit at least one electronic signal. In some embodiments the IPMC sensor includes an electro active polymer material. In some embodiments the IPMC sensor is configured as an elongated strip. In some embodiments the IPMC sensor is placed on the soft palate. In some embodiments the IPMC sensor is placed on the soft palate using an adhesive. In some embodiments the IPMC sensor is implanted into the soft palate. In some embodiments the IPMC sensor includes a second elongated strip which generates a second electronic signal. In some embodiments one elongated strip is placed about the soft palate and another is placed about the side palate or pharyngeal walls. In some embodiments the elongated strips are integral to the transmitter device. In some embodiments the system additionally includes a wireless receiver for receiving the at least one electronic signal, and a control device electronically coupled to the wireless receiver for recording the electronic signal. In some embodiments the control device additionally performs an analysis of the electronic signal. In some embodiments the system additionally includes a therapy device operatively coupled with a region in the airway passage in the oral cavity which is at least partially controlled by the control device. In some embodiments the transmitter device includes translation circuitry which translates the electrical output into the at least one electronic signal. In some embodiments the at least one electronic signal is a digital signal. In some embodiments the at least one electronic signal is an amplified analog signal. In some embodiments the transmitter device includes a wireless transmitter for wirelessly transmitting the at least one electronic signal. In some embodiments the wireless transmitter is configured to transmit under the Bluetooth wireless protocol. In some embodiments the transmitter device includes a battery. In some embodiments at least a portion of the transmitter device is detachable from the IPMC sensor for recharging the battery. In some embodiments the IPMC sensor outputs the electrical output in absence of a power source.

Yet another embodiment of the invention may include a method for sensing obstructive sleep apnea, comprising generating an electrical output from an ionic polymer metal composite (IPMC) sensor attached to a region in an airway passage in an oral cavity, transmitting a signal which is based on the generated electrical output from the IPMC. In some embodiments the method may additionally include translating the generated electrical output into the signal. In some embodiments the signal is digital. In some embodiments the signal is analog. In some embodiments the method additionally includes analyzing the transmitted signal. In some embodiments the method additionally includes creating a predictive algorithm based on the transmitted signal. In some embodiments the method additionally includes sending a control signal to an obstructive sleep apnea treatment device based on the analyzed transmitted signal.

Yet another embodiment of the invention may include a system to treat obstructive sleep apnea, including an ionic polymer metal composite (IPMC) sensor attached to a region in an airway passage in an oral cavity which generates an electrical output when a change in shape of the airway passage in the oral cavity occurs, a transmitter device electrically coupled to the IPMC sensor and configured to transmit at least one electronic signal, and an electronically actuated mandibular repositioning device (MRD) configured to move a jaw from a first position to a second position based on the least one electronic signal to treat the sleep apnea event. In some embodiments IPMC sensor includes an electro active polymer material. In some embodiments IPMC sensor is configured as an elongated strip. In some embodiments the MRD includes a fixed upper jaw positioner configured to align with a portion of an upper denture, at least one linkage with a first end and a second end, the first end moveably attached to the fixed upper jaw positioner, a moveable jaw positioner configured to align with a portion of a lower denture and moveably attached to the second end of linkage, and at least one jaw actuator attached to at least one of the fixed upper jaw, at least one linkage, and moveable jaw positioner. In some embodiments the MRD additionally includes a control circuit. In some embodiments the at least one jaw actuator is controlled by the control circuit. In some embodiments the control circuit is wirelessly coupled to the transmitter device. In some embodiments the control circuit includes a timer. In some embodiments the control circuit includes a motor control. In some embodiments the IPMC sensor is integral with the transmitter device. In some embodiments the at least one electronic signal is a digital signal. In some embodiments the at least one electronic signal is an analog signal.

Yet another embodiment of the invention may include a method to treat sleep apnea, including generating at least one electronic signal from an ionic polymer metal composite (IPMC) sensor attached to a region in an airway passage in an oral cavity when a change in shape of the airway passage in the oral cavity occurs from an obstructive sleep apnea event, analyzing the at least one electronic signal, generating an output based on the at least one electronic signal, and actuating an electronically actuated mandibular repositioning device (MRD) configured to move a jaw from a first position to a second position based on the output to treat the sleep apnea event. In some embodiments the method additionally includes generating at least one additional electronic signal from a second ionic polymer metal composite (IPMC) sensor. In some embodiments the output is generated in a linear or non-linear or an adaptive fashion. In some embodiments output generation is based on neural network algorithms. In some embodiments generating includes converting the at least one additional electronic signal into a digital signal. In some embodiments the MRD includes at least one MRD motor, and actuating the electronically actuated MRD additionally includes activating the at least one MRD motor to move the jaw from the first position to a second position. In some embodiments the at least one electronic signal is generated from an electro active polymer material. In some embodiments the method additionally includes reactuating the MRD to move the jaw from the second position to the first position when the obstructive sleep apnea event has subsided. In some embodiments the MRD includes at least one MRD motor, and reactuating the MRD includes deactivating the least one MRD motor.

Yet another embodiment of the invention may include a system to treat obstructive sleep apnea, including an ionic polymer metal composite (IPMC) sensor attached to a region in an airway passage in an oral cavity which generates an electrical output when a change in shape of the airway passage in the oral cavity occurs, a transmitter device electrically coupled to the IPMC sensor and configured to wirelessly transmit at least one electronic signal, a sensor analyzer electronically coupled to the transmitter device for receiving and analyzing the at least one electronic signal and generating an output based thereon, and a positive airway pressure machine electronically coupled to the sensor analyzer for generating an optimum input pressure to treat the sleep apnea event according to the output from the sensor analyzer. In some embodiments the output of the sensor analyzer is generated in a linear, non-linear, or adaptive fashion. In some embodiments the output generation is based on neural network algorithms. In some embodiments the IPMC sensor includes an electro active polymer material. In some embodiments the IPMC sensor is configured as an elongated strip. In some embodiments the IPMC sensor is implanted into the soft palate. In some embodiments the IPMC sensor does not include an external power source. In some embodiments the positive airway pressure machine automatically titrates an amount of pressure delivered to a patient. In some embodiments the positive airway pressure machine includes a pressure controller. In some embodiments the pressure controller is coupled to a pressure sensor which outputs a pressure signal. In some embodiments the pressure signal is also used to generate the optimum input pressure.

Yet another embodiment of the invention may include a method to treat obstructive sleep apnea, including generating at least one electronic signal from an iconic polymer metal composite (IPMC) sensor attached to a region in the in the airway passage in the oral cavity when a change in shape of the mouth or larynx occurs from an obstructive sleep apnea event, wirelessly transmitting the at least one electronic signal, receiving and analyzing the at least one electronic signal, generating an output based on the at least one electronic signal, and generating an optimum input pressure at least partially based on the output for a positive airway pressure machine to treat the obstructive sleep apnea event. In some embodiments the method additionally includes generating at least one additional electronic signal from a second ionic polymer metal composite (IPMC) sensor. In some embodiments the output is generated in a linear or non-linear or adaptive fashion. In some embodiments the output generation is based on neural network algorithms. In some embodiments the method additionally includes generating a pressure signal from a pressure sensor. In some embodiments the pressure signal is also used to generate the optimum input pressure. In some embodiments the output is the sole input to generate the optimum input pressure. In some embodiments wirelessly transmitting the at least one electronic signal is performed by a transmitter device which is integral with the IPMC sensor.

DETAILED DESCRIPTION

Devices and Methods

Figure 1:
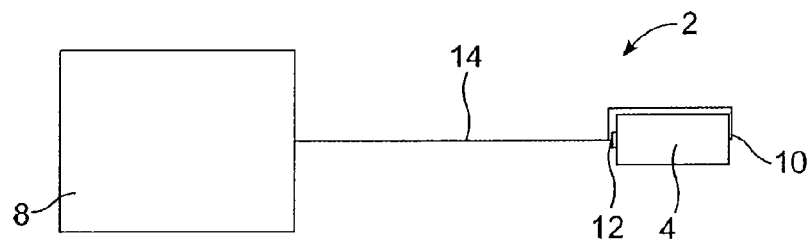
FIG. 1 illustrates one embodiment of the airway implant device.

A first aspect of the invention is a device for the treatment of disorders associated with improper airway patency, such as snoring or sleep apnea. The device comprises of an actuator element to adjust the opening of the airway. In a preferred embodiment, the actuator element comprises of an electroactive polymer (EAP) element. The electroactive polymer element in the device assists in maintaining appropriate airway opening to treat the disorders. Typically, the EAP element provides support for the walls of an airway, when the walls collapse, and thus, completely or partially opens the airway.

The device functions by maintaining energized and non-energized configurations of the EAP element. In preferred embodiments, during sleep, the EAP element is energized with electricity to change its shape and thus modify the opening of the airway. Typically, in the non-energized configuration the EAP element is soft and in the energized configuration is stiffer. The EAP element of the device can have a pre-set non-energized configuration wherein it is substantially similar to the geometry of the patient's airway where the device is implanted.

In some embodiments, the device, in addition to the EAP element, includes an implantable transducer in electrical communication with the EAP element. A conductive lead connects the EAP element and the implantable transducer to the each other. The device of the present invention typically includes a power source in electrical communication with the EAP element and/or the implantable transducer, such as a battery or a capacitor. The battery can be disposable or rechargeable.

Preferred embodiments of the invention include a non-implanted portion, such as a mouthpiece, to control the implanted EAP element. The mouthpiece is typically in conductive or inductive communication with an implantable transducer. In one embodiment, the mouthpiece is a dental retainer with an induction coil and a power source. The dental retainer can further comprise a pulse-width-modulation circuit. When a dental retainer is used it is preferably custom fit for the individual biological subject. If the implantable transducer is in inductive communication, it will typically include an inductive receiver, such as a coil. The implantable transducer can also include a conductive receiver, such as a dental filling, a dental implant, an implant in the oral cavity, an implant in the head or neck region. In one embodiment, the device includes a dermal patch with a coil, circuit and power source, in communication with the implantable transducer. The dermal patch can also include a pulse-width-modulation circuit.

Another aspect of the invention is a method to modulate air flow through airway passages. Such modulation is used in the treatment of diseases such as snoring and sleep apnea. One method of the invention is a method for modulating the airflow in airway passages by implanting in a patient a device comprising an actuator element and controlling the device by energizing the actuator element. The actuator element preferably comprises an electroactive polymer element. The actuator element can be controlled with a mouthpiece inserted into the mouth of the patient. The energizing is typically performed with the use of a power source in electrical communication, either inductive communication or conductive communication, with the actuator element. A transducer can be used to energize the actuator element by placing it in electrical communication with the power source. Depending on the condition being treated, the actuator element is placed in different locations such as soft palate, airway sidewall, uvula, pharynx wall, trachea wall, larynx wall, and/or nasal passage wall.

A preferred embodiment of the device of the present invention comprises an implantable actuator element; an implantable transducer; an implantable lead wire connecting the actuator element and the transducer; a removable transducer; and a removable power source; and wherein the actuator element comprises an electroactive polymer.

Electroactive polymer is a type of polymer that responds to electrical stimulation by physical deformation, change in tensile properties, and/or change in hardness. There are several types of electroactive polymers like dielectric electrostrictive polymer, ion exchange polymer and ion exchange polymer metal composite (IPMC). The particular type of EAP used in the making of the disclosed device can be any of the aforementioned electroactive polymers.

Suitable materials for the electroactive polymer element include, but are not limited to, an ion exchange polymer, an ion exchange polymer metal composite, an ionomer base material. In some embodiments, the electroactive polymer is perfluorinated polymer such as polytetrafluoroethylene, polyfluorosulfonic acid, perfluorosulfonate, and polyvinylidene fluoride. Other suitable polymers include polyethylene, polypropylene, polystyrene, polyaniline, polyacrylonitrile, cellophane, cellulose, regenerated cellulose, cellulose acetate, polysulfone, polyurethane, polyvinyl alcohol, polyvinyl acetate, polyvinyl pyrrolidone. Typically, the electroactive polymer element includes a biocompatible conductive material such as platinum, gold, silver, palladium, copper, and/or carbon.

Suitable shapes of the electroactive polymer element include three dimensional shape, substantially rectangular, substantially triangular, substantially round, substantially trapezoidal, a flat strip, a rod, a cylindrical tube, an arch with uniform thickness or varying thickness, a shape with slots that are perpendicular to the axis, slots that are parallel to the longitudinal axis, a coil, perforations, and/or slots.

IPMC is a polymer and metal composite that uses an ionomer as the base material. Ionomers are types of polymers that allow for ion movement through the membrane. There are several ionomers available in the market and some of the suited ionomers for this application are polyethylene, polystyrene, polytetrafluoroethylene, polyvinylidene fluoride, polyfluorosulfonic acid based membranes like NAFION® (from E. I. Du Pont de Nemours and Company, Wilmington, Del.), polyaniline, polyacrylonitrile, cellulose, cellulose acetates, regenerated cellulose, polysulfone, polyurethane, or combinations thereof. A conductive metal, for example gold, silver, platinum, palladium, copper, carbon, or combinations thereof, can be deposited on the ionomer to make the IPMC. The IPMC element can be formed into many shapes, for example, a strip, rod, cylindrical tube, rectangular piece, triangular piece, trapezoidal shape, arch shapes, coil shapes, or combinations thereof. The IPMC element can have perforations or slots cut in them to allow tissue in growth.

The electroactive polymer element has, in some embodiments, multiple layers of the electroactive polymer with or without an insulation layer separating the layers of the electroactive polymer. Suitable insulation layers include, but are not limited to, silicone, polyurethane, polyimide, nylon, polyester, polymethylmethacrylate, polyethylmethacrylate, neoprene, styrene butadiene styrene, or polyvinyl acetate.

In some embodiments, the actuator element, the entire device, or portions of the airway implant have a coating. The coating isolates the coated device from the body fluids and/or tissue either physically or electrically. The device can be coated to minimize tissue growth or promote tissue growth. Suitable coatings include poly-L-lysine, poly-D-lysine, polyethylene glycol, polypropylene, polyvinyl alcohol, polyvinylidene fluoride, polyvinyl acetate, hyaluronic acid, and/or methylmethacrylate.

Embodiments of the Device

FIG. 1 illustrates an airway implant system 2 that has a power source 4, a connecting element, such as a wire lead 14, and an actuator element, such as an electroactive polymer element 8. Suitable power sources 4 are a power cell, a battery, a capacitor, a substantially infinite bus (e.g., a wall outlet leading to a power generator), a generator (e.g., a portable generator, a solar generator, an internal combustion generator), or combinations thereof. The power source 4 typically has a power output of from about 1 mA to about 5 A, for example about 500 mA.

Instead of or in addition to wire lead 14, the connecting element may be an inductive energy transfer system, a conductive energy transfer system, a chemical energy transfer system, an acoustic or otherwise vibratory energy transfer system, a nerve or nerve pathway, other biological tissue, or combinations thereof. The connecting element is made from one or more conductive materials, such as copper. The connecting element is completely or partially insulated and/or protected by an insulator, for example polytetrafluoroethylene (PTFE). The insulator can be biocompatible. The power source 4 is typically in electrical communication with the actuator element 8 through the connecting element. The connecting element is attached to an anode 10 and a cathode 12 on the power source 4. The connecting elements can be made from one or more sub-elements.

The actuator element 8 is preferably made from an electroactive polymer. Most preferably, the electroactive polymer is an ion exchange polymer metal composite (IPMC). The IPMC has a base polymer embedded, or otherwise appropriately mixed, with a metal. The IPMC base polymer is preferably perfluoronated polymer, polytetrafluoroethylene, polyfluorosulfonic acid, perfluorosulfonate, polyvinylidene fluoride, hydrophilic polyvinylidene fluoride, polyethylene, polypropylene, polystyrene, polyaniline, polyacrylonitrile, cellophane, cellulose, regenerated cellulose, cellulose acetate, polysulfone, polyurethane, polyvinyl alcohol, polyvinyl acetate and polyvinyl pyrrolidone, or combinations thereof. The IPMC metal can be platinum, gold, silver, palladium, copper, carbon, or combinations thereof.

Figure 2:
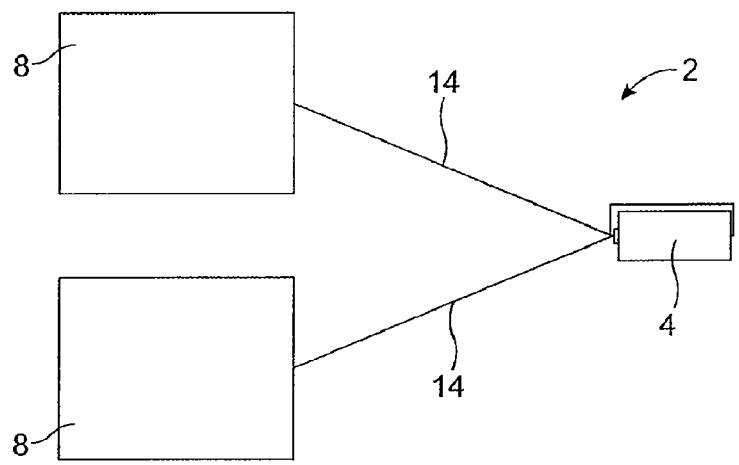
FIG. 2 illustrates one embodiment of the airway implant device.

FIG. 2 illustrates that the actuator element 8 can have multiple elements 8 and connecting elements 14 that all connect to a single power source 4.

Figure 3:
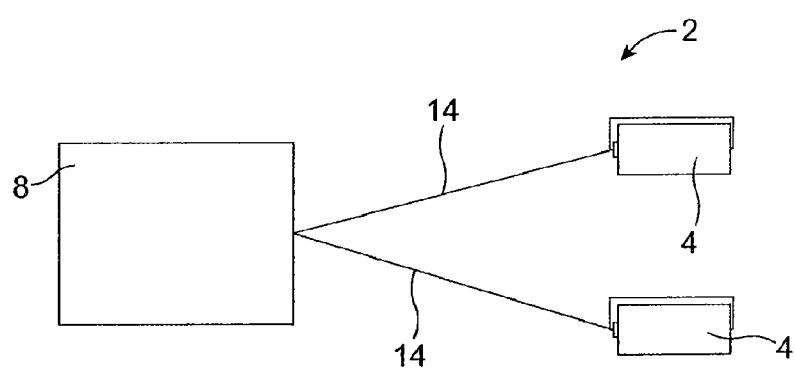
FIG. 3 illustrates one embodiment of the airway implant device.

FIG. 3 illustrates an airway implant system 2 with multiple power sources 4 and connecting elements 14 that all connect to a single actuator element 8. The airway implant system 2 can have any number and combination of actuator elements 8 connected to power sources 4.

Figure 4:
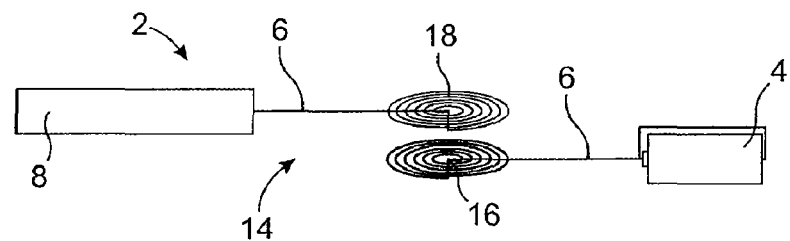
FIG. 4 illustrates one embodiment of the airway implant device.

FIG. 4 illustrates an embodiment with the connecting element having a first energy transfer element, for example a first transducer such as a first receiver, and a second energy transfer element, for example a second transducer such as a second inductor 16. In this embodiment, the first receiver is a first inductor 18. The first inductor 18 is typically positioned close enough to the second inductor 16 to enable sufficient inductive electricity transfer between the second and first inductors 16 and 18 to energize the actuator element 8. The connecting element 14 has multiple connecting elements 6.

Figure 5:
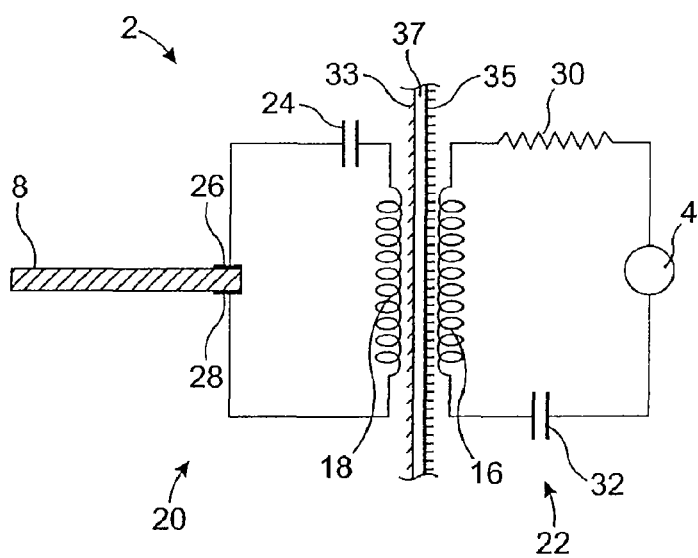
FIG. 5 illustrates a circuit diagram of an embodiment of the airway implant device.

FIG. 5 illustrates that the airway implant device of the present invention can have an implanted portion 20 and a non-implanted portion 22. In this embodiment, the implanted portion 20 is a closed circuit with the first inductor 18 in series with a first capacitor 24 and the actuator element 8. The actuator element 8 is attached to the closed circuit of the implanted portion 20 by a first contact 26 and a second contact 28. In some embodiments, the implanted portion has a resistor (not shown). The non-implanted portion 22 is a closed circuit. The non-implanted portion 22 has a second inductor 16 that is in series with a resistor 30, the power source 4, and a second capacitor 32. The capacitors, resistors, and, in-part, the inductors are representative of the electrical characteristics of the wire of the circuit and not necessarily representative of specific elements. The implanted portion 20 is within tissue and has a tissue surface 33 nearby. The non-implanted portion is in insulation material 35. An air interface 37 is between the tissue surface 33 and the insulation material 35.

Figure 6:
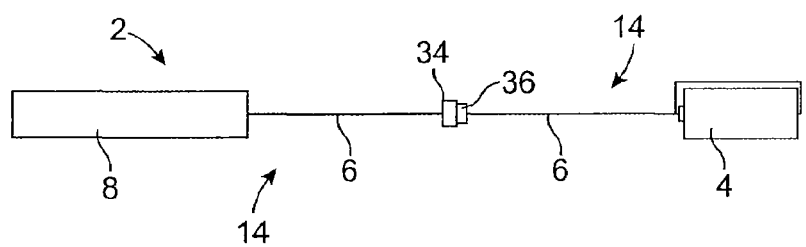
FIG. 6 illustrates an embodiment of the airway implant device.

FIG. 6 illustrates an embodiment in which the first energy transfer element of the connecting element 14 is a first conductor 34. The second energy transfer element of the connecting element 14 is a second conductor 36. The first conductor 34 is configured to plug into, receive, or otherwise make secure electrical conductive contact with the second conductor 36. The first conductor 34 and/or second conductor 36 are plugs, sockets, conductive dental fillings, tooth caps, fake teeth, or any combination thereof.

Figure 7:
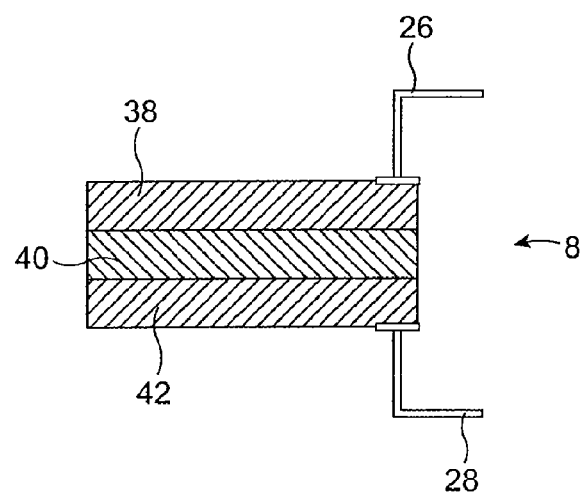
FIG. 7 illustrates a sectional view of an embodiment of the electroactive polymer element.

FIG. 7 illustrates an embodiment in which the actuator element 8 is a multi-layered device. The actuator element 8 has a first EAP layer 38, a second EAP layer 40, and a third EAP layer 42. The EAP layers 38, 40 and 42 are in contact with each other and not separated by an insulator.

Figure 8:
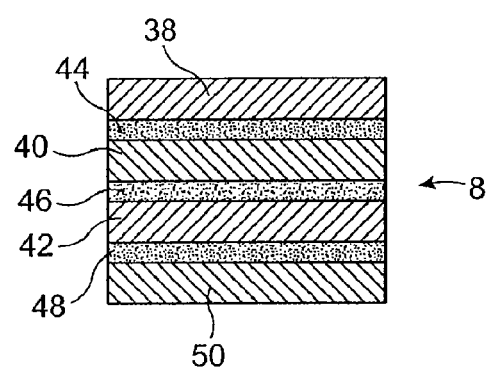
FIG. 8 illustrates a sectional view of an embodiment of the electroactive polymer element.

FIG. 8 illustrates another embodiment in which the actuator element 8 has a first EAP layer 38 separated from a second EAP layer 40 by a first insulation layer 44. A second insulation layer 46 separates the second EAP layer from the third EAP layer 42. A third insulation layer 48 separates the third EAP layer from the fourth EAP layer 50. Insulation material is preferably a polymeric material that electrically isolates each layer. The insulation can be, for example, acrylic polymers, polyimide, polypropylene, polyethylene, silicones, nylons, polyesters, polyurethanes, or combinations thereof. Each EAP layer, 38, 40, 42 and 50 can be connected to a lead wire (not shown). All anodes and all cathodes are connected to the power source 4.

Figure 9:
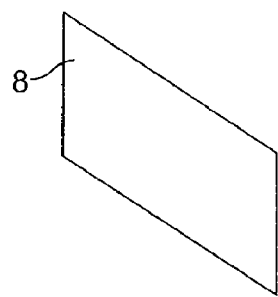
FIG. 9 illustrates an embodiment of the electroactive polymer element.
Figure 10:
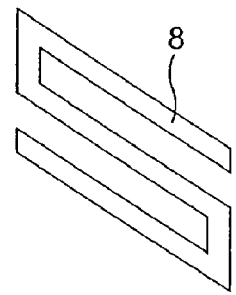
FIG. 10 illustrates an embodiment of the electroactive polymer element.
Figure 11:
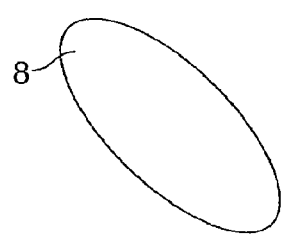
FIG. 11 illustrates an embodiment of the electroactive polymer element.
Figure 12:
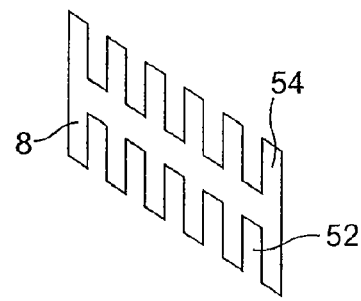
FIG. 12 illustrates an embodiment of the electroactive polymer element.
Figure 13:
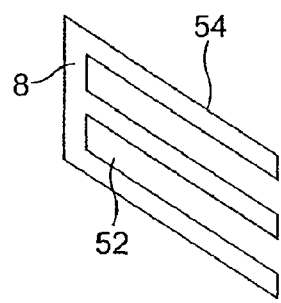
FIG. 13 illustrates an embodiment of the electroactive polymer element.
Figure 14:
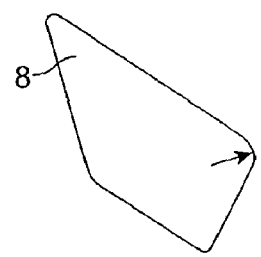
FIG. 14 illustrates an embodiment of the electroactive polymer element.
Figure 15:
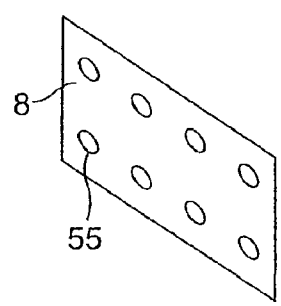
FIG. 15 illustrates an embodiment of the electroactive polymer element.
Figure 16:
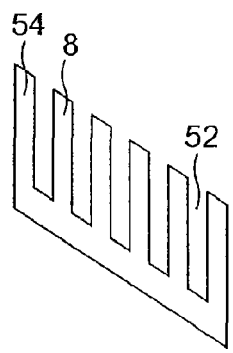
FIG. 16 illustrates an embodiment of the electroactive polymer element.
Figure 17:
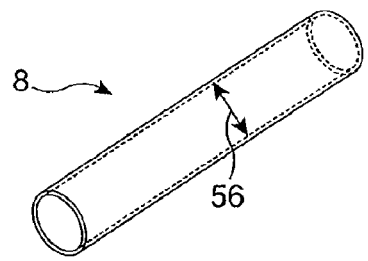
FIG. 17 illustrates an embodiment of the electroactive polymer element.
Figure 18:
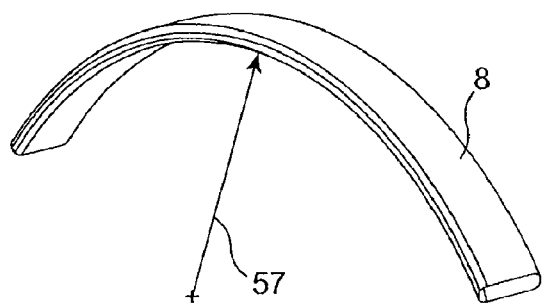
FIG. 18 illustrates an embodiment of the electroactive polymer element.
Figure 19:
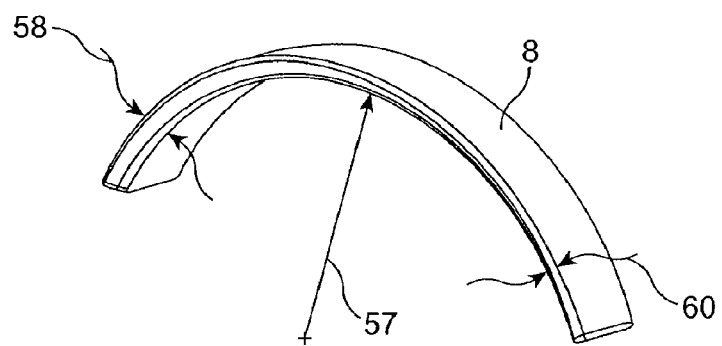
FIG. 19 illustrates an embodiment of the electroactive polymer element.

FIGS. 9-19 illustrate different suitable shapes for the actuator element 8. FIG. 9 illustrates a actuator element 8 with a substantially flat rectangular configuration. The actuator element 8 can have a width from about 2 mm to about 5 cm, for example about 1 cm. FIG. 10 illustrates an actuator element 8 with an "S" or zig-zag shape. FIG. 11 illustrates the actuator element 8 with an oval shape. FIG. 12 illustrates a actuator element 8 with a substantially flat rectangular shape with slots 52 cut perpendicular to the longitudinal axis of the actuator element 8. The slots 52 originate near the longitudinal axis of the actuator element 8. The actuator element 8 has legs 54 extending away from the longitudinal axis. FIG. 13 illustrates an actuator element 8 with slots 52 and legs 54 parallel with the longitudinal axis. FIG. 14 illustrates an actuator element be configured as a quadrilateral, such as a trapezoid. The actuator element 8 has chamfered corners, as shown by radius. FIG. 15 illustrates an actuator element 8 with apertures 55, holes, perforations, or combinations thereof. FIG. 16 illustrates an actuator element 8 with slots 52 and legs 54 extending from a side of the actuator element 8 parallel with the longitudinal axis. FIG. 17 illustrates an actuator element 8 with a hollow cylinder, tube, or rod. The actuator element has an inner diameter 56. FIG. 18 illustrates an arched actuator element 8. The arch has a radius of curvature 57 from about 1 cm to about 10 cm, for example about 4 cm. The actuator element 8 has a uniform thickness. FIG. 19 illustrates an arched actuator element 8. The actuator element 8 can have a varying thickness. A first thickness 58 is equal or greater than a second thickness 60.

Figure 20:
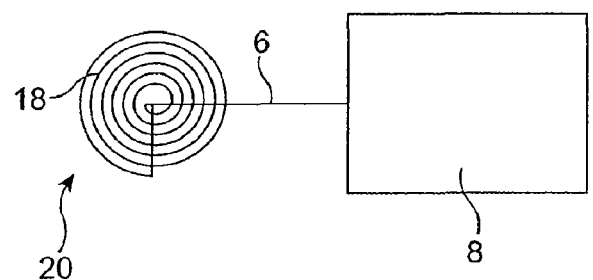
FIG. 20 illustrates an embodiment of the implanted portion of the airway implant device.
Figure 21:
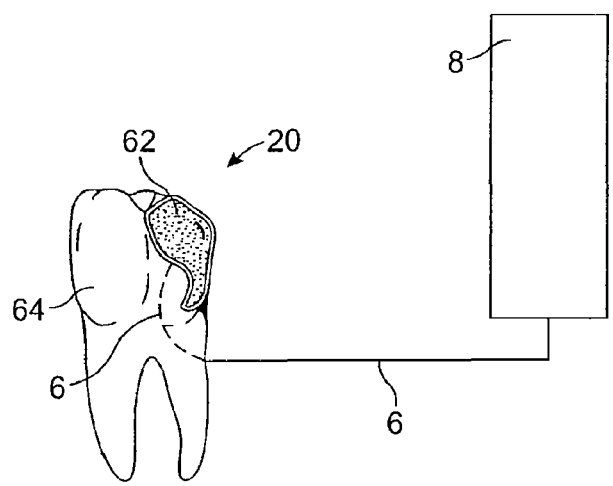
FIG. 21 illustrates an embodiment of the airway implant device.

FIG. 20 illustrates an embodiment of the implanted portion of an airway implant with a coil-type inductor 18 connected by a wire lead 6 to the actuator element 8. In another embodiment, as illustrated in FIG. 21 the implanted portion has a conductive dental filling 62 in a tooth 64. The dental filling 62 is previously implanted for reasons related or unrelated to using of the airway implant system. The dental filling 62 is electrically connected to the wire lead 6. For example, a portion of the wire lead 6 is implanted in the tooth 64, as shown by phantom line. The wire lead 6 is connected to the actuator element 8.

Figure 22:
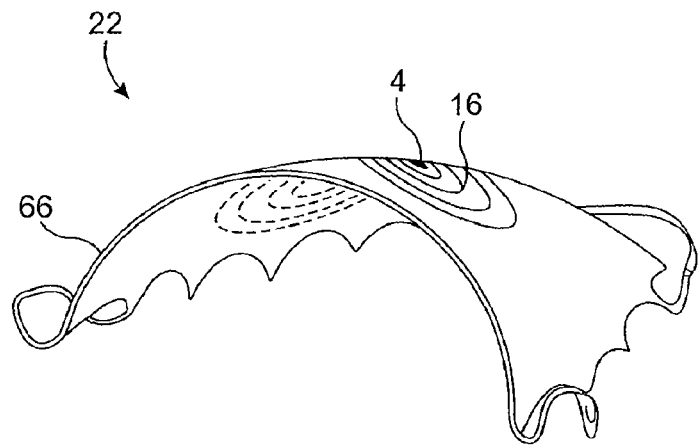
FIG. 22 illustrates an embodiment of the non-implanted portion in the form of a mouth guard.
Figure 23:
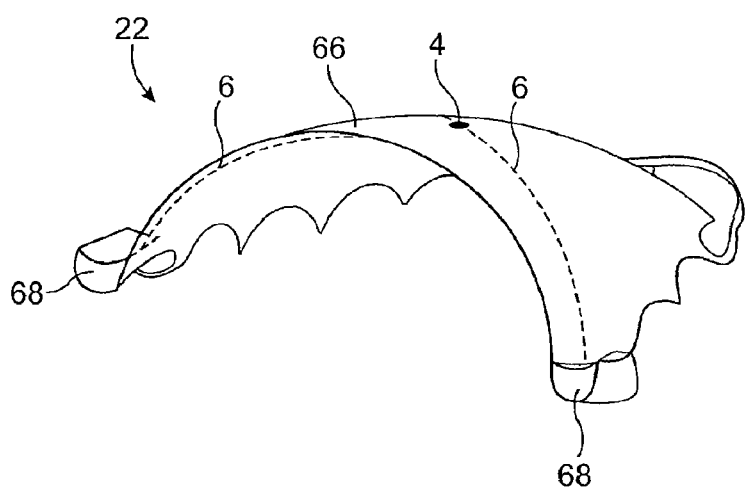
FIG. 23 illustrates an embodiment of the non-implanted portion in the form of a mouth guard.
Figure 24:
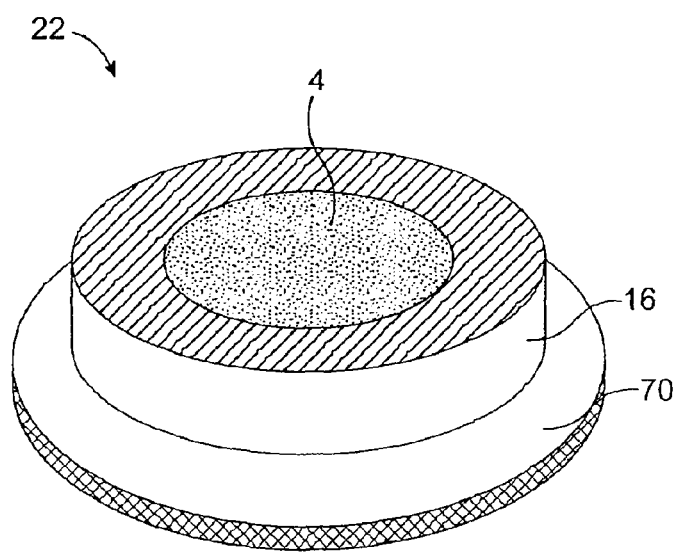
FIG. 24 illustrates an embodiment of the non-implanted portion.

FIG. 22 illustrates an embodiment of the non-implanted portion 22 with a mouthpiece, such as a retainer 66. The retainer 66 is preferably custom configured to fit to the patient's mouth roof, or another part of the patient's mouth. The second transducer, such as second inductor 16, is integral with, or attached to, the retainer 66. The second inductor 16 is located in the retainer 66 so that during use the second inductor 16 is proximal with the first inductor 18. The power source 4, such as a cell, is integral with, or attached to, the retainer 66. The power source 4 is in electrical communication with the second inductor 16. In some embodiments, the retainer 66 has a pulse-width-modulation circuit. FIG. 23 illustrates that the retainer 66 has one or more tooth sockets 68. The tooth sockets 68 are preferably configured to receive teeth that have dental fillings. The tooth sockets 68 are electrically conductive in areas where they align with dental fillings when in use. The power source 4 is connected with the tooth sockets 68 via the wire leads 6. In the embodiment of FIG. 24, the non-implantable portion 22 has the second inductor 16 attached to a removably attachable patch 70. The patch 70 is attached to the power source 4. The power source 4 is in contact with the second inductor 16. This embodiment can be, for example, located on the cheeks as shown on FIG. 33 or any other suitable location.

Figure 30:
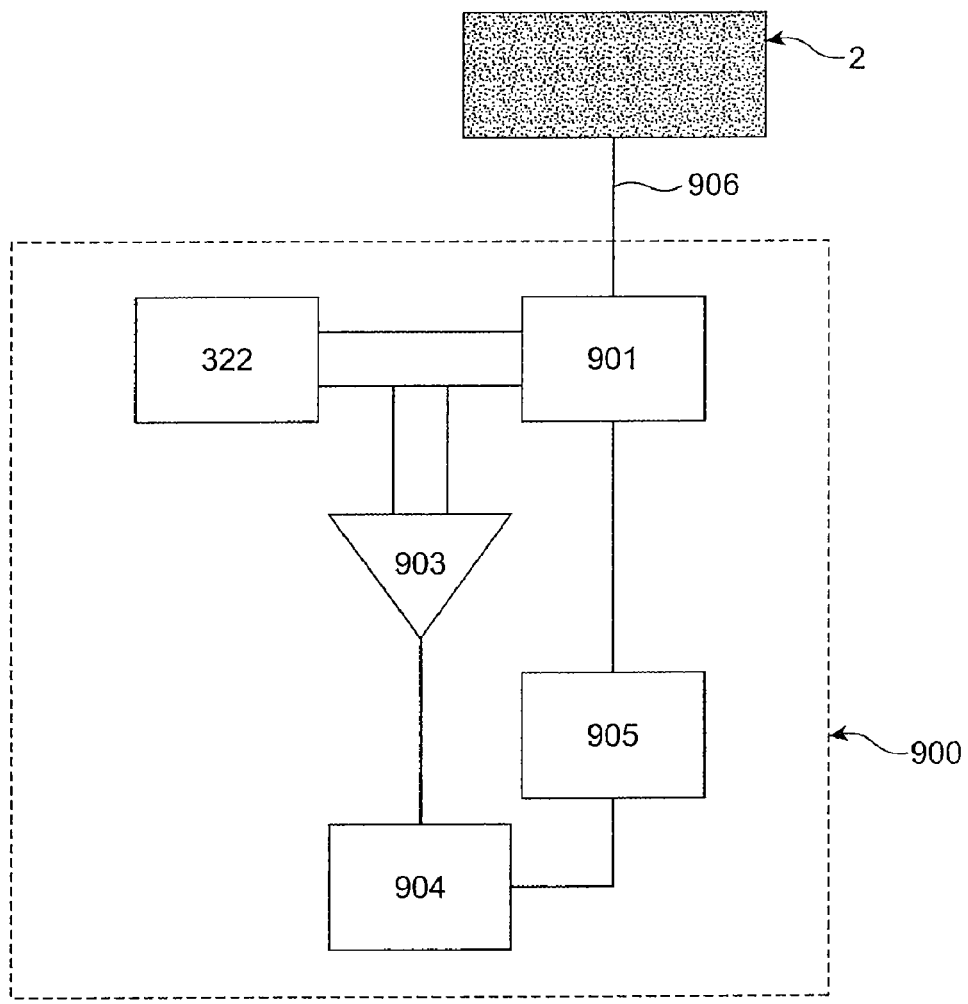
FIG. 30 illustrates an embodiment of an inductive coupling system associated with the airway implant device.

Preferably, the airway implant device 2 discussed herein is used in combination with an inductive coupling system 900 such as depicted in FIG. 30. FIG. 30 depicts an inductive coupling system that is suitable for controlling the airway implant device 2 which includes a connecting element 906 (which connects the electrical contacts (not shown) to the rest of the electrical system), a connector 901, a energy source 322, a sensor 903, a timer 904, and a controller 905. The connector 901, energy source 322, sensor 903, a timer 904, and controller 905 are located in a housing disposed in a region outside or inside the body.

Figure 31:
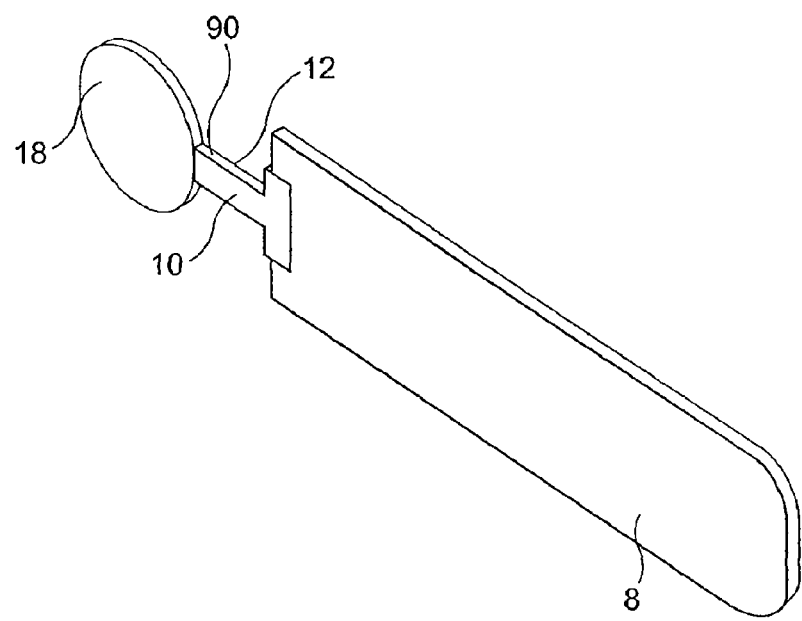
FIG. 31 illustrates an embodiment of the airway implant device.
Figure 32:
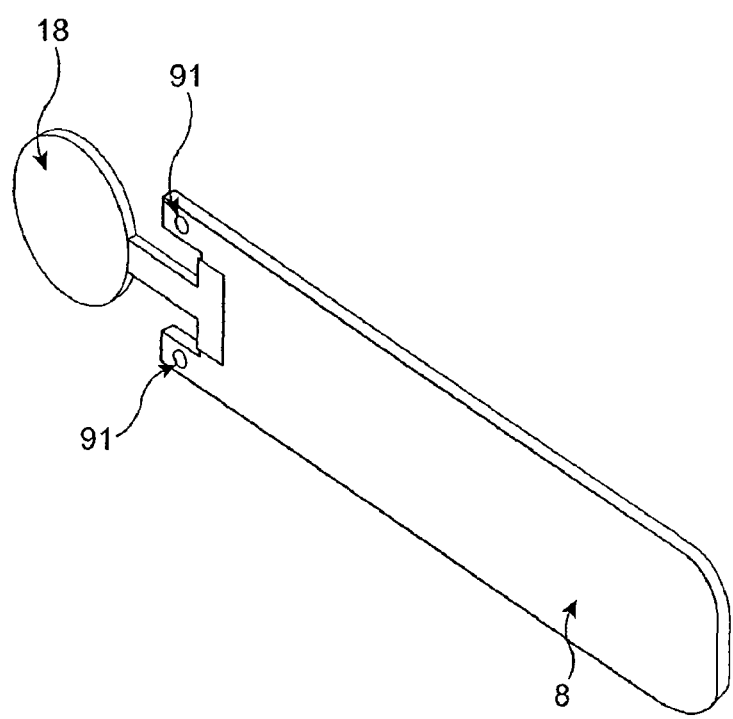
FIG. 32 illustrates an embodiment of the airway implant device.

Two preferred embodiments of the airway implant device are shown in FIGS. 31 and 32. The device in FIG. 31 includes the actuator element 8 connected to an anode 10 and cathode 12 and to the induction coil 18. The device also includes a controller 90, such as a microprocessor. The circuitry within the controller is not shown. The controller 90 picks up AC signals from the induction coil 18 and converts it to DC current. The controller 90 can also include a time delay circuit and/or a sensor. The sensor could sense the collapsing and/or narrowing of the airways and cause the device to energize the actuator element 8 and thus completely or partially open up the airway in which the device is implanted. FIG. 32 shows an embodiment with anchors 91 located on the actuator element 8. The implant can be anchored in a suitable location with the use of these anchors and sutures and/or surgical glue.

Figure 42:
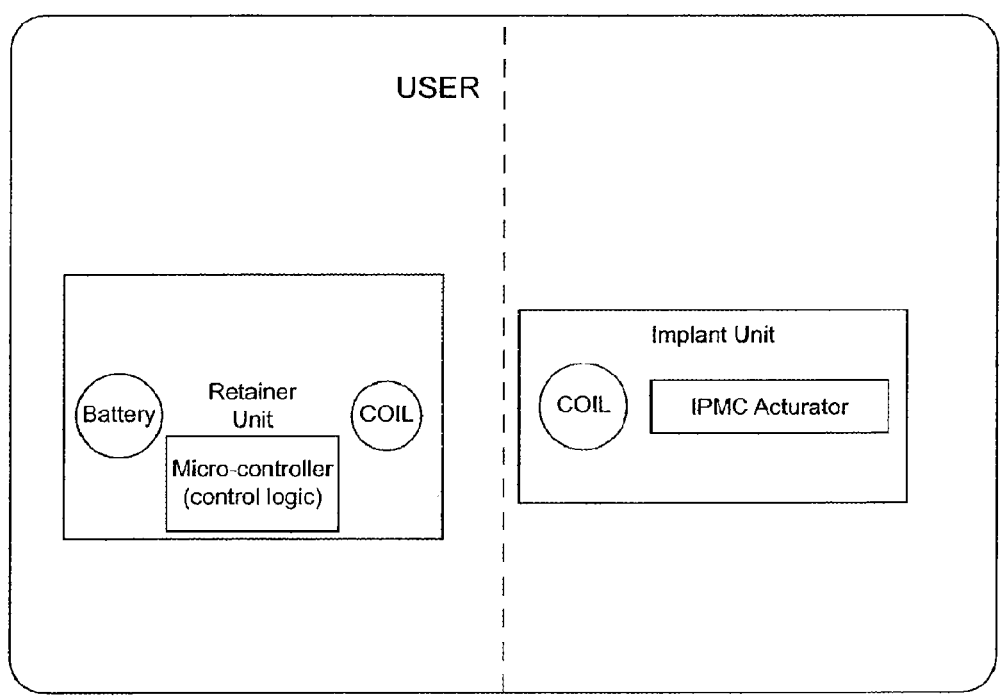
FIG. 42 depicts an embodiment of an airway implant device.

FIG. 42 depicts an embodiment of the invention. The airway implant device comprises of two units—an implant unit and a retainer unit. The implant unit is implanted in a patient and includes an IPMC actuator and a coil. The retainer unit is typically not implanted in the patient and can be worn by the patient prior to going to bed. This unit includes a coil, a battery, and a microcontroller.

Figure 43A:
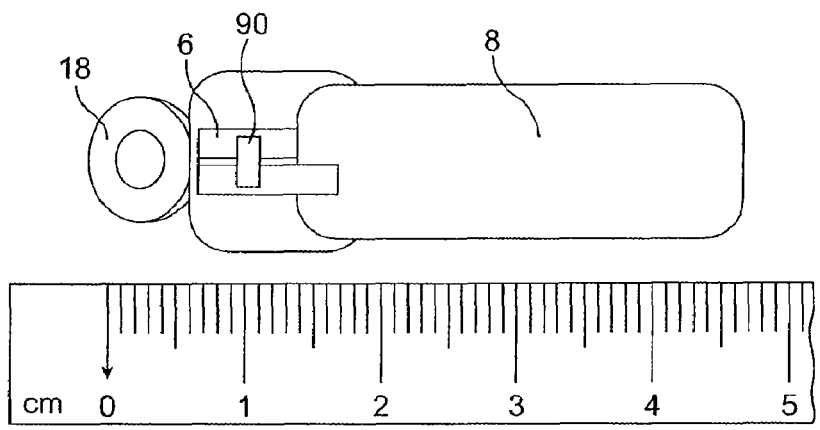
FIG. 43 depicts an embodiment of an airway implant device.
Figure 43B:
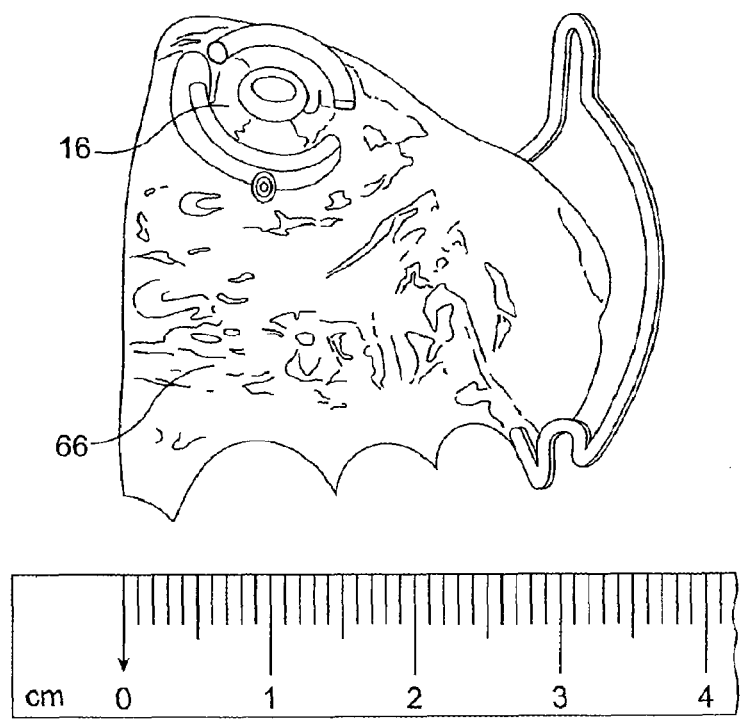

FIG. 43 depicts yet another embodiment of the invention. FIG. 43A is the implant unit, preferably for implantation proximal to or in an airway wall. The implant unit includes an actuator element 8, an inductor 18 in the form of a coil, a controller 90, and connecting elements 6. FIG. 43B depicts the removable retainer with an inductor 16 and a retainer 66.

Figure 44A:
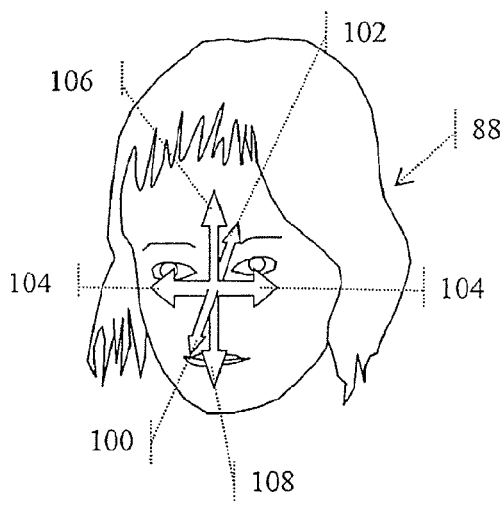
FIGS. 44A, 44B, and 44C illustrate terms used in describing the anatomy of a patient and orientation attributes of the invention.
Figure 44B:
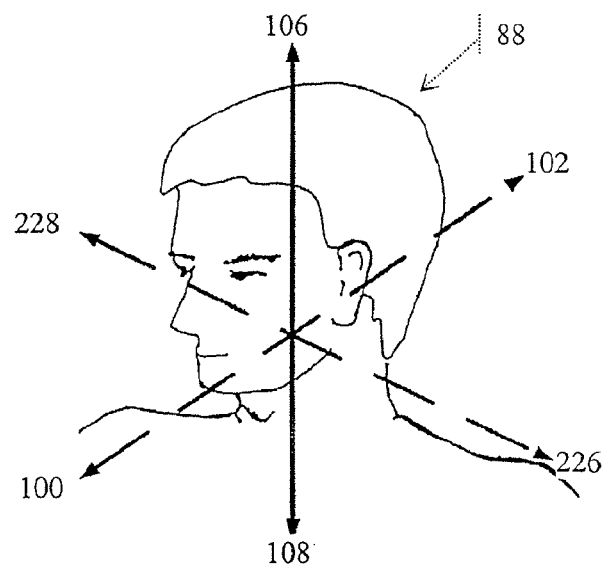
Figure 44C:
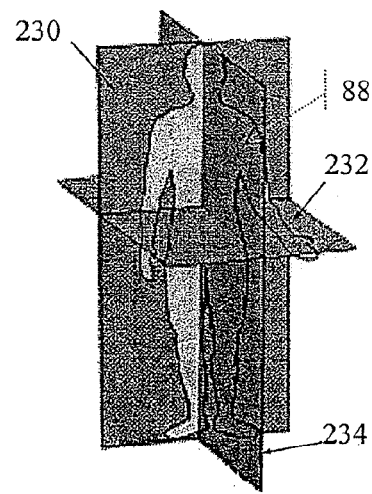

FIGS. 44A, 44B, and 44C illustrate terms used in describing the anatomy of a patient 88 and orientation attributes of the invention. Anterior 100 refers to a part of the body or invention toward the front of the body or invention, or in front of another part of the body or invention. Posterior 102 refers to a part of the invention or body toward the back of the invention or body, or behind another part of the invention or body. Lateral 104 refers to a part of the invention or body to the side of the invention or body, or away from the middle of the invention or body or the middle of the invention or body. Superior 106 refers to a part of the invention or body toward the top of the invention or body. Inferior 108 refers to a part of the invention or body toward the bottom of the invention or body. FIG. 44B illustrates the left 226 and the right 228 sides of a patient anatomy. Various planes of view are illustrated in FIG. 44C, including a coronal plane 230, a transverse plane 232, and a sagittal plane 230.

A preferred embodiment of the device of the present invention comprises an implanted portion 20 comprising an implantable actuator element 8, a housing 112, a first inductor 18, and connecting elements 14 connecting the actuator element 8 to the first inductor 18 within the housing 112; and a non-implanted portion 22 comprising a power source 4 and a second inductor 16 capable of transferring energy to the first inductor 18, wherein the energy of the first inductor 18 energizes the actuator element 8 wherein the actuator element 8 comprises an electroactive polymer element. In a preferred embodiment, the actuator element 8 of the device is implanted in the soft palate 84. The housing 112 of the preferred embodiment is implanted inferior to the hard palate 74. In a preferred embodiment of the device, the housing 112 comprises at least one of acrylic, polytetrafluoroethylene (PTFE), polymethylmethacrylate (PMMA), Acrylonitrile Butadiene Styrene (ABS), polyurethane, polycarbonate, cellulose acetate, nylon, and a thermoplastic or thermosetting material.

In a preferred embodiment, the non-implanted portion 22 is in the form of a mouth guard or dental retainer 66. In a preferred embodiment, the non-implanted portion comprises a non-implantable wearable element. In some embodiments, the superior side of the housing 112 comports to the shape of a hard palate 74. In some embodiments, the housing 112 is cast from an impression of a hard palate 74. In still other embodiments, the housing 112 is concave on its superior side. In some embodiments, the housing 112 is convex on its superior side. In some embodiments, the housing 112 comprises bumps 114 on its superior side lateral to a central axis extending from the housing's 112 anterior to its posterior end. In some embodiments, the housing 112 configuration has a substantially smooth rounded superior side. Other configurations for the housing 112 may be contemplated by one having skill in the art without departing from the invention.

In some embodiments, the actuator element 8 is at least partially within the housing 112. In other embodiments, the actuator element 8 is outside the housing 112. The housing 112 is capable of housing and protecting the first inductor 18 and connecting elements 14 between the first inductor 18 and the actuator element 8. In some embodiments, the housing 112 has a roughened surface to increase friction on the housing 112. In some embodiments, the roughened surface is created during casting of the housing 112. In some embodiments, the roughened surface induces fibrosis.

Figure 45A:
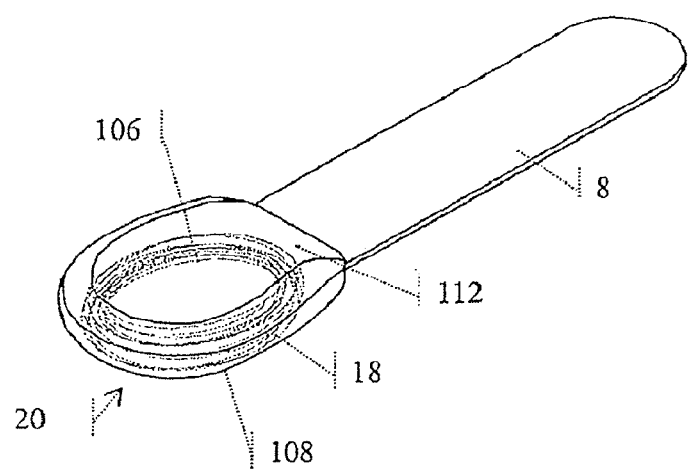
FIG. 45A illustrates an embodiment of the airway implant device.
Figure 45B:
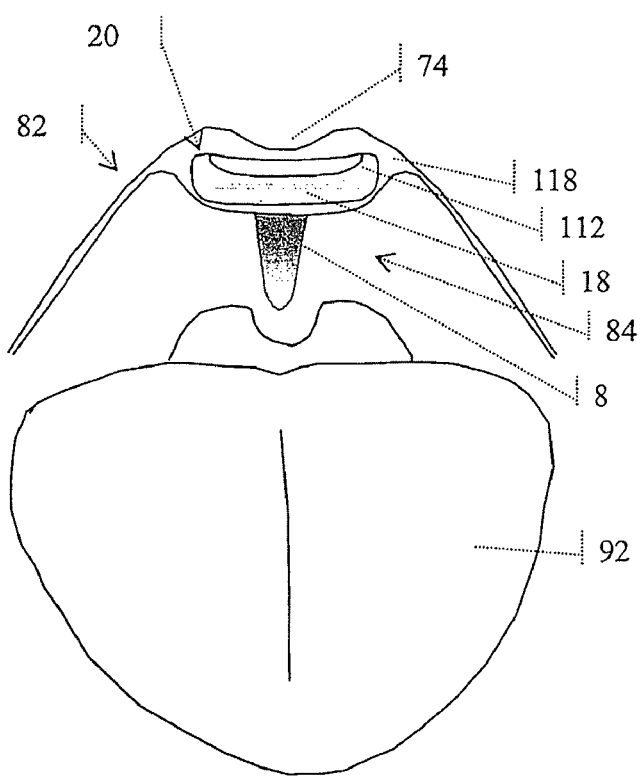
FIG. 45B illustrates the airway implant device of FIG. 45A, viewed from the anterior side of the implant, looking toward the posterior end, wherein the implant device is implanted in the palate.

FIG. 45A illustrates one embodiment of the airway implant device comprising a actuator element 8, a first inductor 18, and a housing 112 made from an acrylic and cast with substantially smooth rounded superior and anterior sides. In this embodiment, the actuator element 8 anterior end terminates at about the posterior end of the acrylic housing 112. FIG. 45B illustrates the implant device of FIG. 45A viewed from the anterior side of the implant device, looking toward the posterior end, wherein the implant device is implanted in the palate 116. In the embodiment shown in FIG. 45B, the implant device is implanted such that the housing 112 is in the periosteum 118 inferior to the ridge of the hard palate 74, and the actuator element 8 extends into the soft palate 84.

Figure 46A:
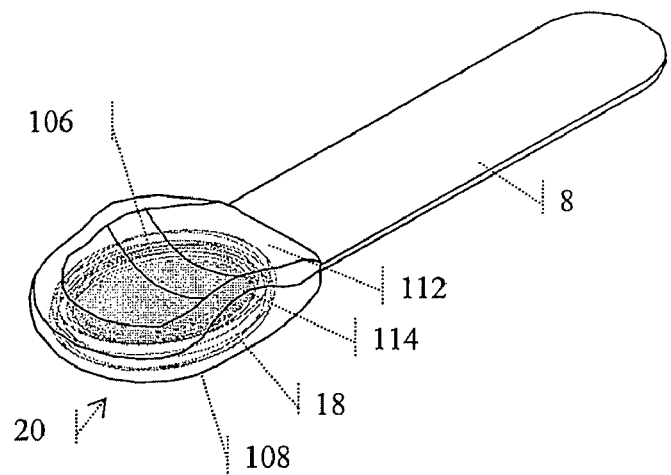
FIG. 46A illustrates an embodiment of the airway implant device.
Figure 46B:
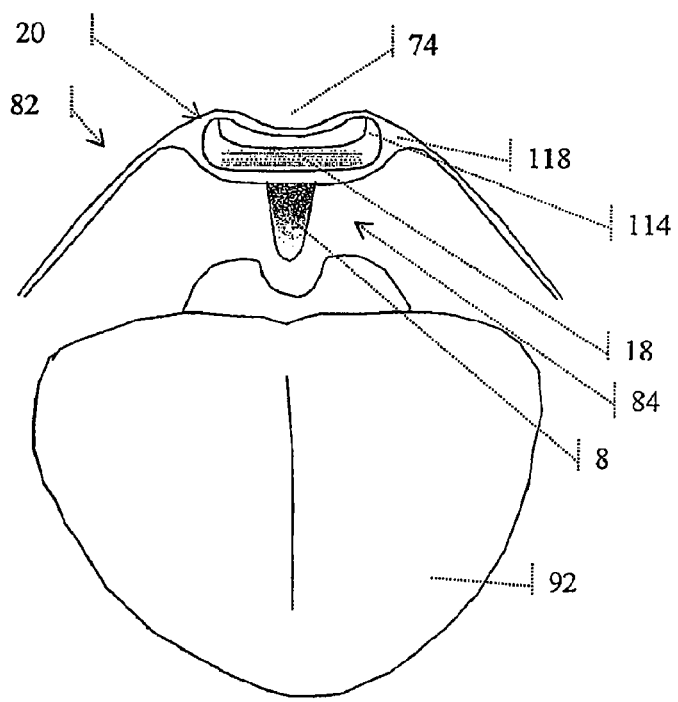
FIG. 46B illustrates the airway implant device of FIG. 46A, viewed from the anterior side of the implant, looking toward the posterior end, wherein the implant device is implanted in the palate.

FIG. 46A illustrates an embodiment of the airway implant device that has a actuator element 8, a first inductor 18, and a housing 112 with a smooth rounded inferior side, and at least two bumps 114 on its superior side which, when implanted, comport with the lateral sides of the ridge of the hard palate 74, as shown in FIG. 46B. This configuration reduces rocking of the implant device on the ridge of the hard palate 74 when implanted. In this embodiment, the actuator element 8 anterior end terminates at about the posterior end of the acrylic housing 112. FIG. 46B illustrates the airway implant device of FIG. 46A, viewed from the anterior side of the implant, looking toward the posterior end, wherein the implant device is implanted in the palate 116. In the embodiment shown in FIG. 46B, the implant device is implanted such that the housing 112 is in the periosteum 118 inferior to the ridge of the hard palate 74, and the actuator element 8 extends into the soft palate 84.

Figure 47A:
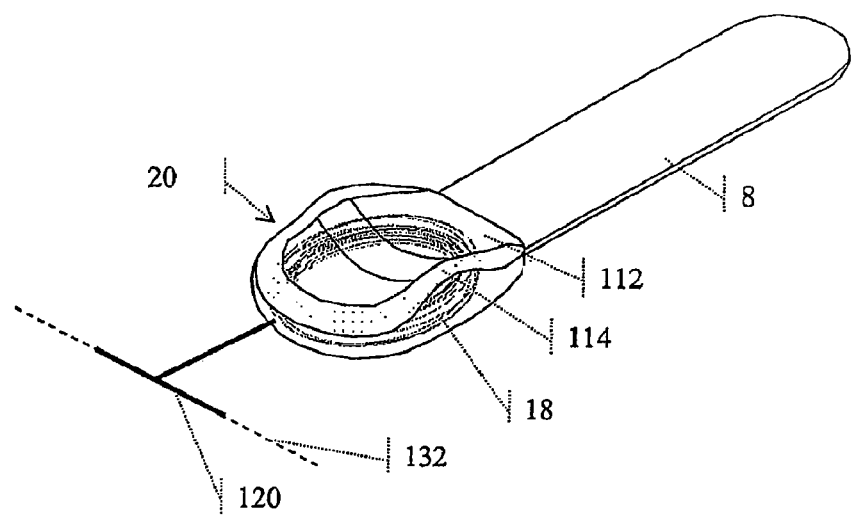
FIG. 47A illustrates an embodiment of the airway implant device with a T-shaped attachment element.

FIG. 47A illustrates an embodiment of the airway implant device having an attachment element 120 at the anterior end of the implant. In this embodiment, the attachment element 120 is T-shaped, however, other configurations and geometries of the attachment element 120 are contemplated in other embodiments, including triangular, circular, L-shaped, Z-shaped, and any geometry within the contemplation of one skilled in the art that would allow attachment of the attachment element to tissue at the anterior end of the implant to fix the position of the implant within the implant cavity.

In some embodiments of the airway implant device having attachment elements 120, the attachment element 120 is a bioabsorbable material. Examples of bioabsorbable materials include, but are not limited to, polylactic acid, polyglycolic acid, poly(dioxanone), Poly(lactide-co-glycolide), polyhydroxybutyrate, polyester, poly(amino acid), poly(trimethylene carbonate) copolymer, poly (ϵ-caprolactone) homopolymer, poly (ϵ-caprolactone) copolymer, polyanhydride, polyorthoester, polyphosphazene, and any bioabsorbable polymer.

Figure 47B:
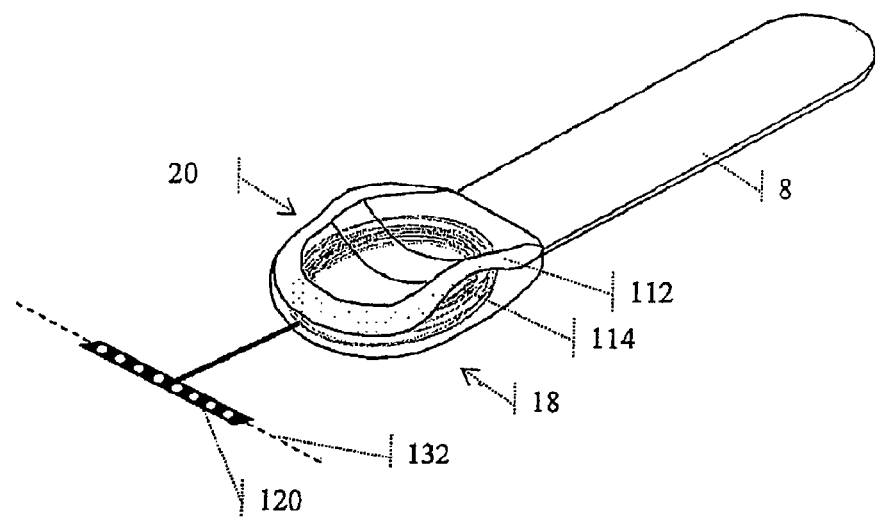
FIG. 47B illustrates an embodiment of the airway implant device with a perforated attachment element.

In another embodiment, the airway implant device comprises an attachment element 120, as shown in FIG. 47B wherein the perforated attachment element 120 comprises at least one hole 122. The hole provides a means for a suture or other attaching device to affix the device to tissue and secure the implant device position. In the case where a suture 132 is used, the suture may or may not be the same suture used by a practitioner to close the original incision made to create a cavity for the implant. The attaching device comprises at least one of a suture, clip, staple, tack, and adhesive.

In some embodiments, the implant may be secured in place, with or without use of an attachment element 120, using an adhesive suitable for tissue, such as cyanoacrylates, and including, but not limited to, 2-octylcyanoacrylate, and N-butyl-2-cyanoacrylate.

Figure 48A:
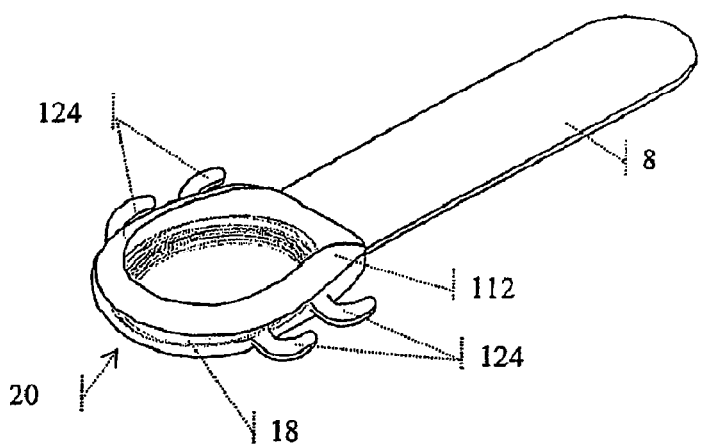
FIG. 48 illustrates an embodiment of the airway implant device with saw-blade like directional attachment element.
Figure 48B:
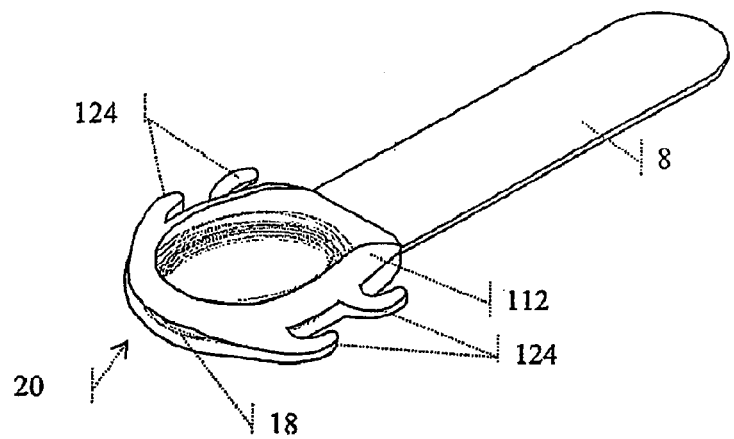

FIG. 48 illustrates an embodiment of the airway implant device wherein the housing 112 has at least one anchor 124. In FIG. 48, the device has four saw-blade like directional anchors 124. The anchors 124 may or may not be made of made of the same materials as the housing 112. Such materials include at least one of acrylic, polytetrafluoroethylene (PTFE), polymethylmethacrylate (PMMA), Acrylonitrile Butadiene Styrene (ABS), polyurethane, polycarbonate, cellulose acetate, nylon, and a thermoplastic material. In some embodiments, the device has at least one anchor 124. In some embodiments, the anchor 124 is configured to allow delivery and removal of the implant device with minimal tissue damage. In some embodiments, the anchor 124 is curved. In some embodiments the superior side(s) of the anchor(s) 124 comport with the hard palate 74 surface. In other embodiments, the superior side(s) of the anchor(s) 124 conform to the configuration of the housing 112, options for which are as described elsewhere in this disclosure.

Figure 49:
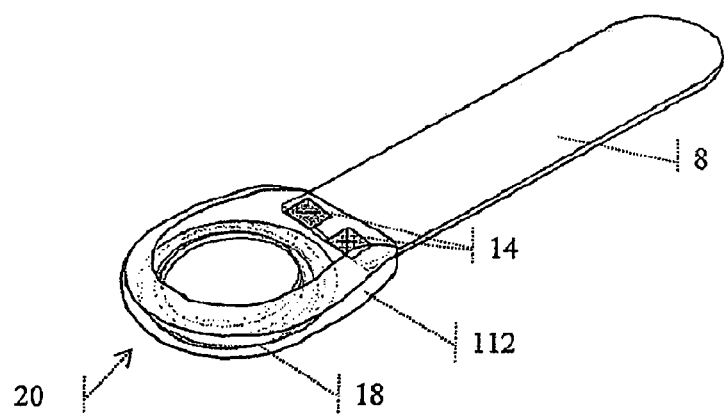
FIG. 49 illustrates an embodiment of the airway implant device with power connecting element.

FIG. 49 illustrates a preferred embodiment of the airway implant device wherein the implanted portion 20 comprises power connecting elements 14 comprising a first contact 26 and a second contact 28. In this embodiment, the first contact 26 and second contact 28 have opposing electrical charges, and the housing 112 encases the contacts. In the embodiment shown, the first contact 26 faces in the inferior direction, while the second contact 28 faces in the superior direction. In other embodiments, the first contact 26 faces in the superior direction while the second contact 28 faces in the inferior direction. In some embodiments, the connecting element 14 comprises a non-corrosive conductive material. In some embodiments, the connecting element 14 comprises platinum, gold, silver, stainless steel, or conductive carbon. In some embodiments, the connecting element 14 comprises stainless steel or copper plated with gold, platinum, or silver. In some embodiments, the actuator element 8 stiffens in one direction when a charge is applied to the connecting element 14. In some embodiments, the actuator element 8 deflects when a charge is applied to the connecting element 14.

Figure 50:
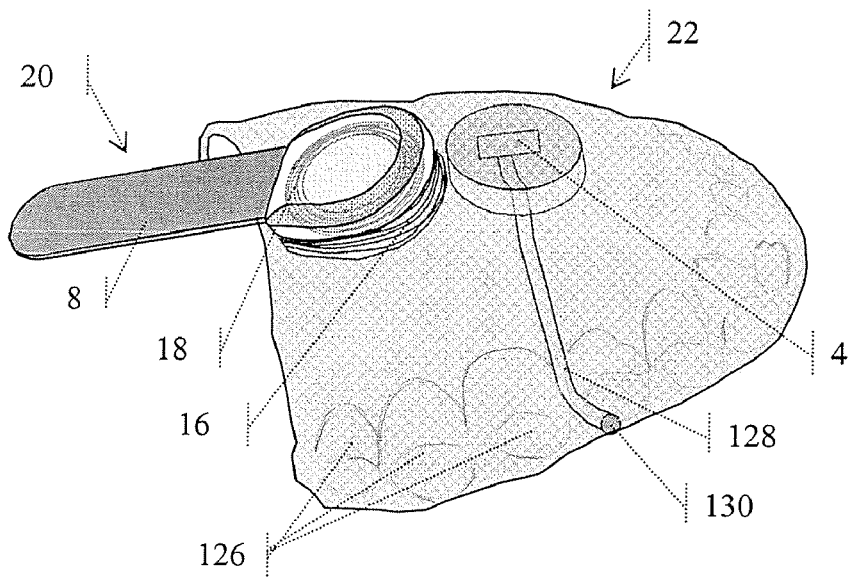
FIG. 50 illustrates an embodiment of the airway implant system with both an implantable device and a non-implantable wearable element.

FIG. 50 illustrates an embodiment of the airway implant system wherein the device comprises a non-implanted portion 22 in the form of, and made from similar material as a dental retainer 66. The retainer 66 depicted in FIG. 50 has teeth impressions 126 corresponding to a patient's approximate or exact dentition. Example dental retainer materials include acrylate, polymethylmethacrylate (PMMA), polycarbonate, and nylon. In the embodiment shown in FIG. 50, the non-implanted portion comprises a power source 4 that is rechargeable, a second inductor 16 connected to the power source 4, and ball clamps 128 having two exposed portions 130, said ball clamps 128 connected to the rechargeable power source 4, whereby the exposed portions 130 can recharge the power source 4. The exposed portions 130 are at least partially not covered by retainer material, and are thereby exposed. In the embodiment shown in FIG. 50, the non-implanted portion second inductor 16 transfers energy it receives from the power source 4 to the first inductor 18 of the implanted portion 20, wherein the first inductor 18 energizes the actuator element 8.

In some embodiments, the non-implanted portion 22 does not include ball clamps 128 for recharging the power source 4. In some embodiments, the power source 4 is a rechargeable battery. In some embodiments, the power source 4 is one of a lithium-ion battery, lithium-ion polymer battery, a silver-iodide battery, lead acid battery, a high energy density, or a combination thereof. In some embodiments, the power source 4 is removable from the non-implanted portion 22. In some embodiments, the power source 4 is replaceable. In some embodiments, the power source is designed to be replaced or recharged per a specified time interval. In some embodiments, replacing or recharging the power source 4 is necessary no more frequently than once per year. In other embodiments, replacing or recharging the power source 4 is necessary no more frequently than once every six months. In yet other embodiments, replacing or recharging the power source 4 is necessary no more frequently than once or every three months. In yet another embodiment, daily replacing or recharging of the power source is required.

In some embodiments, the power source 4 and second inductor 16 are sealed within the non-implanted portion and the sealing is liquid proof.

Figure 51A:
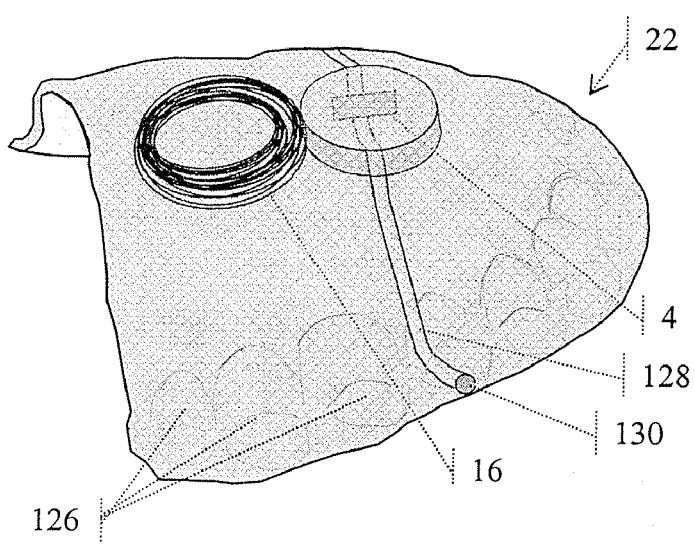
FIG. 51A illustrates an isometric view of the wearable element.
Figure 51B:
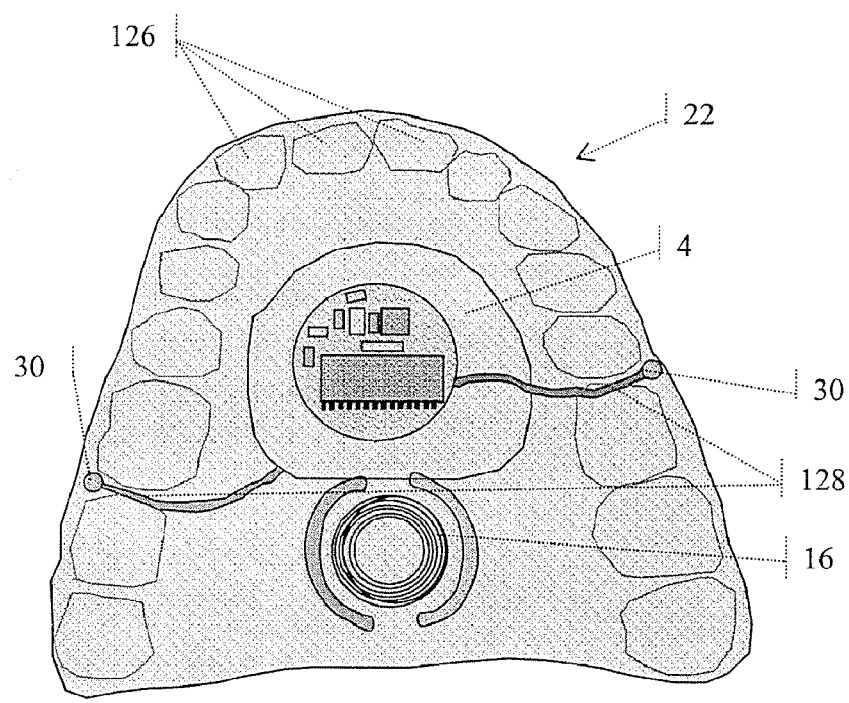
FIG. 51B illustrates a bottom view of the wearable element.

FIGS. 51A, and 51B illustrate different views of an embodiment of the airway implant device non-implanted portion 22 in the form of a retainer 66. In the embodiment depicted, the non-implanted portion 22 comprises a second inductor 16, a power source 4, and at least one balldclamp 128 for recharging the power source 4.

Figure 52:
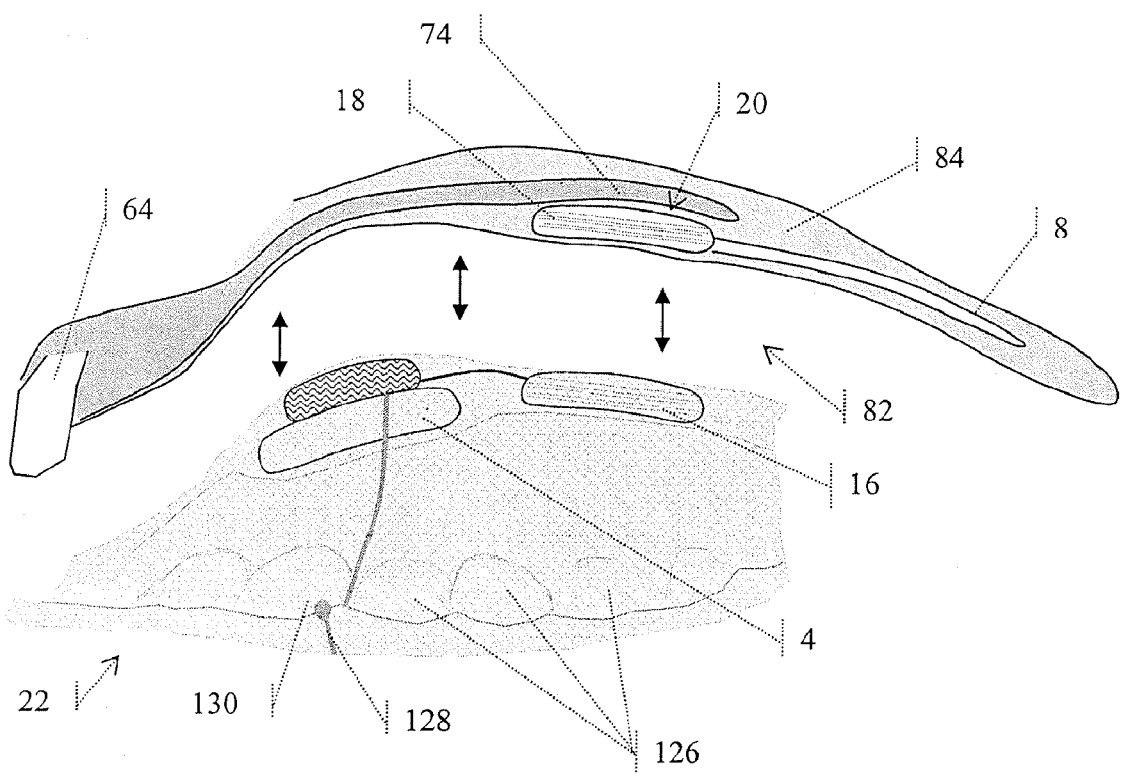
FIG. 52 illustrates a cross-sectional view of the airway implant system in the patient soft palate.

FIG. 52 illustrates an embodiment of the airway implant device implanted in the palate 116. In this embodiment, the housing 112 is implanted inferior to the hard palate 74, whereas the actuator element 8 extends posterior to the housing 112 into the soft palate 84. The non-implanted portion 22 in this embodiment comprises a retainer 66, a power source 4, a second inductor 16, and ball clamps 128 for recharging the power source 4. Other embodiments may comprise none, or some, or all of these elements (the retainer 66, power source 4, second inductor 16, and ball clamps 128), and instead open the airway by means described elsewhere in this specification. In the embodiment depicted in FIG. 52, when the implanted portion 20 of the airway implant device is implanted such that the housing 112 is inferior to the hard palate 74, and when a patient places the retainer 66 in his mouth 82, the retainer 66 having a chargeable second inductor 16 that is positioned within the retainer 66 to align inferior to the implanted first inductor 18, the second inductor 16 transfers energy to the first inductor 18 and the first inductor 18 energizes the actuator element 8. In this embodiment, the actuator element 8 comprises an electroactive polymer (EAP) element, which, when energized by the first inductor 18, opens the airway in which the device is implanted.

The implants described herein are preferably implanted with a deployment tool. Typically, the implantation involves an incision, surgical cavitation, and/or affixing the implant.

Sensing and Actuation of Airway Implants

One embodiment of the invention is an airway implant device with a sensor for monitoring a condition prior to and/or during the occurrence of an apneic event. Preferably, the sensor monitors for blockage of an airway. The sensor senses the possible occurrence of an apneic event. This sensing of a possible apneic event is typically by sensing a decrease in the airway gap, a change in air pressure in the airway, or a change in air flow in the airway. A progressive decrease in the airway gap triggers the occurrence of an apneic event. Most preferably the sensor senses one or more events prior to the occurrence an apneic event and activates the airway implant to prevent the apneic event. In some embodiments, the airway implant device and the sensor are in the same unit. In other embodiments, the actuator element of the airway implant device is the sensor. In these embodiments, the actuator element acts as both a sensor and actuator. In yet other embodiments, the airway implant device and the sensor are in two or more separate units.

Figures 37A, 37B, 37C:
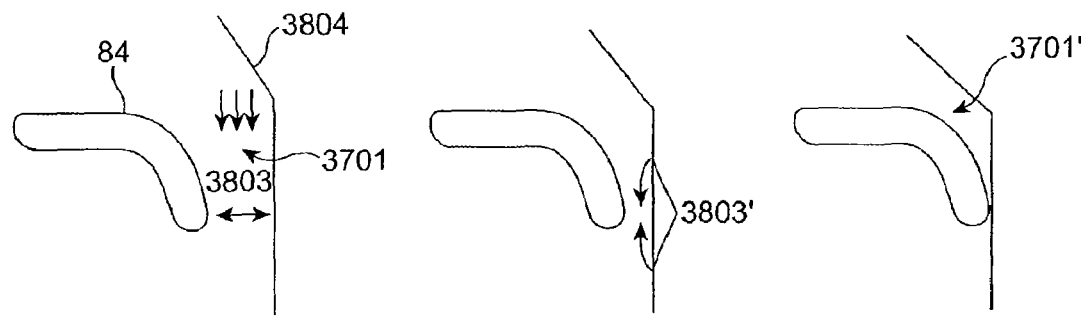
FIG. 37 depicts the progression of an apneic event.

FIG. 37 depicts the occurrence of an apneic event due to the blockage of airway 3701 caused by the movement of the soft palate 84. FIG. 37A shows the soft palate 84 position during normal breathing cycle. An airway gap 3803 is maintained between the soft palate 84 and the laryngeal wall 3804 to maintain airflow 3805. FIG. 37B shows the position of the soft palate 84 just prior to the airway 3701 blockage. It can be seen that the gap 3803' in this case is smaller than the gap 3803 in FIG. 37A. FIG. 37C shows the soft palate 84 blocking the airway 3701', leading to the occurrence of an apneic event. In one aspect of the invention, the event shown in FIG. 37C is prevented by taking preemptive action during occurrence of event depicted in FIG. 37B.

One aspect of the invention is an airway implant device with a sensor for sensing the occurrence of apneic events and actuating the device. The invention also includes methods of use of such device.

Figure 38:
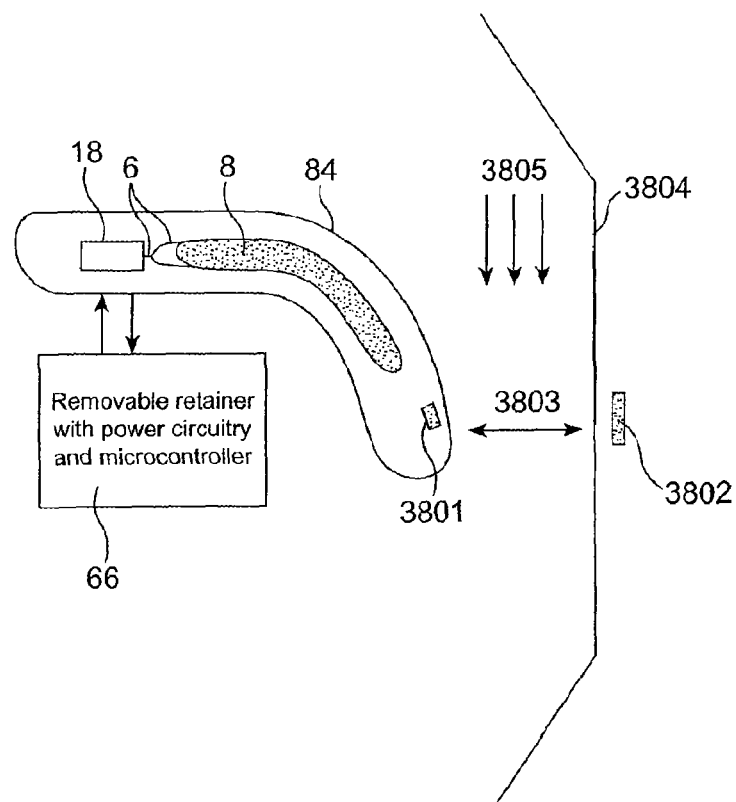
FIG. 38 depicts an embodiment of an airway implant device with sensors in the soft palate and laryngeal wall.
Figures 39A, 39B, 39C:
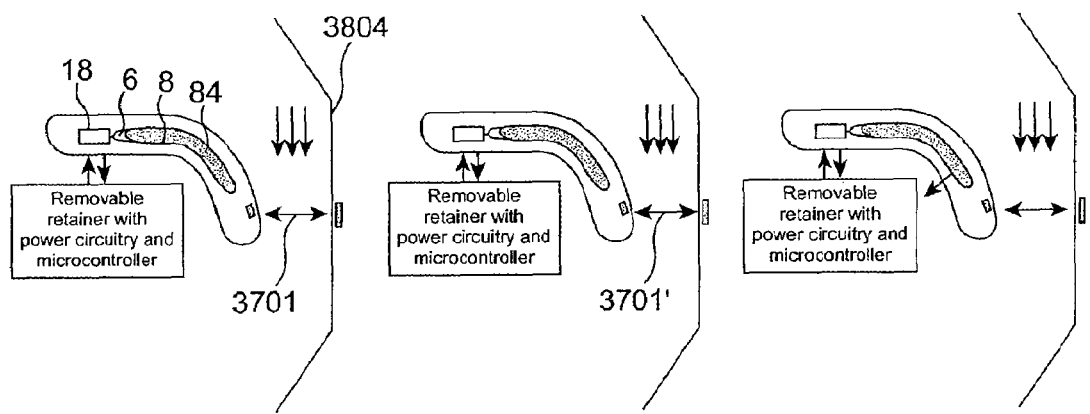
FIG. 39 depicts the functioning of an airway implant device with sensors in the soft palate and laryngeal wall.

One embodiment of an airway implant device with sensor is depicted in FIG. 38. Non-contact distance sensors 3801 and 3802 are mounted on the laryngeal wall 3804 and also on the soft palate 84 to sense the airway gap between the soft palate 84 and the laryngeal wall 3804. One or more gap values are calibrated into a microcontroller controlling the airway implant device. The functioning of the airway implant device with a sensor is depicted in FIG. 39. During the occurrence of the apneic event the gap between the soft palate 84 and the laryngeal wall 3804 decreases. This gap information is continuously monitored by the airway implant device microcontroller. When the gap becomes smaller than a preset threshold value, the airway implant microcontroller actuates the airway implant, which stiffens the soft palate 84 and the gap between the soft palate 84 and the laryngeal walls 3804 increases. When this gap crosses an upper threshold, the microcontroller powers off the airway implant actuator.

In one embodiment, the operation of the device is as follows:
a) A threshold gap is calibrated into the microcontroller which is present in the removable retainer of the device. This threshold gap corresponds to the gap 3803' formed by the position of the soft palate with respect to the laryngeal wall as depicted in the FIG. 37B, i.e., a distance at which an apneic event could be triggered or an apneic event occurs. This calibration can take place in real time or when the device is being installed.
b) The non-contact sensor constantly monitors the gap and the information is constantly analyzed by a program present in the microcontroller.
c) The airway implant actuator is in the off state (not powered state) as long as the threshold gap is not reached.
d) When the gap is equal to the threshold gap, the micro controller, powers on the airway implant actuator (on state). This leads to the stiffening of the airway implant actuator, which in-turn stiffens the soft palate.
e) This stiffening of the soft palate prevents the obstruction of the airway and modulates the occurrence of an apneic event.
f) When the gap becomes more than the threshold gap, the micro-controller turns off the airway implant actuator (off state).

Typically, an algorithm in the micro-controller controls the actuation of the actuator. An example of the algorithm is—
if (gap<threshold gap); {Voltage applied to airway implant actuator=high (on state)} or else {Voltage applied to the airway implant actuator=low (off state)}

Complex algorithms, such as adaptive algorithms, can also be used. The objective of the adaptive algorithm can be to selectively control the stiffness of the soft palate by varying the power applied to the airway implant actuator.

Another example of an algorithm to selectively control the stiffness of the soft palate is:

```
If(gap < or = g)
{Apply full power to the airway implant actuator}
Else
If(gap =g1)
{Voltage applied to airway implant actuator = v1}
Else if (gap = g2)
{Voltage applied to airway implant actuator = v2}
Else if (gap =g3)
{Voltage applied to airway implant actuator =v3}
Note (g1, g2, g3 > g)
```

Figure 41:
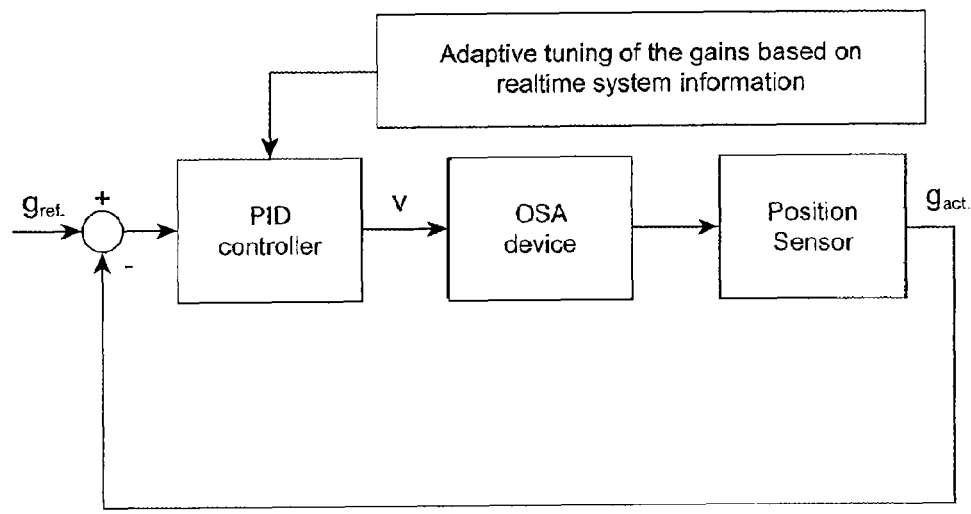
FIG. 41 depicts an example of controller suitable for use with an airway implant device.

An example of a controller to maintain a predetermined reference gap is shown is FIG. 41. The objective of this algorithm is to maintain an actual airway gap $g_{act}$ as close to the reference airway gap $g_{ref}$ as possible by controlling the airway implant device actuator. The actual airway gap between the soft palate and the laryngeal wall $g_{act}$ is measured and this information is the output of the position sensor. This airway gap information is feedback to the microcontroller which has a controller algorithm embedded in it. In the microcontroller the $g_{act}$ is compared to a $g_{ref}$ and based on the difference between both, the Proportional Integral Derivative (PID) controller generates a controlling voltage which is supplied to the airway implant device. The PID controller can have fixed gains or can have the gains adaptively tuned based on system information.

In alternative embodiments, the sensor can be a wall tension sensor, an air pressure sensor, or an air flow monitoring sensor. In another embodiment, instead of fully turning the airway implant actuator on or off, the actual value of the airway gap can be used to selectively apply varying voltage to the airway implant actuator, hence selectively varying the stiffness of the soft palate. In yet another embodiment, if the airway implant actuator exhibits a lack of force retention over an extended period of time under DC voltage, a feedback control algorithm may be implemented in the microcontroller, which uses the sensory information provided by the sensors to control the stiffness of the soft palate by maintaining the force developed by the airway implant actuator.

Figure 40:
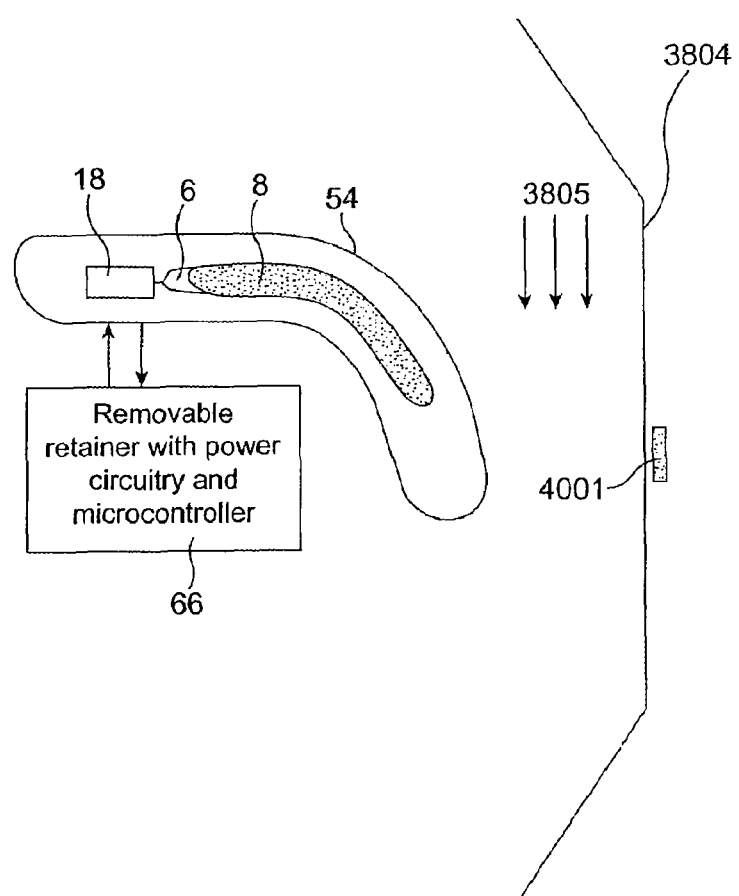
FIG. 40 depicts an embodiment of an airway implant device with a sensor in the laryngeal wall.

Another embodiment of the invention is depicted in FIG. 40. In this embodiment, the wall tension sensed by the wall tension sensor 4001 implanted into the laryngeal wall 3804 is used as a threshold criterion for activating the airway implant actuator. A wall tension sensor can also be placed in a pharyngeal wall or other suitable airway wall. The sensors of this invention can be placed in an airway wall or proximal to an airway wall.

Some of the advantages of the use of an airway sensor with an airway implant device include: optimization of the power consumed by the airway implant device and hence extension of the life of the device; assistance in predicting the occurrence of apneic event, and hence selective activation of the device in order to minimize any patient discomfort; flexibility to use a feedback control system if required to compensate for any actuator irregularities; and possible configuration of the system to interact with an online data management system which will store different parameters related to apneic events for a patient. This system can be accessed by the doctor, other health care providers, and the insurance agency which will help them provide better diagnosis and understanding of the patient's condition.

In preferred embodiments, the airway gap is individually calculated and calibrated for each patient. This information can be stored in the microcontroller. The sensors are described herein mainly in the context of airway implant devices comprising of electroactive polymer actuators. The sensors can also be used with airway implant devices comprising other active actuators, i.e., actuators that can be turned on, off, or otherwise be controlled, such as magnets. The sensors can be used to activate, in-activate, and/or modulate magnets used in airway implant devices. Preferably, the sensors are in the form of a strip, but can be any other suitable shape for implantation. They are typically deployed with a needle with the help of a syringe. The sensor can be made with any suitable material. In preferred embodiments, the sensor is a smart material, such as an IPMC. The sensor is typically in connection with a microcontroller, which is preferably located in the retainer. This connection can be either physical or wireless.

Suitable sensors include, but are not limited to, an electroactive polymer like ionic polymer metal composite (IPMC). Suitable materials for IPMC include perfluorinated polymer such as polytetrafluoroethylene, polyfluorosulfonic acid, perfluorosulfonate, and polyvinylidene fluoride. Other suitable polymers include polyethylene, polypropylene, polystyrene, polyaniline, polyacrylonitrile, cellophane, cellulose, regenerated cellulose, cellulose acetate, polysulfone, polyurethane, polyvinyl acetate. Typically, the electroactive polymer element includes a biocompatible conductive material such as platinum, gold, silver, palladium, copper, and/or carbon. Commercially available materials suitable for use as a sensor include Nafion® (made by DuPont), Flemion® (made by Asahi Glass), Neosepta® (made by Astom Corporation), Ionac® (made by Sybron Chemicals Inc), Excellion™ (made by Electropure). Other materials suitable for use as a sensor include materials with piezoelectric properties like piezoceramics, electrostrictive polymers, conducting polymers, materials which change their resistance in response to applied strain or force (strain gauges) and elastomers.

The airway implant devices of the present invention, with or without the sensor, can be used to treat snoring. For snoring, the sensor can be adapted and configured to monitor air passageways so as to detect the possible occurrence of snoring or to detect the possible worsening of ongoing snoring. Preferably the sensors are capable of detecting relaxation of tissues in the throat, which can cause them to vibrate and obstruct the airway. Other tissues that can be monitored by the sensor include the mouth, the soft palate, the uvula, tonsils, and the tongue.

Another disease that can be treated with the devices of the present invention includes apnea. The sensor preferably monitors the throat tissue for sagging and/or relaxation to prevent the occurrence of an apneic event. Other tissues that can be monitored by the sensor include the mouth, the soft palate, the uvula, tonsils, and the tongue.

Methods of Making Electroactive Polymer Element

In some embodiments, the EAP element is an IPMC strip which is made from a base material of an ionomer sheet, film or membrane. The ionomer sheet is formed using ionomer dispersion.

IPMC is made from the base ionomer of, for example, polyethylene, polystyrene, polytetrafluoroethylene, polyvinylidene fluoride (PVDF) (e.g., KYNAR® and KYNAR Flex®, from ATOFINA, Paris, France, and SOLEF®, from Solvay Solexis S. A., Brussels, Belgium), hydrophilic-PVDF (h-PVDF), polyfluorosulfonic acid based membranes like NAFION® (from E.I. Du Point de Nemours and Company, Wilmington, Del.), polyaniline, polyacrylonitrile, cellulose, cellulose acetates, regenerated cellulose, polysulfone, polyurethane, and combinations thereof. The conductive material that is deposited on the ionomer can be gold, platinum, silver, palladium, copper, graphite, conductive carbon, or combinations thereof. Conductive material is deposited on the ionomer either by electrolysis process, vapor deposition, sputtering, electroplating, or combination of processes.

The IPMC is cut into the desired implant shape for the EAP element. The electrical contact (e.g., anode and cathode wires for EAP element) is connected to the IPMC surfaces by, for example, soldering, welding, brazing, potting using conductive adhesives, or combinations thereof. The EAP element is configured, if necessary, into specific curved shapes using mold and heat setting processes.

In some embodiments, the EAP element is insulated with electrical insulation coatings. Also, the EAP element can be insulated with coatings that promote cell growth and minimize fibrosis, stop cell growth, or kill nearby cells. The insulation can be a biocompatible material. The EAP element is coated with polymers such as polypropylene, poly-L-lysine, poly-D-lysine, polyethylene glycol, polyvinyl alcohol, polyvinyl acetate, polymethyl methacrylate, or combinations thereof. The EAP element can also be coated with hyaluronic acid. The coating is applied to the device by standard coating techniques like spraying, electrostatic spraying, brushing, vapor deposition, dipping, etc.

In one example, a perfluorosulfonate ionomer, PVDF or h-PVDF sheet is prepared for manufacturing the EAP element. In an optional step, the sheet is roughened on both sides using, for example, about 320 grit sand paper and then about 600 grit sand paper; then rinsed with deionized water; then submerged in isopropyl alcohol (IPA); subjected to an ultrasonic bath for about 10 minutes; and then the sheet is rinsed with deionized water. The sheet is boiled for about 30 minutes in hydrochloric acid (HCL). The sheet is rinsed and then boiled in deionized water for about 30 minutes. The sheet is then subject to ion-exchange (i.e., absorption). The sheet is submerged into, or otherwise exposed to, a metal salt solution at room temperature for more than about three hours. Examples of the metal salt solution are tetraammineplatinum chloride solution, silver chloride solution, hydrogen tetrachloroaurate, tetraamminepalladium chloride monohydrate or other platinum, gold, silver, carbon, copper, or palladium salts in solution. The metal salt solution typically has a concentration of greater than or equal to about 200 mg/100 ml water. 5% ammonium hydroxide solution is added at a ratio of 2.5 ml/100 ml to the tetraammineplatinum chloride solution to neutralize the solution. The sheet is then rinsed with deionized water. Primary plating is then applied to the sheet. The sheet is submerged in water at about 40° C. 5% solution by weight of sodium borohydride and deionized water is added to the water submerging the sheet at 2 ml/180 ml of water. The solution is stirred for 30 minutes at 40° C. The sodium borohydride solution is then added to the water at 2 ml/180 ml of water and the solution is stirred for 30 minutes at 40° C. This sodium borohydride adding and solution stirring is performed six times total. The water temperature is then gradually raised to 60° C. 20 ml of the sodium borohydride solution is then added to the water. The solution is stirred for about 90 minutes. The sheet is then rinsed with deionized water, submerged into 0.1N HCl for an hour, and then rinsed with deionized water.

In some embodiments, the sheet receives second plating. The sheet is submerged or otherwise exposed to a tetraammineplatinum chloride solution at a concentration of about 50 mg/100 ml deionized water. 5% ammonium hydroxide solution is added at a rate of 2 ml/100 ml of tetrammineplatinum chloride solution. 5% by volume solution of hydroxylamine hydrochloride in deionized water is added to the tetraammineplantium chloride solution at a ratio of 0.1 of the volume of the tetraammineplatinum chloride solution. 20% by volume solution of hydrazine monohydrate in deionized water is added to the tetraammineplatinum chloride solution at a ratio of 0.05 of the volume of the tetraammineplantinum chloride solution. The temperature is then set to about 40° C. and the solution is stirred.

A 5% solution of hydroxylamine hydrochloride is then added at a ratio of 2.5 m/100 ml of tetraammineplatinum chloride solution. A 20% solution of hydrazine monohydrate solution is then added at a ratio of 10.25 ml/100 ml tetraammineplatinum chloride solution. The solution is stirred for 30 minutes and the temperature set to 60° C. The above steps in this paragraph can be repeated three additional times. The sheet is then rinsed with deionized water, boiled in HCI for 10 minutes, rinsed with deionized water and dried.

In some embodiments, the polymer base is dissolved in solvents, for example dimethyl acetamide, acetone, methylethyle ketone, toluene, dimethyl carbonate, diethyl carbonate, and combinations thereof. The solvent is then allowed to dry, producing a thin film. While the solution is wet, a low friction, (e.g., glass, Teflon) plate is dipped into the solution and removed. The coating on the plate dries, creating a think film. The plate is repeatedly dipped into the solution to increase the thickness of the film.

Polyvinyl alcohol, polyvinyl pyrrolidone, polyinyl acetate or combinations thereof can be added to a PVDF solution before drying, thus contributing hydrophilic properties to PVDF and can improve ion migration through the polymer film during manufacture. Dye or other color pigments can be added to the polymer solution.

Method of Using

Figure 25:
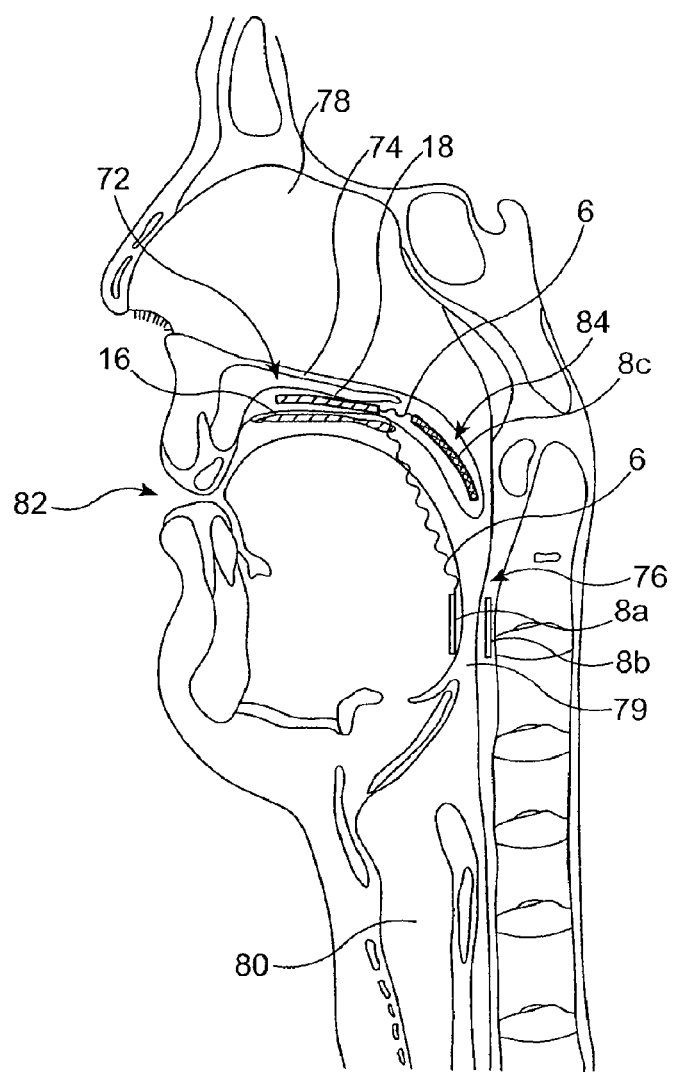
FIG. 25 shows a sagittal section through a head of a subject illustrating an embodiment of a method for using the airway implant device.

FIG. 25 illustrates an embodiment of a method of the airway implant device of the present invention. In this embodiment, the first inductor 18 is implanted in the mouth roof 72, for example in or adjacent to the hard palate 74. Wire leads 6 connect the first inductor 18 to the actuator elements 8a, 8b, and 8c. A first actuator element 8a is implanted in the base of the tongue at the pharynx wall 76. A second actuator element 8b is integral with the first actuator element 8a (e.g., as two sections of a hollow cylindrical actuator element 8, such as shown in FIG. 17). The first and second actuator elements 8a and 8b can be separate and unattached elements. The third actuator element 8c is implanted in the uvula and/or soft palate 84. The actuator elements 8 can also be implanted in the wall of the nasal passages 78, higher or lower in the pharynx 79, such as in the nasal pharynx, in the wall of the trachea 80, in the larynx (not shown), in any other airway, or combinations thereof. The second inductor 16 is worn by the patient in the mouth 82. The second inductor 16 is connected to an integral or non-integral power source. The second inductor 16 comprises one or multiple induction coils. The second inductor 16 inductively transmits RF energy to the first inductor 18. The first inductor 18 changes the RF energy into electricity. The first inductor 18 sends a charge or current along the wire leads 6 to the actuator elements 8a, 8b, and 8c. The actuator elements 8a, 8b, and 8c are energized by the charge or current. The energized actuator elements 8a, 8b, and 8c increase the stiffness and/or alter the shape of the airways. The energized actuator elements 8a, 8b, and 8c modulate the opening of the airways around which the actuator elements 8a, 8b, and 8c are implanted. The non-energized actuator elements 8a, 8b, and 8c are configured to conform to the airway around which the actuator elements 8a, 8b, and 8c are implanted. The non-energized actuator elements 8a, 8b, and 8c are flexible and soft.

Figure 26:
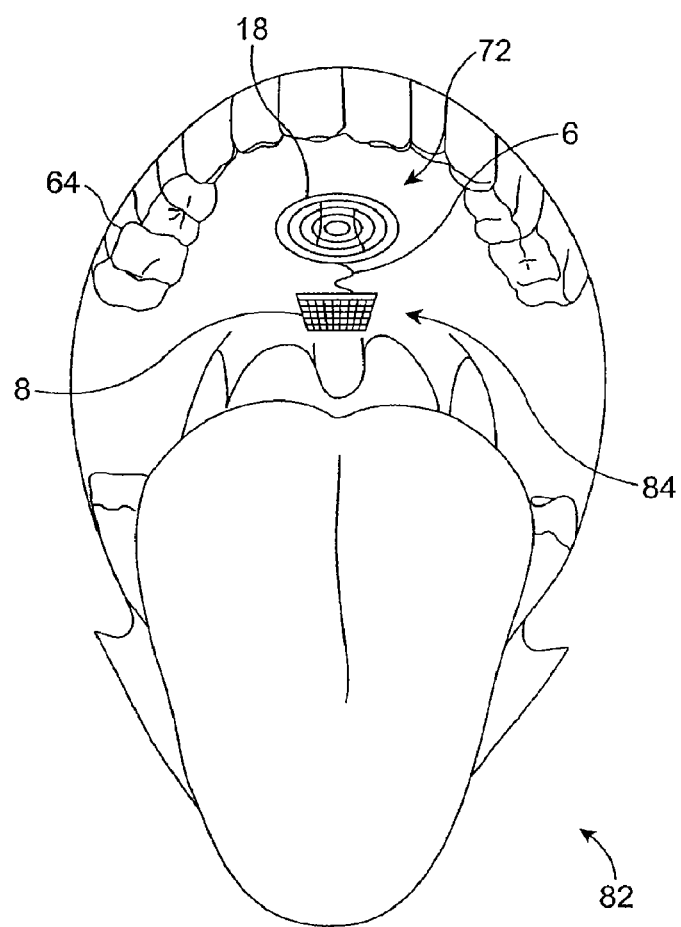
FIG. 26 illustrates an anterior view of the mouth with see-through mouth roofs to depict an embodiment of a method for using the airway implant device.
Figure 27:
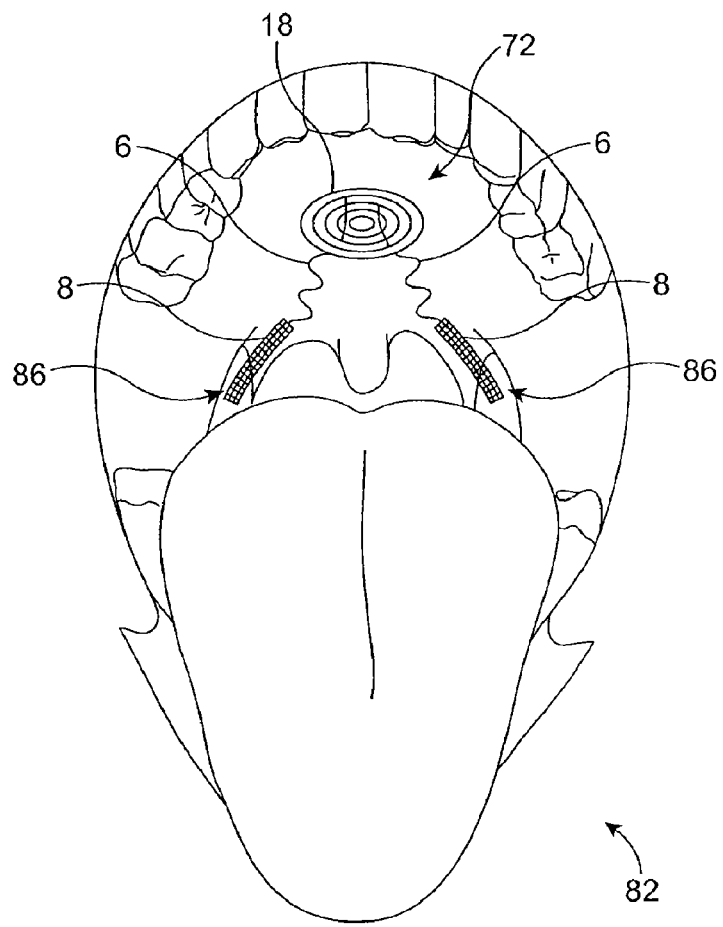
FIG. 27 illustrates an anterior view of the mouth with see-through mouth roofs to depict an embodiment of a method for using the airway implant device.
Figure 28:
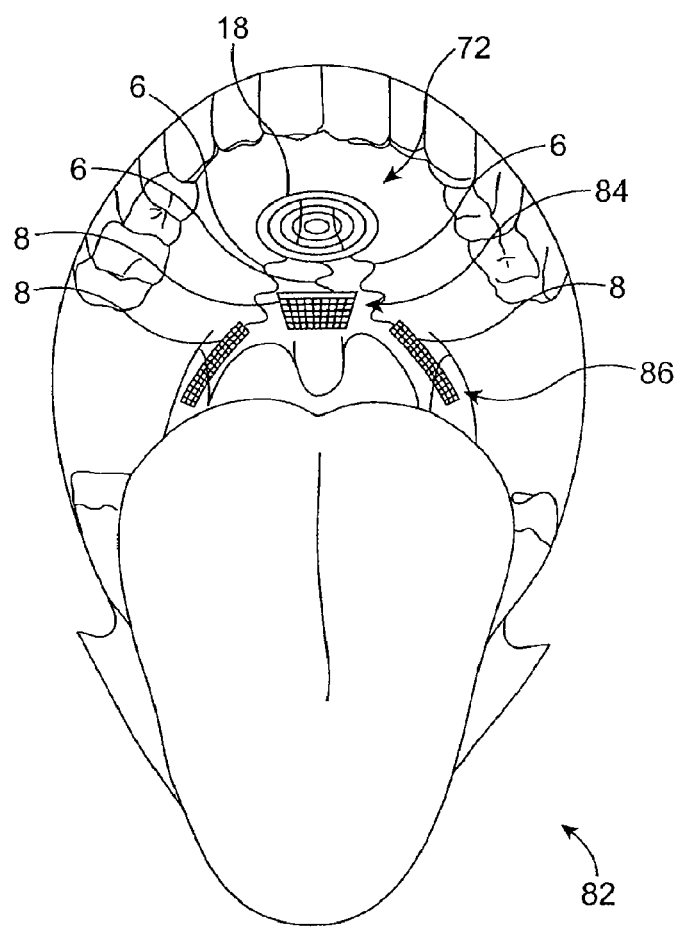
FIG. 28 illustrates an anterior view of the mouth with see-through mouth roofs to depict an embodiment of a method for using the airway implant device.
Figure 29:
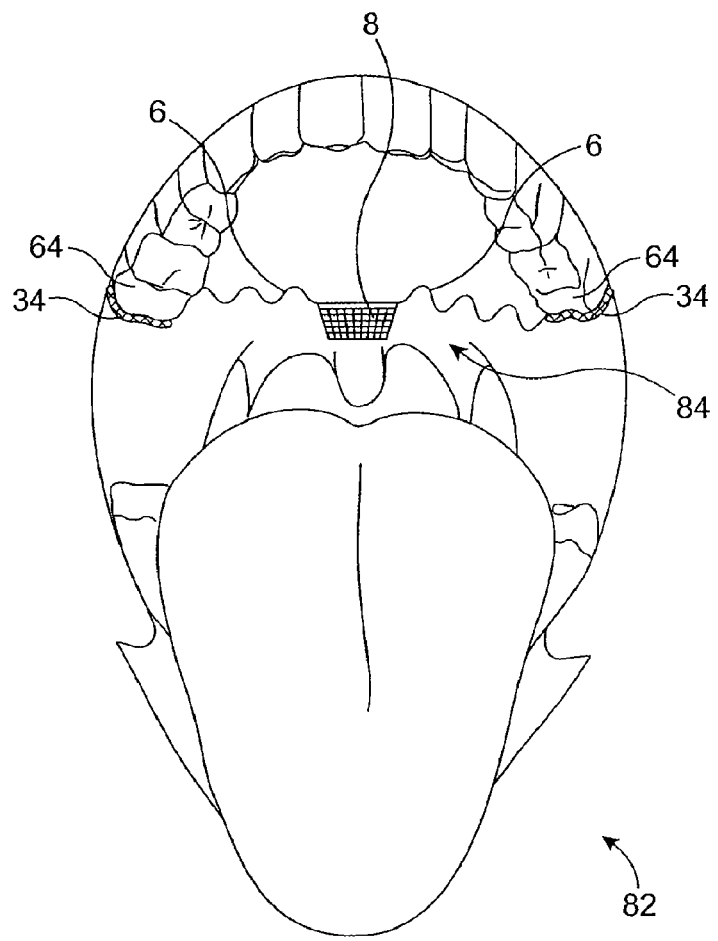
FIG. 29 illustrates an anterior view of the mouth with see-through mouth roofs to depict an embodiment of a method for using the airway implant device.

FIG. 26 illustrates another embodiment of the invention. In this embodiment, the first inductor 18 is implanted in the mouth roof 72 and attached to a actuator element 8 via the wire lead 6. The actuator element 8 is preferably in the soft palate 84. In another embodiment, FIG. 27 illustrates that the first inductor 18 is implanted in the mouth roof 72 and attached to two actuator elements 8 via two wire leads 6. The actuator elements 8 are implanted in side walls 86 of the mouth 82. In yet another embodiment, as illustrated in FIG. 28, the first inductor 18 is implanted in the mouth roof 72 and attached to three actuator elements 8 via three wire leads 6. The actuator elements 8 are implanted in the soft palate 84 and the side walls 86 of the mouth 82. FIG. 29 illustrates an embodiment in which the first conductors (not shown, e.g., the tooth sockets), are attached to, and in conductive electrical communication with, the second conductors. The retainer 66, such as shown in FIG. 23, can be worn by the patient to energize the actuator element 8. The tooth sockets are removably attached to the first conductors 34. The first conductors 34 are dental fillings, conductive posts adjacent to and/or through the teeth 64.

Figure 33:
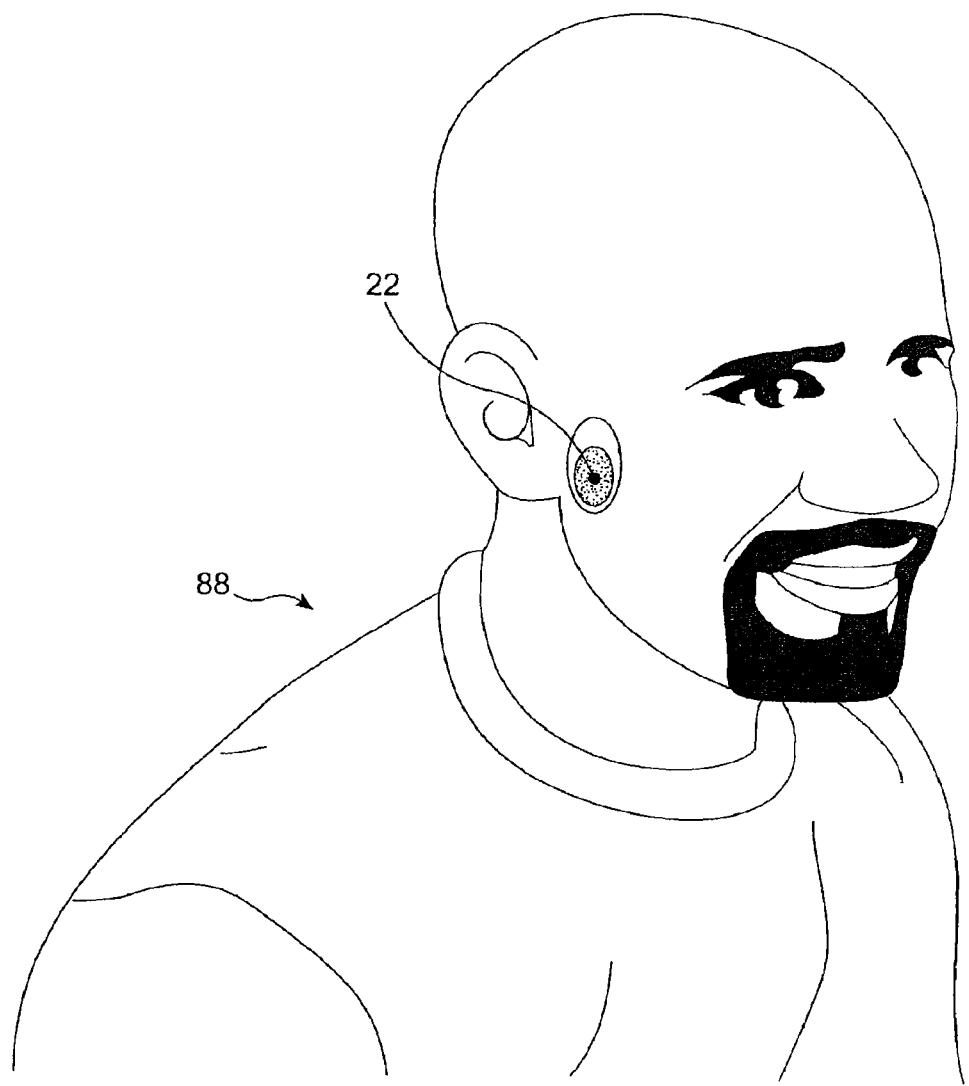
FIG. 33 illustrates an embodiment in which a patient wears the non-implanted portion of the device on the cheeks.

FIG. 33 illustrates an embodiment in which a patient 88 has the first transducer (not shown) implanted in the patient's cheek and wears the non-implanted portion 22, such as shown in FIG. 24, on the outside of the patient's cheek. The non-implanted portion 22 energizes the implanted portion (not shown).

Figure 34A:
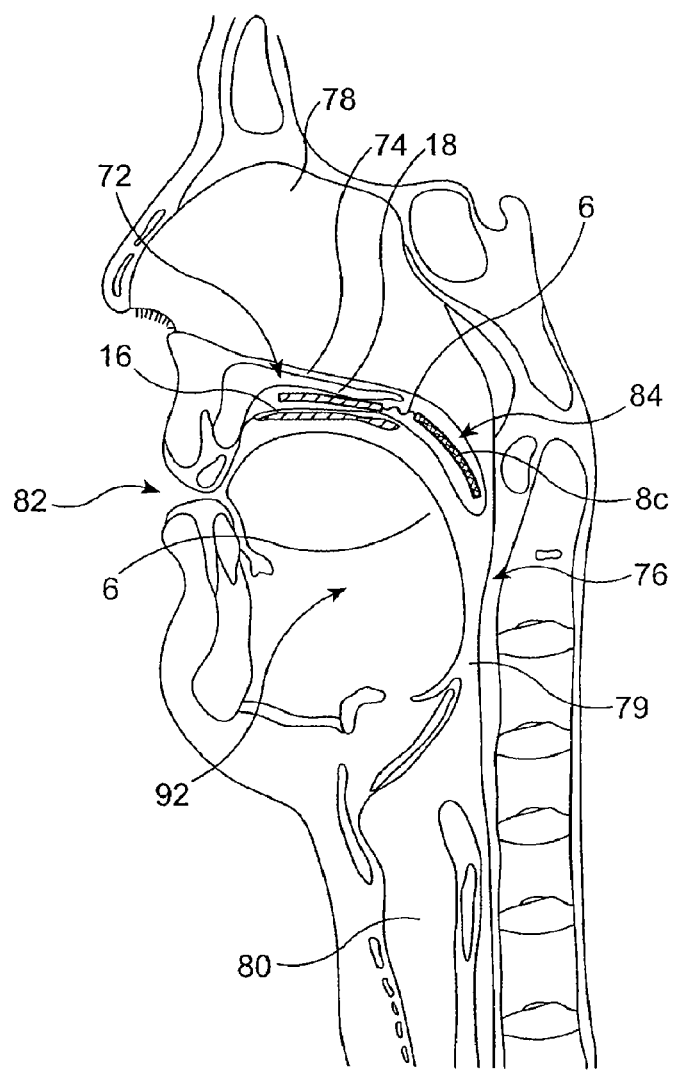
FIG. 34A-34B illustrates an embodiment of a method of the invention with the airway implant in the soft palate.
Figure 34B:
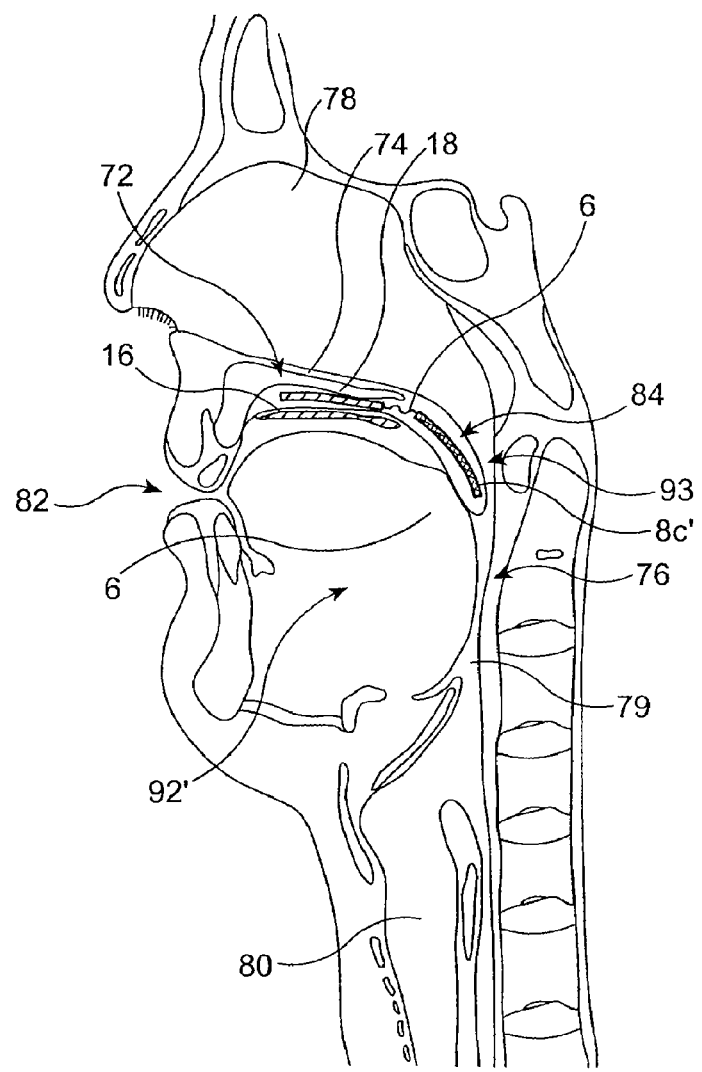

FIGS. 34-36 depict some of the ways in which the implant devices function to open the airways. FIGS. 34A and 34B depict a side view of a patient with a soft palate implant 8c and a non-implanted portion of the device, with a second inductor 16, which in this case is a wearable mouth piece. The wearable mouth piece includes a transmitter coil, a power source, and other electronics, which are not depicted. Also, shown is a first inductor 18. The implant device has the ability to sense and deflect the tongue so as to open the airway. FIG. 34A depicts the tongue 92 in its normal state. During sleep, when the tongue collapses 92', as shown in FIG. 34B, the actuator element 8c' senses the collapsed tongue and is energized via the mouthpiece and first inductor and it stiffens to push away the tongue from the airway and keeps the airway open. This opening of the airway can be partial or complete. In some embodiments, particularly the embodiments without the sensor, the implant is powered when the patient is asleep such that the actuator element 8 is energized and keeps the collapsed tongue away from the airway.

Figure 35A:
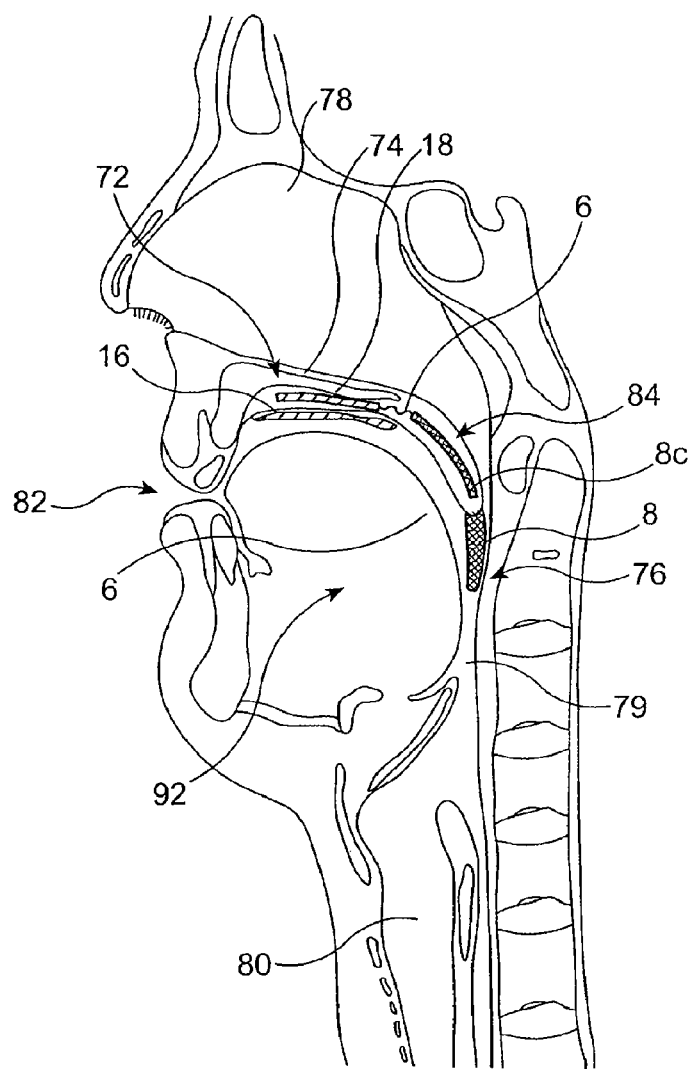
FIG. 35A-35B illustrates an embodiment of a method of the invention with the airway implants in the soft palate and lateral pharyngeal walls.
Figure 35B:
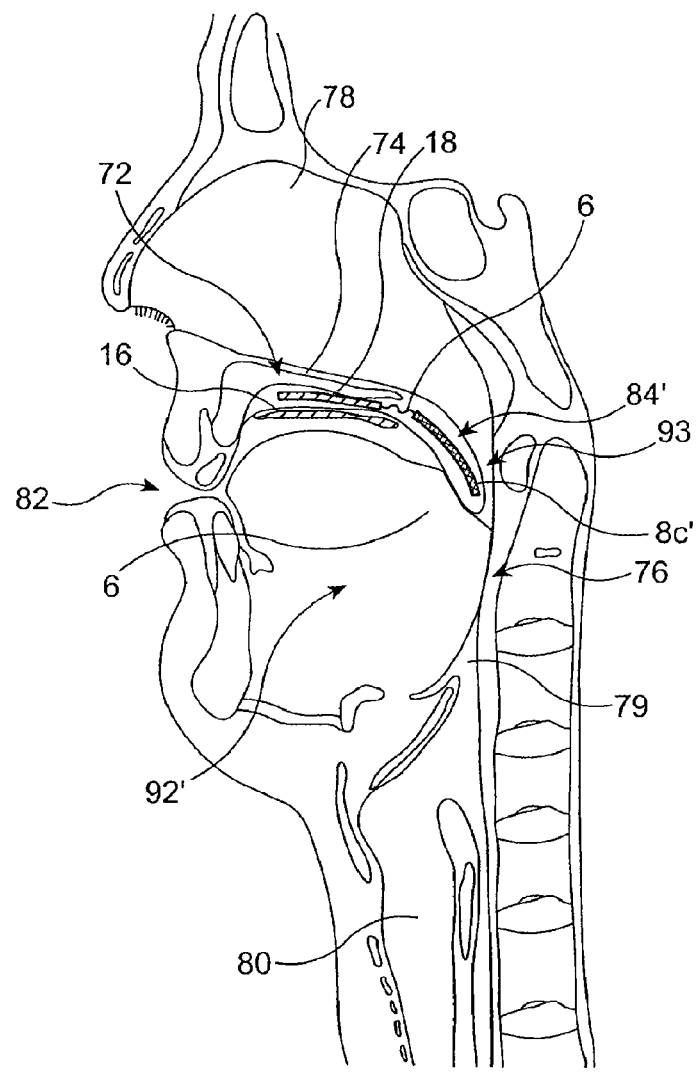
Figure 36A:
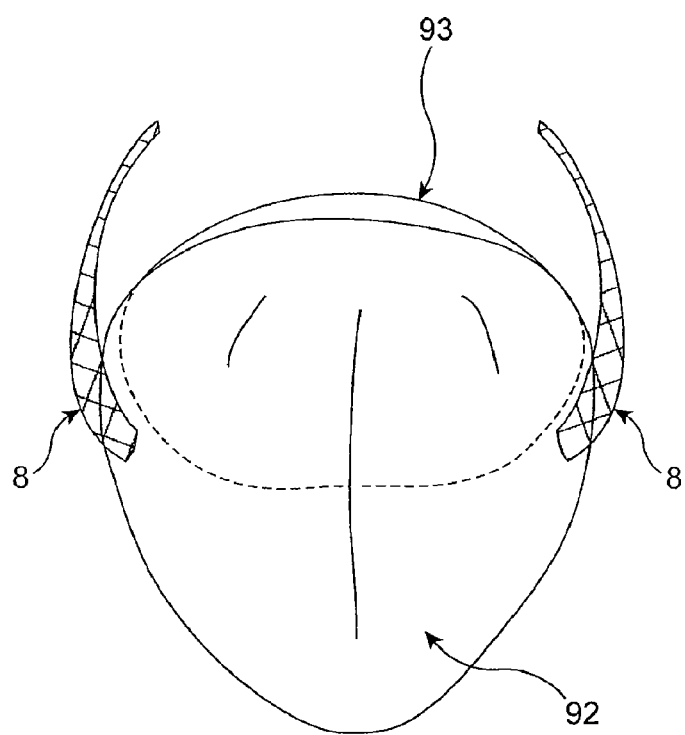
FIG. 36A-36B illustrates an embodiment of a method of the invention with the airway implants in the lateral pharyngeal walls.
Figure 36B:
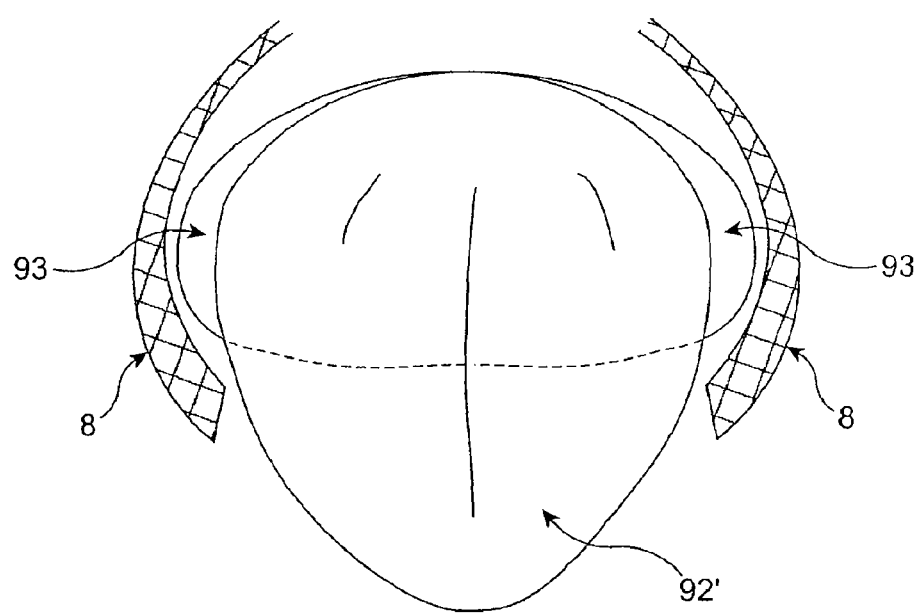

FIGS. 35 and 36 depict an embodiment of keeping the airways open with lateral wall implants. FIG. 35A shows a side view of a patient's face with a actuator element 8 located in the lateral wall of the airway. FIG. 35A depicts the tongue 92 in its normal state. FIG. 35B depicts the tongue 92' in a collapsed state. When the tongue is in this state or before it goes into the collapsed state the actuator element 8 is energized so as to stretch the lateral walls and open the airway, as shown in FIG. 36B. FIGS. 36A and 36B are a view of the airway as seen through the mouth of patient. FIG. 36 A depicts the actuator elements 8 in a non-energized state and the tongue in a non-collapsed state. When the tongue collapses or it has a tendency to collapse, such as during sleep, the actuator element 8 is energized and airway walls are pushed away from the tongue and creates an open air passageway 93. This embodiment is particularly useful in obese patients.

Airway Diseases

During sleep, the muscles in the roof of the mouth (soft palate), tongue and throat relax. If the tissues in the throat relax enough, they vibrate and may partially obstruct the airway. The more narrowed the airway, the more forceful the airflow becomes. Tissue vibration increases, and snoring grows louder. Having a low, thick soft palate or enlarged tonsils or tissues in the back of the throat (adenoids) can narrow the airway. Likewise, if the triangular piece of tissue hanging from the soft palate (uvula) is elongated, airflow can be obstructed and vibration increased. Being overweight contributes to narrowing of throat tissues. Chronic nasal congestion or a crooked partition between the nostrils (deviated nasal septum) may be to blame.

Snoring may also be associated with sleep apnea. In this serious condition, excessive sagging of throat tissues causes your airway to collapse, preventing breathing. Sleep apnea generally breaks up loud snoring with 10 seconds or more of silence. Eventually, the lack of oxygen and an increase in carbon dioxide signal causes the person to wake up, forcing the airway open with a loud snort.

Obstructive sleep apnea occurs when the muscles in the back of the throat relax. These muscles support the soft palate, uvula, tonsils and tongue. When the muscles relax, the airway is narrowed or closed during breathing in, and breathing is momentarily cut off. This lowers the level of oxygen in the blood. The brain senses this decrease and briefly rouses the person from sleep so that the airway can be reopened. Typically, this awakening is so brief that it cannot be remembered. Central sleep apnea, which is far less common, occurs when the brain fails to transmit signals to the breathing muscles.

Thus, it can be seen that airway disorders, such as sleep apnea and snoring, are caused by improper opening of the airway passageways. The devices and methods described herein are suitable for the treatment of disorders caused by the improper opening of the air passageways. The devices can be implanted in any suitable location such as to open up the airways. The opening of the passageways need not be a complete opening and in some conditions a partial opening is sufficient to treat the disorder.

In addition to air passageway disorders, the implants disclosed herein are suitable for use in other disorders. The disorders treated with the devices include those that are caused by improper opening and/or closing of passageways in the body, such as various locations of the gastro-intestinal tract or blood vessels. The implantation of the devices are suitable for supporting walls of passageways The devices can be implanted in the walls of the gastro-intestinal tract, such as the esophagus to treat acid reflux. The gastro-intestinal tract or blood vessel devices can be used in combination with the sensors described above. Also, the implants and/or sphincters can be used for disorders of fecal and urinary sphincters. Further, the implants of said invention can be tailored for specific patient needs.

IPMC Based Implantable OSA Sensor

Figure 53A:
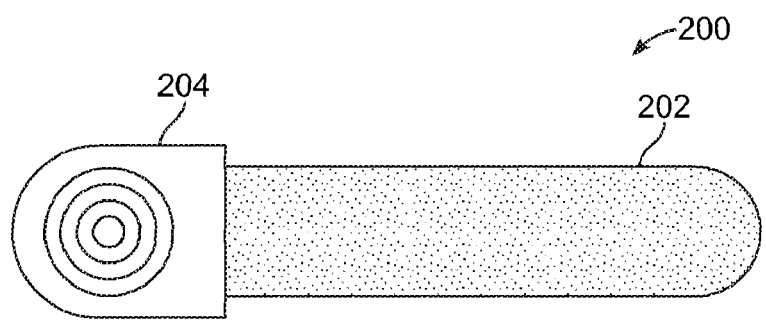
FIG. 53A illustrates a top view of a implantable obstructive sleep apnea sensor, according to one embodiment of the invention.

FIG. 53A shows an implantable OSA sensor 200, according to one embodiment of the invention. It should be understood that the term "implantable" does not limit the use of the implantable OSA sensor 200, or any other sensor described herein. Thus, the implantable OSA sensor 200, or any other sensor described herein, may be permanently or temporarily coupled to a patient, for example for several minutes, hours, weeks, or years. The implantable OSA sensor 200, or any other sensor described herein, may also be reused and coupled to a patient intermittently, for example during sleep periods. The implantable OSA sensor 200 includes an ionic polymer metal composite (IPMC) sensor 202 coupled to a transmitter device 204. The IPMC sensor 202 may be configured as an elongated strip. In one embodiment the sensor 202 includes a length of 80 mm and a width of 40 mm, and thickness of 0.2-0.4 mm. The IPMC sensor 202 includes a ionic polymer layer with metal coated on both sides. The metal coating functions as an electrode and may be for example platinum. The IPMC sensor 202 functions on the principal that when hydrated, for example with saliva, movement or mechanical bending of the IPMC sensor 202 causes cations (positively charged ions) to move from a high density region (e.g. an interior radius region of a bend) to a low density region (e.g. an outer radius region of a bend). Accordingly, during bending, cations will accumulate in the electrodes to create a detectable electrical output, which may be a charge or voltage. The IPMC sensor 202 is very advantageous because the it does not require a power source to generate an electrical output. The transmitter device 204 is electrically and mechanically coupled to the IPMC sensor 202 to receive generated electrical output. The transmitter device 204 generally includes a housing for supporting electronic circuitry. The transmitter device 204 and the IPMC sensor 202 may be integrally constructed, as shown. The IPMC sensor 202 may be constructed similarly to the IPMC actuators disclosed herein.

Figure 53B:
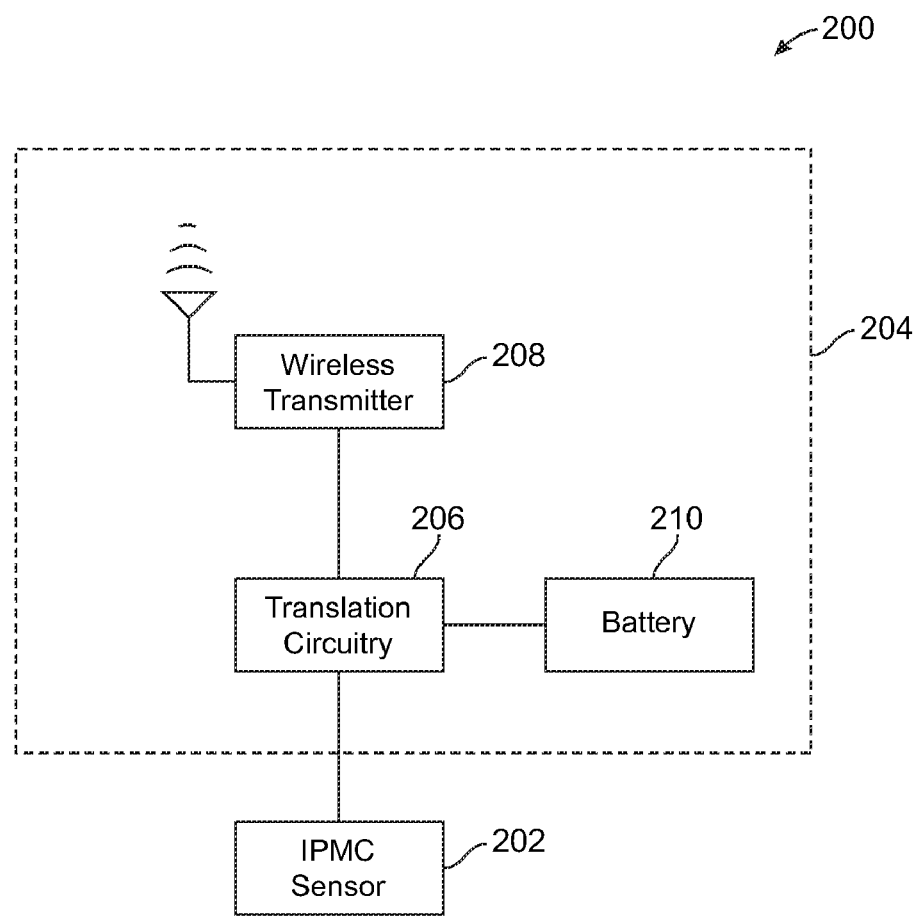
FIG. 53B illustrates a schematic diagram of the implantable obstructive sleep apnea sensor, according to one embodiment of the invention.

FIG. 53B shows a schematic diagram of the implantable OSA sensor 200, according to one embodiment of the invention. The IPMC sensor 202 is electrically coupled to translation circuitry 206. The translation circuitry 206 may translate an incoming electrical output from the IPMC sensor 202 into a wirelessly propagated signal. For example the translation circuitry 206 may include amplification or conversion circuitry. The translation circuitry 206 may convert the incoming electrical output into an analog or a digital signal. The translation circuitry 206 will also include transmission circuitry for wireless transmission of a signal according to a transmission standard, for example WiFi, Bluetooth 1.1 and greater, or IEEE802.11. A wireless transmitter 208 is electrically coupled to the translation circuitry 206, for transmission of a signal. The translation circuitry 206 may also be controlled from an outside source through the wireless transmitter 208. A battery 210 provides power to the translation circuitry 206 and wireless transmitter 208. The battery 210 may be rechargeable or replaceable.

Figure 53C:
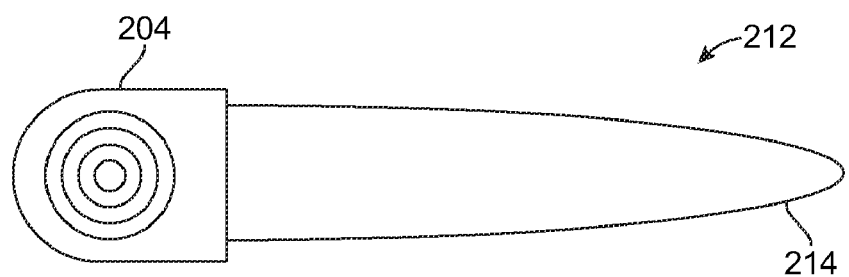
FIG. 53C-53H illustrates a top views of an implantable obstructive sleep apnea sensors, according to respective embodiments of the invention.

FIG. 53C shows an implantable OSA sensor 212, according to one embodiment of the invention. The implantable OSA sensor 212 is constructed similarly to the implantable OSA sensor 200 shown in FIGS. 53A and 53B. However the IPMC sensor 214 includes a tapered shape which is longer and profiled to follow the shape of the soft palate. The IPMC sensor 214 may also be custom shaped to match a individual patient's soft palate. The IPMC sensor 214 may also be precontoured to match the curve of a patient's soft palate.

Figure 53D:
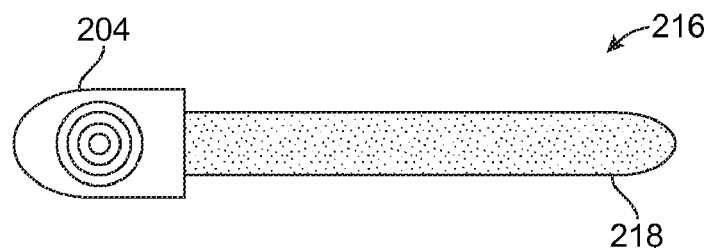

FIG. 53D shows an implantable OSA sensor 216, according to one embodiment of the invention. The implantable OSA sensor 216 is constructed similarly to the implantable OSA sensor 200 shown in FIGS. 53A and 53B. However, the IPMC sensor 218 includes a smaller width and length which may thus fit inside smaller mouths.

Figure 53E:
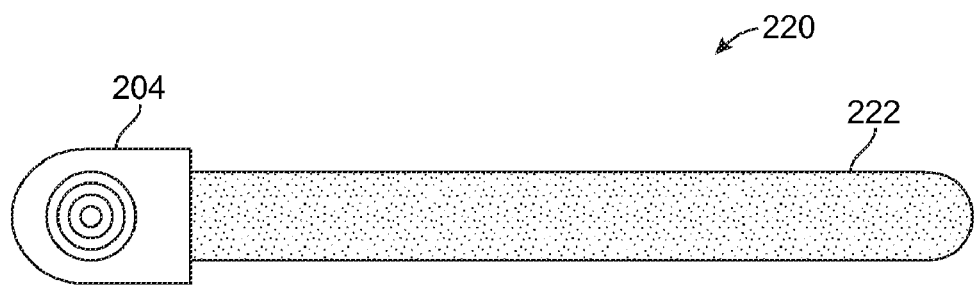

FIG. 53E shows an implantable OSA sensor 220, according to one embodiment of the invention. The implantable OSA sensor 220 is constructed similarly to the implantable OSA sensor 200 shown in FIGS. 53A and 53B. However, the IPMC sensor 222 includes a smaller width and longer length shape which thus may be positioned on lateral walls of the soft palate.

Figure 53F:
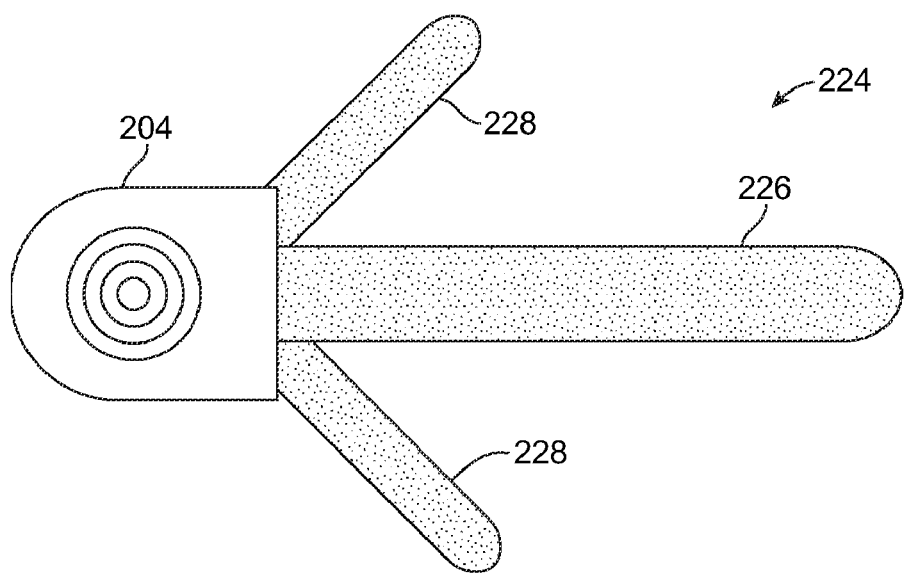

FIG. 53F shows an implantable OSA sensor 224, according to one embodiment of the invention. The implantable OSA sensor 224 is constructed similarly to the implantable OSA sensor 200 shown in FIGS. 53A and 53B. However, the IPMC sensor 226 includes a smaller width and length which may fit inside smaller mouths. At least one more IPMC sensor 228 is also shown. The IPMC sensor 228 extends at an angle away from the IPMC sensor 226. The IPMC sensor 228 is shown to be shorter and narrower than the IPMC sensor 226 and thus may be placed about the paltoglossal arch.

Figure 53G:
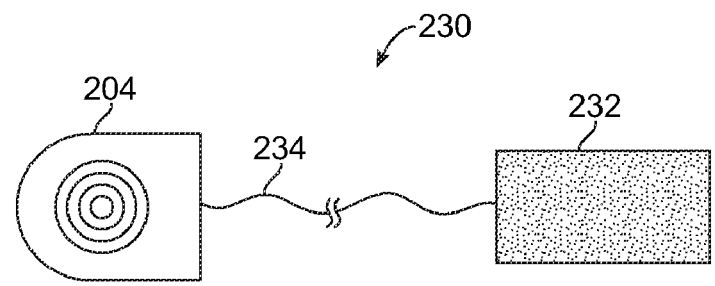

FIG. 53G shows an implantable OSA sensor 230, according to one embodiment of the invention. The implantable OSA sensor 230 is constructed similarly to the implantable OSA sensor 200 shown in FIGS. 53A and 53B. However, the IPMC sensor 232 is not integral with the transmitter device 204. The IPMC sensor 232 is remotely attached to the transmitter device 204 by cable 234. This configuration is advantageous because the transmitter device 204 may be placed in a location away from the soft or hard palate, for example outside the mouth. The cable 234 may also be detachable from the transmitter device 204, through the use of a reusable connector. The cable 234 may also be detachable from the IPMC sensor 232, through the use of a reusable connector. Thus the patient may only need to wear or connect the transmitter device 204 when sleeping. The IPMC sensor 232 may involve a rectangular shape as shown, but is not limited to such and may for example take any of the shapes disclosed herein.

Figure 53H:
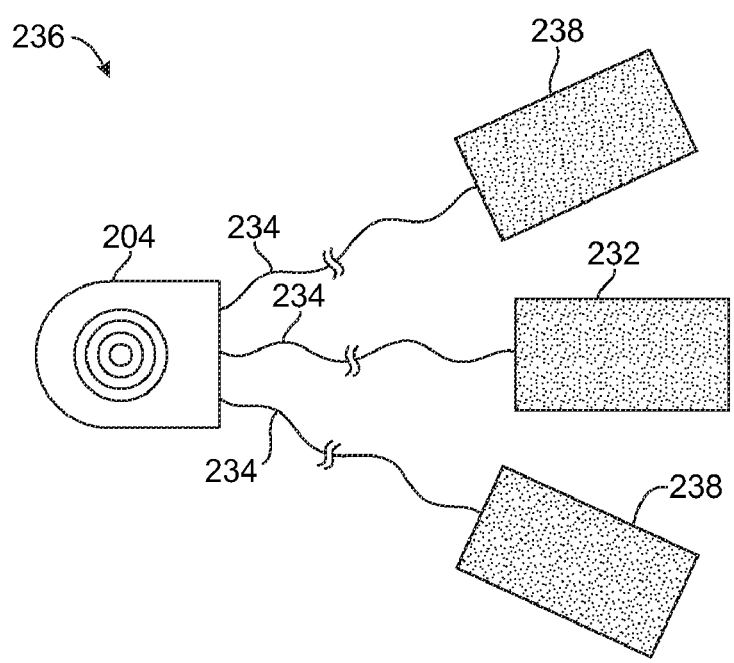

FIG. 53H shows an implantable OSA sensor 236, according to one embodiment of the invention. The implantable OSA sensor 236 is constructed similarly to the implantable OSA sensor 230 shown in FIG. 53G. However, the implantable OSA sensor 236 includes at least one more IPMC sensor 238. Two additional IPMC sensors 238 are shown, but more or less may be used. This configuration is advantageous because it allows for additional measurements in disparate sections in an airway passage of an oral cavity, for example about the pharyngeal walls, paltoglossal arch, or base of the tongue.

Figure 54A:
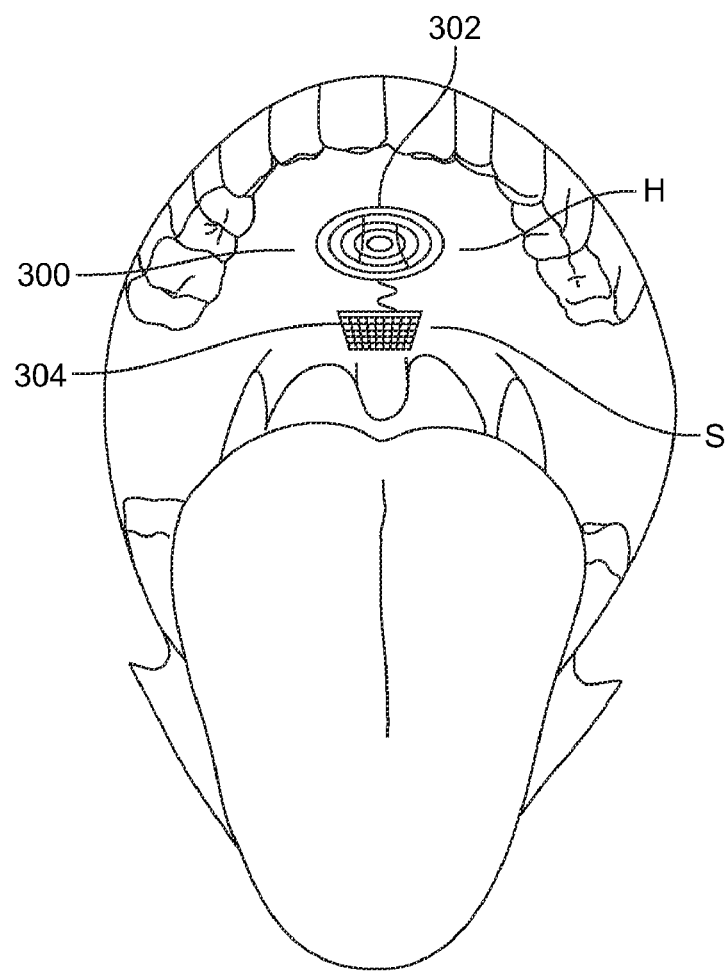
FIGS. 54A and 54B illustrates frontal views of implantable obstructive sleep apnea sensors in an airway passage of an oral cavity, according to respective embodiments of the invention.

FIG. 54A shows an implantable OSA sensor 300 in use in an airway passage of an oral cavity, according to one embodiment of the invention. The implantable OSA sensor 300 is shown extending from the hard palate H to the soft palate S. The implantable OSA sensor 300 is shown in a configuration similar to what is shown in FIG. 53G, but may take the configuration of any of the implantable OSA sensors disclosed herein. The transmitter device 302 is shown attached to the hard palate H and an IPMC sensor 304 attached to the soft palate S. The implantable OSA sensor 300 may be attached to the airway passage of an oral cavity by several methods. The implantable OSA sensor 300 may be attached by a biocompatible bonding agent or tape. The biocompatible bonding agent also may be biodegradable, for example over a short period of time, e.g. hours, in order to be easily removed after a period of rest. The implantable OSA sensor 300 may also be attached by permanent or biodegradable sutures. An incision also may be made into the airway passage of an oral cavity which the implantable OSA sensor 300 may be completely or at least partially deposited into and attached by the methods disclosed herein. The IPMC sensor also may be permanently attached in an airway passage of an oral cavity, while at least a portion of the transmitter device is detachable and removable for recharging or servicing.

When a patient experiences an OSA or snoring event the soft palate vibrates at a certain frequency and amplitude. The implantable OSA sensor 300 is vibrated or bent with the soft palate to create an electrical signal. Accordingly, the electrical signal may indicate an OSA or snoring event. The electrical signal may be transformed or reconfigured by the implantable OSA sensor, and wirelessly transmitted to a secondary device. The position of the OSA sensor 300 is not limited to the soft palate and may be placed in different positions in the airway passage of an oral cavity.

Figure 54B:
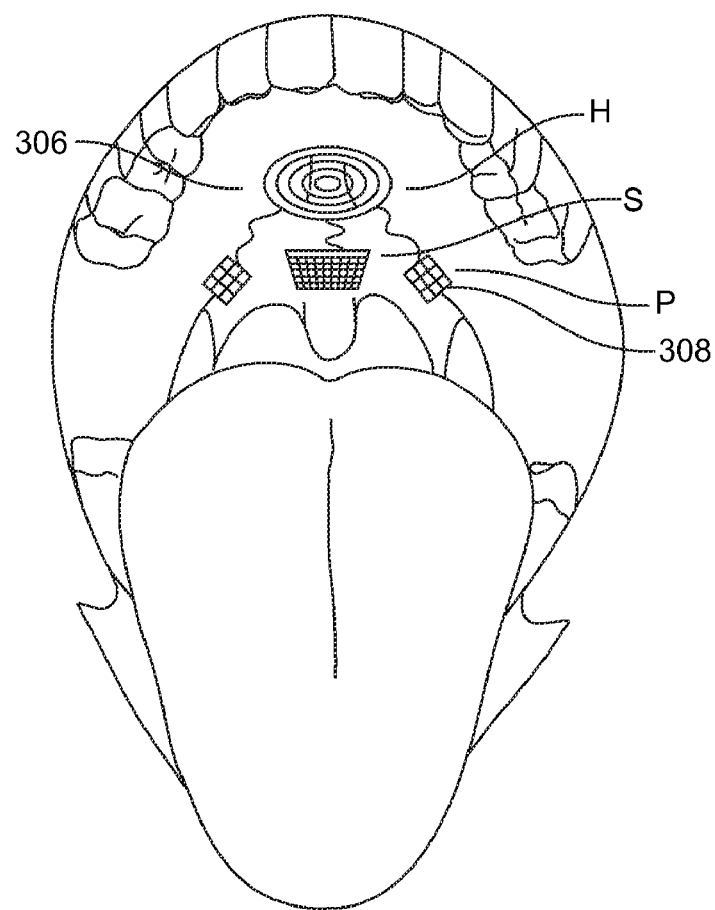

FIG. 54B shows an implantable OSA sensor 306 in use in an airway passage of an oral cavity, according to one embodiment of the invention. The implantable OSA sensor 306 is similar to what is shown in FIG. 53H, but may take the configuration of any of the implantable OSA sensors disclosed herein, for example the implantable OSA sensor in FIG. 53F. The implantable OSA sensor 306 has at least one additional IPMC sensor 308. The additional IPMC sensor 308 is placed on a pharyngeal wall P as shown. Thus the additional IPMC sensor 308 may be used to detect an OSA or snoring event according to vibrations or deflections on the pharyngeal wall P.

Figure 55A:
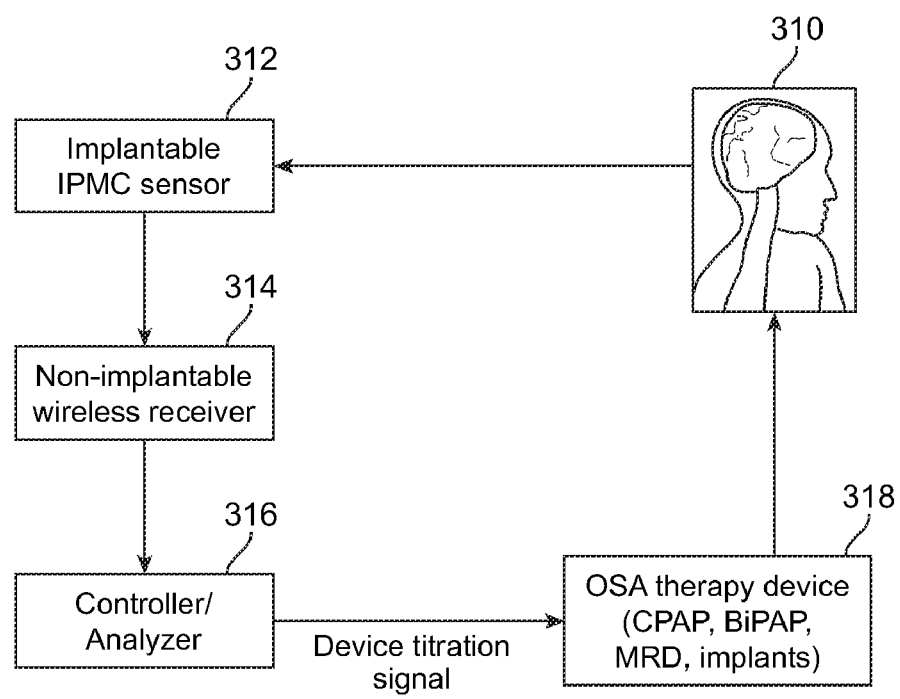
FIG. 55A illustrates a flow diagram of a system for detecting an obstructive sleep apnea event, according to one embodiment of the invention.

FIG. 55A shows a flow diagram of a system for detecting an OSA event, according to one embodiment of the invention. At operation 310 a patient experiences an OSA event or snoring event in an airway passage of an oral cavity. At operation 312 an implantable OSA sensor, previously coupled to the patient, detects the OSA event or snoring event, and accordingly generates an electronic signal. The implantable OSA sensor may also continuously broadcast a signal regardless of whether a snoring or an OSA event occurs, because normal breathing may generally vibrate the implantable OSA sensor enough to constantly generate an electronic signal. The electrical signal may also be transformed or reconfigured by the implantable OSA sensor. The implantable OSA sensor then wirelessly transmits the electronic signal to a remotely located wireless receiver which receives the electronic signal in operation 314. The wireless receiver may be within short range location (e.g. less than 10 meters) or long range location. For example the wireless receiver may be situated hundreds of miles away from the patient, for example the wireless receiver may be communicated to over air carrier waves, a direct phone line connection, or through a private or public packet-based network, such as the internet. The wireless receiver may be in continuous wireless contact with the implantable OSA sensor, or in intermittent contact. For example the implantable OSA sensor may continuously broadcast, while the wireless receiver samples the broadcast at preset intervals. The implantable OSA sensor may also broadcast at preset intervals while the wireless receiver is set to continuously receive. The implantable OSA sensor may also broadcast at preset intervals, while simultaneously the wireless receiver is synchronized to receive at the same preset intervals. The wireless receiver may also receive signals from other implantable OSA sensors, which may be in the same or a different patient.

At operation 316 a control device receives the electronic signal from the wireless receiver. The wireless receiver may be integrated with the control device, or configured as a stand-alone electronic device. The control device may store the electronic signal for later analysis. The control device may also provide an analysis of the electronic signal, e.g. interpreting whether the electronic signal represents an OSA event. The analysis may be developed into a predictive algorithm which can predict OSA events for a specific patient. The controller may optionally interact with an OSA therapy device by creating a control algorithm. The OSA therapy device receives a control signal to indicate that a therapy needs to be applied to the patient in order to alleviate the OSA event. For example the OSA therapy device may be an IPMC therapy device which forcibly moves a portion of airway passage of an oral cavity to alleviate the OSA event. In some embodiments the IPMC sensor may be configured as an IPMC actuation device as well. Other device may include electronically actuated and controlled mandibular repositioning devices, and continuous/bi-level positive airway pressure devices. The wireless receiver, control device, and OSA therapy device may also be integrally housed into one common electronic device.

Figure 55B:
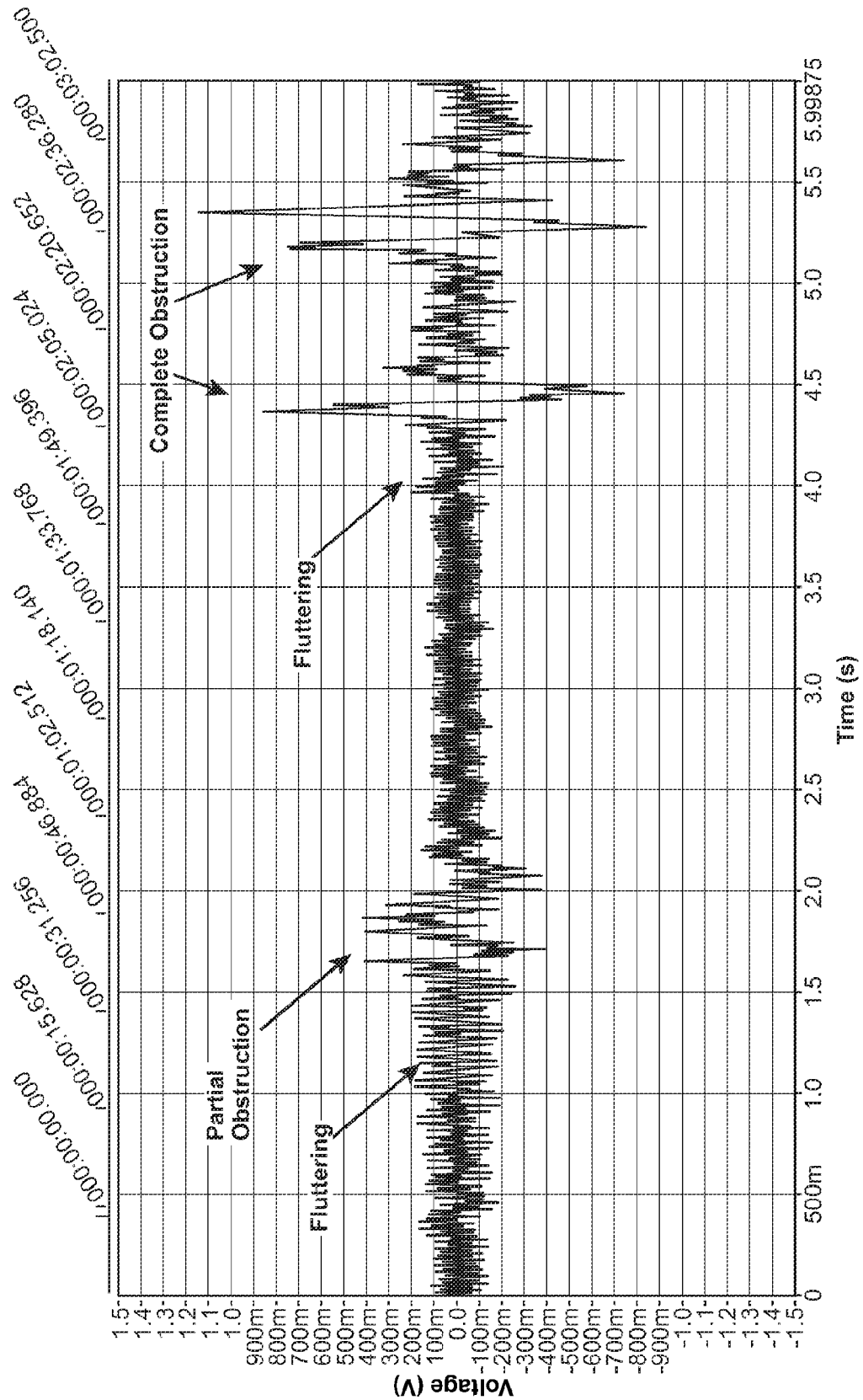
FIG. 55B illustrates a graphical signal output of an implantable obstructive sleep apnea sensor in use, according to one embodiment of the invention.

FIG. 55B shows a graphed output of an implantable OSA sensor in use in an airway passage of an oral cavity, according to one embodiment of the invention. The graphed output corresponds to the signal produced by an IPMC sensor, which may be further modified by a transmitter device. The graphed output shows a Fluttering signal which may indicate snoring or the beginning of an OSA event. The Fluttering signal leads to a increased Partial Obstruction signal. The graph further shows a second Fluttering signal, leading to Complete Obstruction signals. Thus the graph shows a complete correlation between movement in an airway passage of an oral cavity and the signal generated by the implantable OSA sensor. The signals shown may be processed or analyzed to be used to alleviate or predict future OSA events.

OSA Implantable Sensor Activated Mandibular Repositioning Device

Medical solutions to OSA include mandibular repositioning devices (MRD). A MRD typically includes at least an upper portion for coupling to the upper jaw, and a lower portion for coupling to the lower jaw. The two portions lock together to form an unnatural jaw position by repositioning/advancing the lower jaw. The result is that the base of the tongue is also moved forward to prevent it from closing the airway. Prior art MRDs may be effective but are not well-liked by many patients. The unnatural position of the jaw must be assumed throughout a night's sleep, often for several hours. The unnatural position locks the jaw and causes pain to the patient. Patients who may otherwise benefit from a mandibular repositioning device will abandon treatment because of the discomfort. Patients using a mandibular repositioning device are forced to wear the device continuously, regardless of when OSA events occur, and thus may suffer from unnecessary pain and discomfort.

Figure 56A:
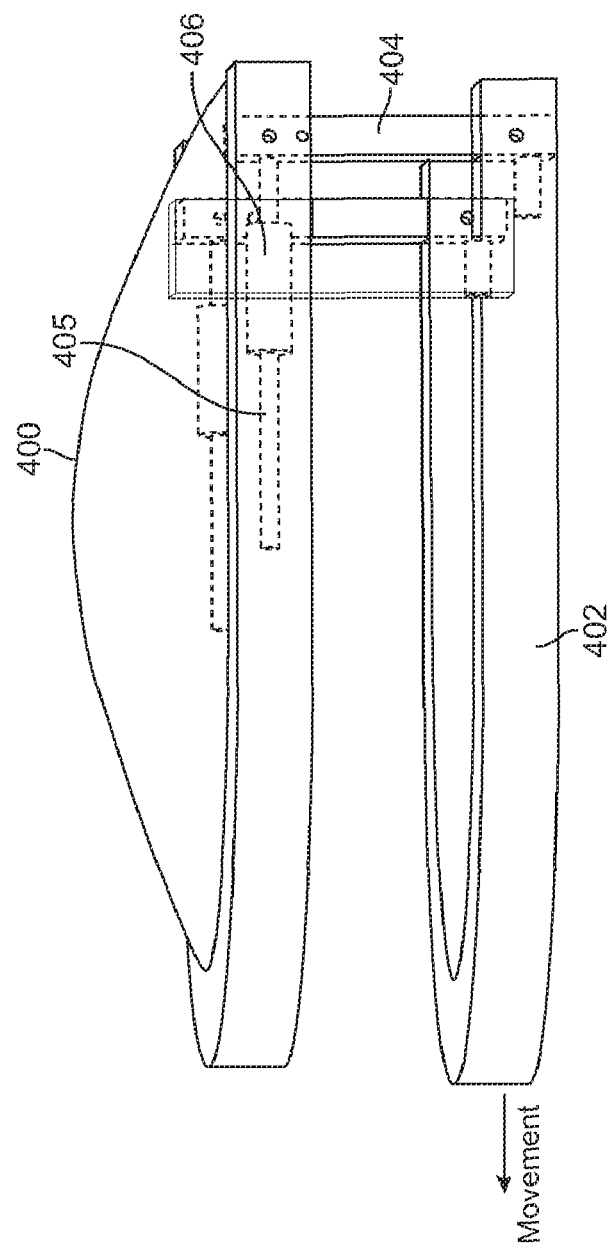
FIG. 56A illustrates a perspective view of a mandibular repositioning device, according to one embodiment of the invention.

FIG. 56A shows a mandibular repositioning device (MRD), in accordance with one embodiment of the present invention. The MRD shown in FIG. 56A offers a significant improvement over prior art devices. The patient's lower jaw may only move in response to OSA events and thus not be locked for an entire night's sleep. Accordingly, a patient using the MRD would not have the discomfort and pain that is associated with prior art devices that lock the jaw continuously. The patient will accordingly realize the benefits of treating OSA and also not suffer from the pain that prior art MRDs imposed.

The MRD includes a fixed upper jaw positioner 400. The fixed upper jaw positioner 400 is configured to mate and align with a portion of the upper palate and/or upper dentures of a patient who suffers from OSA. The fixed upper jaw positioner 400 is typically a custom match to the patient and may be constructed from a variety of polymers or metals. The fixed upper jaw positioner 400 is sufficiently constructed such that it will remain affixed to a portion of the upper palate and/or upper dentures when force is applied in a lateral manner relative to the top biting surface of the upper dentures.

The MRD also includes a moveable lower jaw positioner 402. The moveable lower jaw positioner 402 is configured to mate and align with at least a portion of the lower dentures of the patient and is similarly constructed to the fixed upper jaw positioner 400. The moveable lower jaw positioner 402 is sufficiently constructed such that it will remain affixed to the lower dentures when force is applied in a lateral manner relative to the top biting surface of the lower dentures.

At least one linkage 404 connects the fixed upper jaw positioner 400 and the moveable lower jaw positioner 402. In the example shown, two linkages are included, but only one is required. The linkage 404 includes a first end and a second end. The first end is moveably attached to the fixed upper jaw positioner 400, for example by a pin or a hinge. The second end is likewise connected to the moveable lower jaw positioner 402.

The fixed upper jaw positioner 400 can include at least one jaw actuator 406. In the example shown, two jaw actuators 406 are shown, but only one is required. In one embodiment, the jaw actuator 406 can be an ultrasonic linear piezoelectric motor. Rechargeable battery power and electronics for the actuator are housed within the upper jaw positioner 400. The jaw actuator 406 may alternatively be positioned on or about the moveable lower jaw positioner 402 or the linkage 404.

In use, the jaw actuator 406 actuates a moveable rod 408, which is linked to the first end of the linkage 404, to move in the backwards direction. The actuation results in a torque which in turn causes the second end of the linkage 404 to move the moveable lower jaw positioner 402, and thus the patient's lower jaw, in the forward direction. The resulting movement can alleviate an OSA event. However, non-tongue related OSA events may not be alleviated. The jaw actuator 406 may hold the moveable lower jaw positioner 402 until the OSA event subsides, and then move the lower jaw positioner 102 back into its original position.

Figure 56B:
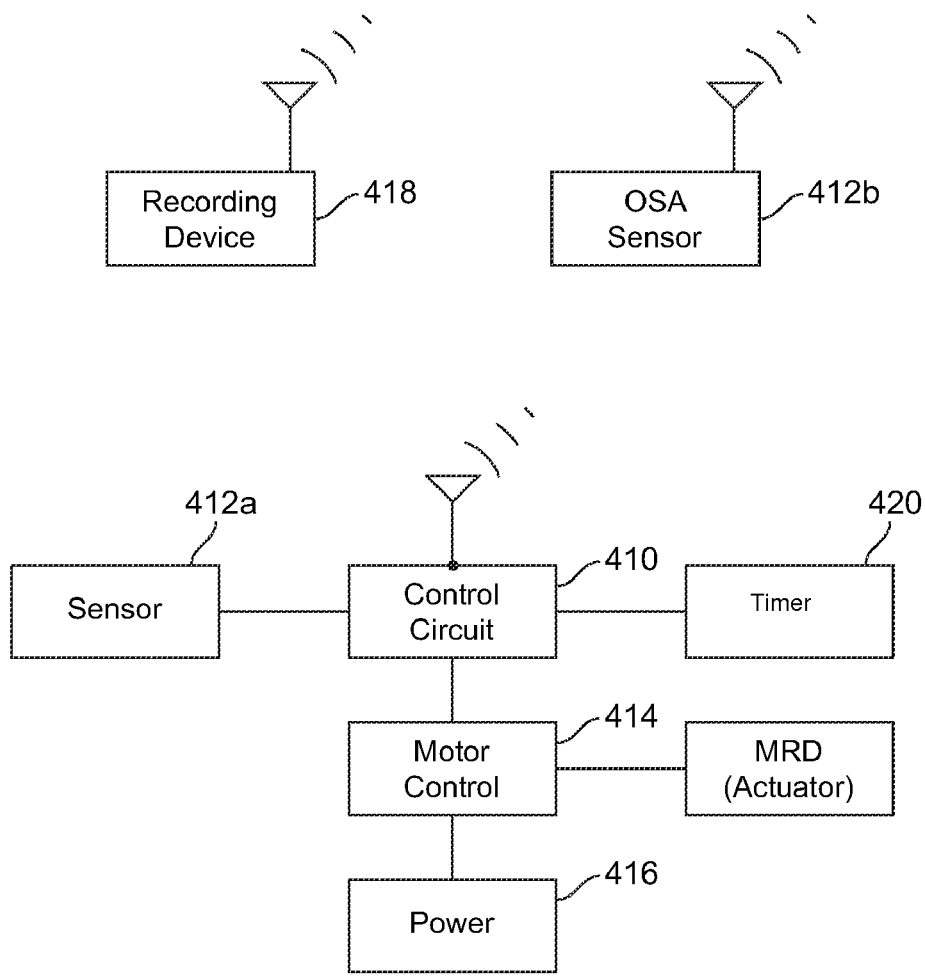
FIG. 56B illustrates a schematic diagram of a mandibular repositioning device in conjunction with a implantable obstructive sleep apnea sensor, according to one embodiment of the invention.

FIG. 56B shows a block diagram of a system which can be configured to control and activate the MRD. The control circuit 410 may determine when an OSA event occurs and can operate the MRD to alleviate the OSA event. A sensor 412a is electronically coupled to the control circuit. Sensor 412a senses whether an OSA event occurs. For example the sensor 412a may detect vibrations in the jaw area which are OSA related. The sensor 412a may be an implantable OSA sensor as described herein. The external sensor 412b may transmit a wireless signal to the control circuit to identify an OSA event. The external sensor 412b may alternatively be plugged into the implantable OSA sensor by way of a detachable plug. Alternatively, an external sensor 412b may be electronically coupled to the control circuit 110. For example, the sensor may measure blood pressure or oxygen levels which fluctuate according to an OSA event.

The control circuit may also receive instructions from an outside controller, for example as shown in operations 316 and 318 of FIG. 55A. Thus, the MRD device may be the OSA therapy device of operation 318.

The control circuit 410 is configured to instruct the motor control 414 to actuate the MRD upon realization of an OSA event. Power 416 can be supplied to the MRD by a rechargeable battery. When the event subsides, the motor control 414 can move the MRD back to its original position. Additionally, the sensor 412b may be manually configurable to activate the MRD on command. Thus, the patient, if desired, may wish to be in a locked jaw position continuously or for a programmed amount of time.

An optional recording device 418 may be used in conjunction with the system, and wirelessly coupled to the control circuit 410 and sensor 412. The recording device may be used to determine efficacy of the MRD in a specific patient, as the MRD may not treat all causes of an OSA event. Thus in use the recording device 418 can record when an OSA event occurs and if the MRD worked to alleviate the OSA event. For example if an OSA event occurs and the sensor 412 shows that the event subsided temporally in conjunction with activation with the MRD, the resulting data can show the MRD to be effective in that patient. However, if an OSA event occurred and the sensor 412 showed that the event subsided long after the activation of the MRD (e.g. self-resolved), the resulting data could show that the MRD may not have been effective for that patient at that particular time and OSA event. This is a significant advantage over prior art devices which had no means to integrally determine efficacy.

An optional timer 420 may also be used in conjunction with the system. The timer 420 can be programmed to activate the MRD after the timer counts down. This is advantageous to avoid unwanted MRD actuations while the patient is still awake. Unwanted activations may cause discomfort and prevent the patient from falling asleep. For example the timer 420 may be set to allow the control circuit 400 to activate 25 minutes after being worn by the patient. This would ensure that the patient is fully asleep when the MRD is functioning.

Figure 56C:
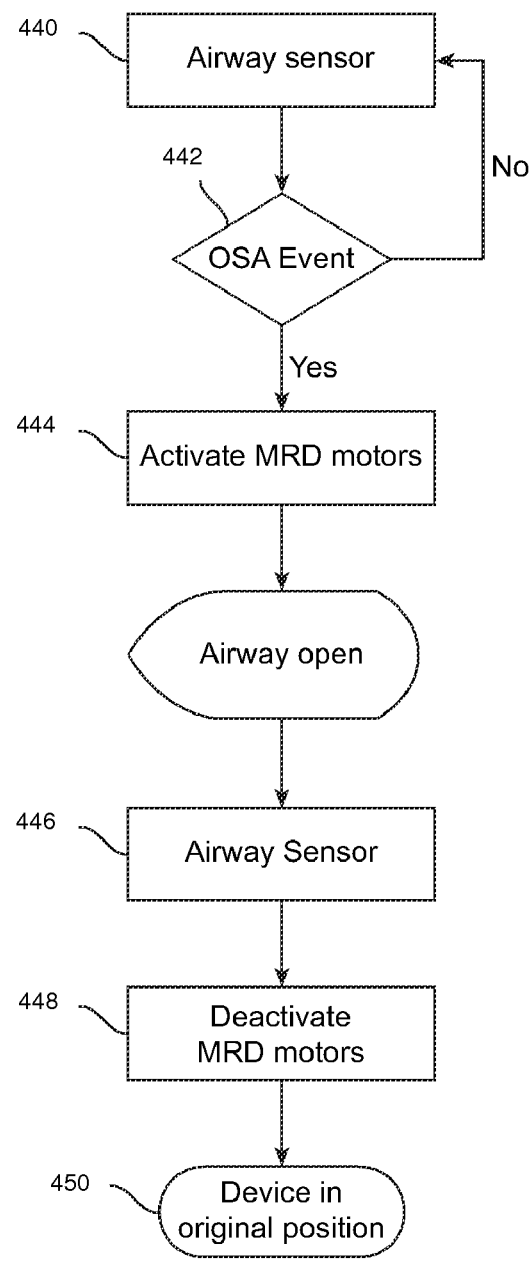
FIG. 56C illustrates a flow diagram of a system for detecting and treating an obstructive sleep apnea event using a mandibular repositioning device, according to one embodiment of the invention.

FIG. 56C shows a method of alleviating an OSA event. The method incorporates the device and systems described herein, for example as shown in FIGS. 56A and 56B. At operation 440 an airway sensor 412b, such as an implantable OSA sensor, can send a signal to the control circuit 410. At operation 442 the control circuit 410 can make a determination whether an OSA event has occurred. Alternatively the airway sensor 412b may only send signals if an OSA event has occurred, and the control circuit 410 can make no determination and act to resolve the OSA event. At operation 444 the MRD can be activated and the lower jaw can be moved forward to alleviate the OSA event by opening the airway. At operation 446 the airway sensor 412b can confirm to the control circuit 410 that the OSA event has subsided. At operation 448 the control circuit 410 can instruct the motor control 414 to move the MRD to the original position, e.g. jaw in the normal position. At operation 450 the MRD can be positioned back to its original position.

OSA Implantable Sensor Auto-Titration of CPAP/BiPAP

A continuous positive airway pressure (CPAP) machine is used mainly by patients for the treatment of OSA events at home. The CPAP machine stops an OSA event by delivering a stream of compressed air via a hose to a nasal pillow, nose mask or full-face mask, splinting the airway (keeping it open under air pressure) so that unobstructed breathing becomes possible for reducing and/or preventing OSA events.

The CPAP machine blows air at a prescribed pressure (also called the titrated pressure). The necessary pressure is usually determined by a sleep physician after review of a study supervised by a sleep technician during an overnight study (polysomnography) in a sleep laboratory. The titrated pressure is the pressure of air at which most OSA events have been prevented, and it is usually measured in centimeters of water (cm $H_2O$). The pressure required by most patients with sleep apnea ranges between 6 and 14 cm $H_2O$. A typical CPAP machine can deliver pressures between 4 and 20 cm $H_2O$. More specialized units can deliver pressures up to 25 or 30 cm $H_2O$.

APAP or AutoPAP or AutoCPAP (Automatic Positive Airway Pressure) automatically titrates, or tunes, the amount of pressure delivered to the patient to the minimum required to maintain an unobstructed airway on a breath-by-breath basis by measuring the resistance in the patient's breathing, thereby giving the patient the precise pressure required at a given moment and avoiding the compromise of fixed pressure. VPAP or BiPAP (Variable/Bilevel Positive Airway Pressure) provides two levels of pressure: Inspiratory Positive Airway Pressure (IPAP) and a lower Expiratory Positive Airway Pressure (EPAP) for easier exhalation.

Figure 57A:
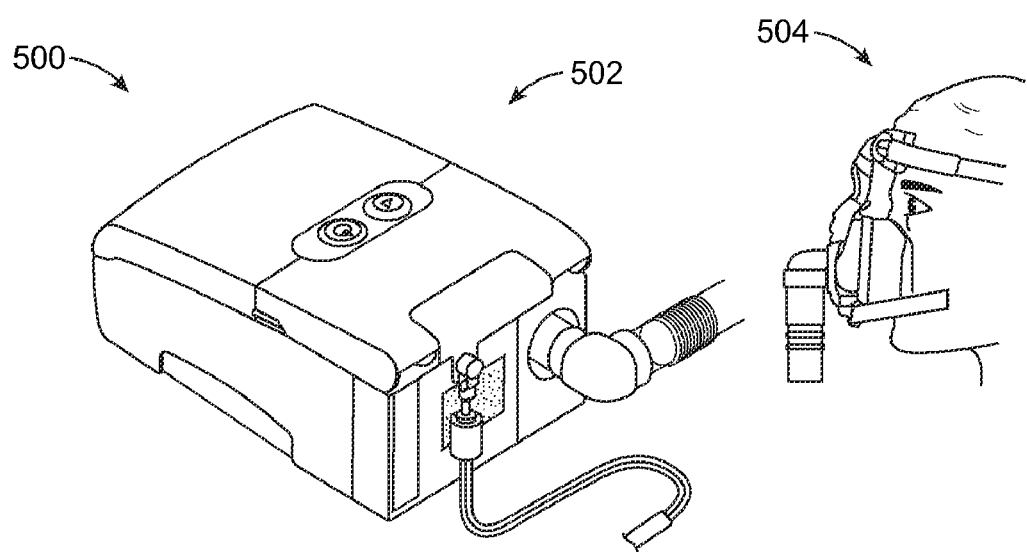
FIG. 57A illustrates a simplified schematic diagram of a positive airway pressure apparatus for use with a implantable obstructive sleep apnea sensor, according to one embodiment of the invention.

FIG. 57A shows a positive airway pressure (PAP) system 500, which may be a CPAP, APAP, VPAP, or APAP machine, according to one embodiment of the invention. The PAP system 500 generally includes a control system 502, and a connected inspiration mask 504 which forms a breathing circuit. PAP systems 500 generally include electronic controls, sensors, and an air pump system. PAP systems are known in the art, for example as shown in published Patent Application US 2008/0041383, the entirety of which is incorporated by reference herein. Prior art PAP systems use pressure sensors to detect OSA events. For example fluctuations or lower or higher pressure readings than a predetermined norm may indicate to a prior art PAP system that an OSA event has occurred. The PAP system 500, in accordance with one embodiment of the invention, includes an implantable OSA sensor (not shown) wirelessly coupled to the control system 502. The implantable OSA sensor (not shown) is advantageously configured to work in conjunction, or in lieu of, with a pressure sensor (not shown). Thus the implantable OSA sensor may work with the pressure sensor to generate an optimum pressure point, or optimum input pressure.

Figure 57B:
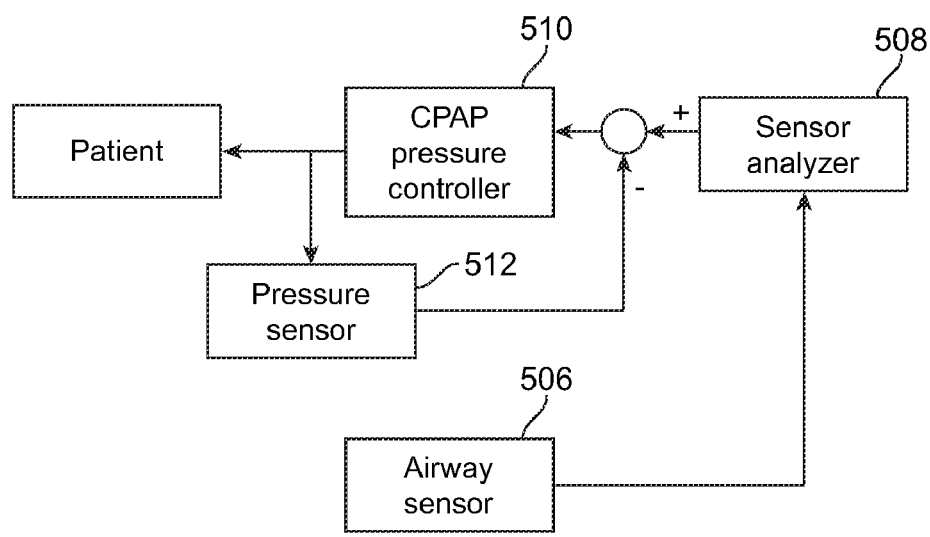
FIG. 57B illustrates a flow diagram of a system for detecting and treating an obstructive sleep apnea event using a positive airway pressure apparatus, according to one embodiment of the invention.

FIG. 57B shows a flow chart for use of a PAP system, according to one embodiment of the invention. At operation 506 an airway sensor can detect an OSA event in a patient. The airway sensor may be an implantable OSA sensor as described herein. The patient is also coupled to a PAP system. The implantable OSA sensor may generate and continuously, or intermittently, output a signal to a sensor analyzer. The output signal may be sent from the implantable OSA sensor to the sensor analyzer as a wireless signal. At operation 508 a sensor analyzer analyzes the output signal of the implantable OSA sensor. The sensor analyzers may be further electronically based on neural network algorithms or adaptive algorithms, and may be based on adaptive, nonlinear, or linear controls. The sensor analyzer can output the signal to the PAP pressure controller at operation 510. In operation 512 a conventional pressure sensor is monitoring air pressure from the patient. The conventional pressure sensor may also sense other patient inputs, e.g. airway resistance. The conventional pressure sensor also sends information to the PAP pressure controller in operation 512. The PAP pressure controller can use the information from the conventional pressure sensor and the output signal of the sensor analyzer to generate an optimum input pressure, and thus relieve the OSA event. The PAP pressure controller strategy may be based on neural network algorithms or adaptive algorithms, and may be based on adaptive, nonlinear, or linear controls. Thus, the PAP system may learn how a particular patient reacts to OSA events and titrate pressure in a faster and more predictable manner than prior art PAP systems. In an alternative embodiment the conventional pressure sensor is not present, and the PAP system relies on the implantable OSA sensor for signaling OSA events.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

What is claimed is:

1. A method for sensing obstructive sleep apnea in a patient, comprising:

attaching an ionic polymer metal composite (IPMC) sensor at one of a hard palate and a soft palate of an airway passage in an oral cavity of the patient;

electrically coupling a transmitter device to the IPMC sensor;

placing the transmitter device at a location away from the hard palate and the soft palate;

generating an electrical output from the IPMC sensor when a change in a shape in the oral cavity occurs;

transmitting a signal from the transmitter device which is based on the generated electrical output from the IPMC sensor;

wherein the signal is transmitted by a wireless transmitter component of the transmitter device that is electrically coupled to the IPMC sensor and located away from the hard palate and the soft palate.

2. The method of claim 1 additionally comprising analyzing the transmitted signal.

3. The method of claim 2 wherein analyzing includes creating a predictive algorithm based on the transmitted signal.

4. The method of claim 3 additionally comprising sending a control signal to a obstructive sleep apnea treatment device based on the analyzed transmitted signal.

5. The method of claim 1 additionally comprising translating the generated electrical output into the signal.

6. The method of claim 5 wherein the signal is digital.

7. The method of claim 5 wherein the signal is analog.

8. The method of claim 1 wherein the transmitter device includes a capacitor.

9. The method of claim 1 wherein the transmitter device transmits the signal according to a wireless transmission standard.

10. The method of claim 1, wherein the transmitter device includes a battery.

11. The method of claim 10 wherein at least a portion of the transmitter device is detachable from the IPMC sensor for recharging the battery.

12. The method of claim 1 additionally comprising:

receiving the signal at a wireless receiver; and recording the signal at a control device electronically coupled to the wireless receiver.

13. The method of claim 12 wherein the control device additionally performs an analysis of the signal.

14. The method of claim 1 wherein the IPMC sensor includes an electro active polymer material.

15. The method of claim 1 wherein the IPMC sensor is configured as an elongated strip.

16. The method of claim 1 wherein the IPMC sensor is placed on the soft palate.

17. The method of claim 1 wherein the IPMC sensor is placed on the soft palate using an adhesive.

18. The method of claim 1 wherein the IPMC sensor is implanted into the soft palate.

19. The method of claim 1 wherein signal is an amplified analog signal.

* * * * *